(12) United States Patent
Boehringer et al.

(10) Patent No.: US 7,501,413 B2
(45) Date of Patent: Mar. 10, 2009

(54) DICARBOXAMIDE DERIVATIVES

(75) Inventors: Markus Boehringer, Moehlin (CH); Katrin Groebke Zbinden, Basel (CH); Wolfgang Haap, Loerrach (DE); Hans Hilpert, Muenchenstein (CH); Jacques Himber, Guebwiller (FR); Roland Humm, Auggen (DE); Hans Iding, Rheinfelden (DE); Dietmar Knopp, Basel (CH); Narendra Panday, Basel (CH); Fabienne Ricklin, Hombourg (FR); Christoph Martin Stahl, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 394 days.

(21) Appl. No.: 11/263,497

(22) Filed: Oct. 31, 2005

(65) Prior Publication Data

US 2006/0106016 A1    May 18, 2006

(30) Foreign Application Priority Data

Nov. 3, 2004  (EP) .................................. 04105465
Jan. 12, 2005 (EP) .................................. 05100132

(51) Int. Cl.
*C07D 413/02* (2006.01)
*C07D 401/02* (2006.01)
*A61K 31/44* (2006.01)

(52) U.S. Cl. ................. 514/235.2; 514/252.1; 514/278; 514/332; 514/349; 544/124; 544/405; 546/15; 546/255; 546/308

(58) Field of Classification Search ....................... None
See application file for complete search history.

(56) References Cited

FOREIGN PATENT DOCUMENTS

| WO | WO 00/71508 | 11/2000 |
|----|-------------|---------|
| WO | WO 01/64642 | 9/2001 |
| WO | WO 03/045912 | 6/2003 |
| WO | WO 2004/046138 | 6/2004 |
| WO | WO 2004/006369 | 8/2004 |
| WO | WO 2005/092881 | 10/2005 |

OTHER PUBLICATIONS

Donkor et al, Journal of Medicinal Chemistry, 2003, vol. 46, No. 6, pp. 1041-1046.*

* cited by examiner

*Primary Examiner*—Zinna N Davis
(74) *Attorney, Agent, or Firm*—George W. Johnston; Dennis P. Tramaloni; Brian C. Remy

(57) ABSTRACT

The invention is concerned with novel dicarboxamide derivatives of formula (I)

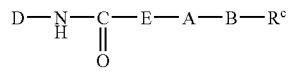

wherein A, B, $R^c$, D and E are as defined in the description and in the claims, as well as physiologically acceptable salts thereof. These compounds inhibit the coagulation factor Xa and can be used as medicaments.

42 Claims, No Drawings

DICARBOXAMIDE DERIVATIVES

SUMMARY OF THE INVENTION

The invention is concerned with novel dicarboxamide derivatives of the formula (I)

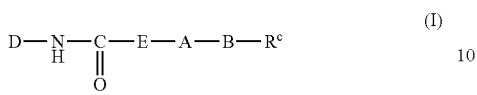

wherein

A is —CONH— or —NHCO—;

B is optionally substituted phenyl, optionally substituted heteroaryl or optionally substituted heterocyclyl;

$R^c$ is optionally substituted aryl, optionally substituted heteroaryl or optionally substituted heterocyclyl, one or two carbon atoms of said aryl, heteroaryl or heterocyclyl ring optionally being replaced with a carbonyl group;

D is aryl optionally substituted by one, two or three halogen atoms independently selected from chlorine, fluorine and bromine or heteroaryl optionally substituted by one, two or three halogen atoms independently selected from chlorine, fluorine and bromine;

E is E-1:

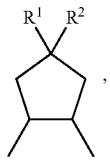

E-2:

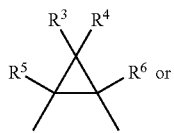

E-3:

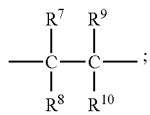

$R^1$ and $R^2$ are independently from each other hydrogen, halogen, $C_{1-6}$ alkyl, $C_{3-7}$ cycloalkyl, $C_{3-7}$ cycloalkyl $C_{1-6}$ alkyl, amino, mono-substituted amino, di-substituted amino, hydroxy, $C_{1-6}$ alkoxy, mono-substituted amino-$C_{1-6}$ alkyl, di-substituted amino-$C_{1-6}$ alkyl, hydroxyl $C_{1-6}$ alkyl or $R^1$ and $R^2$ together form

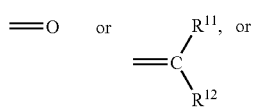

$R^1$ and $R^2$ are bonded to each other to form optionally substituted heterocyclyl, together with the carbon atom to which $R^1$ and $R^2$ are attached;

$R^3$ and $R^4$ are independently from each other hydrogen, $C_{1-6}$ alkyl, carboxyl, $C_{1-6}$ alkoxycarbonyl, carbamoyl, mono- or di-substituted amino-carbonyl, optionally substituted aryl carbonyl, optionally substituted heterocyclylcarbonyl, optionally substituted heteroarylcarbonyl, optionally substituted aryl, optionally substituted heteroaryl, optionally substituted heterocyclyl, hydroxyl $C_{1-6}$ alkyl, halo $C_{1-6}$ alkyl, cyano $C_{1-6}$ alkyl, $C_{1-6}$ alkoxy $C_{1-6}$ alkyl, amino $C_{1-6}$ alkyl, mono- or di-substituted amino-$C_{1-6}$ alkyl, optionally substituted aryl $C_{1-6}$ alkyl, optionally substituted heterocyclyl $C_{1-6}$ alkyl, optionally substituted heteroaryl $C_{1-6}$ alkyl, optionally substituted aryl $C_{1-6}$ alkoxy $C_{1-6}$ alkyl, optionally substituted heteroaryl $C_{1-6}$ alkoxy $C_{1-6}$ alkyl, optionally substituted heterocyclyl $C_{1-6}$ alkoxy $C_{1-6}$ alkyl or $R^3$ and $R^4$ are bonded to each other to form $C_{3-7}$ cycloalkyl, together with the carbon atom to which $R^3$ and $R^4$ are attached;

$R^5$ and $R^6$ are independently from each other hydrogen, $C_{1-6}$ alkyl, cyano, $C_{1-6}$ alkoxycarbonyl, $C_{2-6}$ alkenyloxycarbonyl, $C_{2-6}$ alkynyloxycarbonyl, hydroxyl $C_{1-6}$ alkyl, $C_{1-6}$ alkoxycarbonyl, carboxyl, mono- or di-$C_{1-6}$ alkyl substituted amino-carbonyl, aminocarbonyl, optionally substituted heterocyclyl carbonyl, optionally substituted heteroaryl carbonyl or optionally substituted aryl carbonyl;

$R^7$, $R^8$, $R^9$ and $R^{10}$ are independently from each other hydrogen, $C_{1-6}$ alkyl or hydroxy;

$R^{11}$ and $R^{12}$ are independently from each other hydrogen, $C_{1-6}$ alkyl or $C_{2-6}$ alkenyl;

and pharmaceutically acceptable salts thereof.

Further, the invention is concerned with a process for the manufacture of the above compounds, pharmaceutical preparations which contain such compounds as well as the use of these compounds for the production of pharmaceutical preparations.

The compounds of formula (I) are compounds that inhibit the activity of coagulation factor Xa. These compounds consequently influence blood coagulation. They therefore inhibit the formation of thrombi and can be used for the treatment and/or prevention of thrombotic disorders, such as amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. Factor Xa inhibitors of this invention may form part of a combination therapy with an anticoagulant with a different mode of action or with a platelet aggregation inhibitor or with a thrombolytic agent. Furthermore, these compounds have an effect on tumor cells and prevent metastases. They can therefore also be used as antitumor agents.

Other inhibitors of factor Xa, which are not structurally related to the compounds of the present invention, had previously been suggested for the inhibition of the formation of thrombi and for the treatment of related diseases (WO 03/045912). However, there is still a need for novel factor Xa inhibitors which exhibit improved pharmacological properties, e.g. an improved selectivity towards coagulation factor Xa.

The present invention provides the novel compounds of formula (I) which are factor Xa inhibitors, intermediates for the synthesis of compounds of formula (I), and methods of using compounds of formula (I). The compounds of the present invention unexpectedly inhibit coagulation factor Xa and also exhibit improved pharmacological properties compared to other compounds already known in the art.

DETAILED DESCRIPTION OF THE INVENTION

All patents, patent applications, and publications cited herein are incorporated by reference in their entirety. In the event of a conflict in teachings, the present disclosure is controlling.

Definitions

Unless otherwise indicated, the following definitions are set forth to illustrate and define the meaning and scope of the various terms used to describe the invention herein.

The term "halogen" or "halo" means fluorine, chlorine, bromine and iodine, with fluorine, chlorine and bromine being preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl is more preferred.

The term "$C_{2-6}$ alkynyl", alone or in combination with other groups, means a straight-chain or branched hydrocarbon residue comprising a tripple bond and 2 to 6 carbon atoms, such as e.g. 2-propinyl.

The term "halo $C_{1-6}$ alkyl" means $C_{1-6}$ alkyl substituted by one or more same or different halogen atoms independently selected from the group consisting of chlorine, fluorine and bromine.

The term "cyano $C_{1-6}$ alkyl" means $C_{1-6}$ alkyl substituted by one or more cyano groups, preferably one cyano group.

The term "hydroxy $C_{1-6}$ alkyl" means $C_{1-6}$ alkyl substituted by one or more hydroxy groups, preferably one or two hydroxy groups.

The term "$C_{3-7}$ cycloalkyl", alone or in combination with other groups, means a saturated monovalent cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "$C_{2-6}$ alkenyl", alone or in combination with other groups, means a straight-chain or branched hydrocarbon residue comprising an olefinic bond, having two to six carbon atoms, such as e.g. ethenyl, 2-propenyl.

The term "aryl", alone or in combination with other groups, means a phenyl or a naphthyl group, preferably a phenyl group. The term "optionally substituted aryl" means an aryl group described above, which is optionally substituted by one to five, preferably one to three substituents independently selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro and cyano.

The term "heterocyclyl", alone or combination with other groups, means non-aromatic monocyclic radicals of three to eight ring atoms in which one or two ring atoms are heteroatoms selected from N, O, or $S(O)_n$ (where n is an integer from 0 to 2), the remaining ring atoms being C. One or two ring carbon atoms of heterocyclyl group may be replaced with a carbonyl group.

The term "optionally substituted heterocyclyl" means a heterocyclyl group described above, which is optionally substituted independently by one, two, or three substituents, preferably one or two substituents selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably selected from the group consisting of halogen, hydroxy, $C_{1-6}$ alkyl, halo $C_{1-6}$ alkyl, $C_{1-6}$ alkoxy, acyl, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano, more preferably selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro and cyano.

The term "heteroaryl", alone or combination with other groups, means a monocyclic or bicyclic radical of 5 to 12 ring atoms having at least one aromatic ring containing one, two, or three ring heteroatoms selected from N, O, and S, the remaining ring atoms being C, with the understanding that the attachment point of the heteroaryl radical will be on an aromatic ring. One or two ring carbon atoms of heteroaryl group may be replaced with a carbonyl group. The term "optionally substituted heteroaryl" means a heteroaryl group described above, which is optionally substituted independently with one, two, or three substituents, preferably one or two substituents selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The term "optionally substituted phenyl" means a phenyl group optionally substituted by one to five substituents, preferably one to three substituents independently selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro and cyano.

The term "mono-substituted amino" and "di-substituted amino", alone or combination with other groups, mean —NHR and —NRR' respectively, in which R and R' are independently selected from the group consisting of hydroxy, $C_{1-6}$ alkyl, hydroxy $C_{1-6}$ alkyl, $C_{1-6}$ alkoxy $C_{1-6}$ alkyl, carbamoyl $C_{1-6}$ alkyl, halo $C_{1-6}$ alkyl, $C_{3-7}$ cycloalkyl, $C_{3-7}$ cycloalkyl $C_{1-6}$ alkyl, $C_{1-6}$ alkoxy, $C_{1-6}$ alkyl sulfonyl, $C_{1-6}$ alkyl sulfinyl, $C_{1-6}$ alkylthio, mono- or di-$C_{1-6}$ alkyl substituted amino-sulfonyl, mono- or di-$C_{1-6}$ alkyl substituted amino-sulfinyl, mono- or di-$C_{1-6}$ alkyl substituted amino-thio, mono- or di-$C_{1-6}$ alkyl substituted amino-$C_{1-6}$ alkyl, mono- or di-$C_{1-6}$ alkyl substituted aminocarbonyl-$C_{1-6}$ alkyl, acyl, halo $C_{1-6}$ alkylcarbonyl and $C_{1-6}$ alkoxycarbonyl, preferably selected from the group consisting of hydroxy, $C_{1-6}$ alkyl, hydroxy $C_{1-6}$ alkyl, $C_{1-6}$ alkoxy $C_{1-6}$ alkyl, carbamoyl $C_{1-6}$ alkyl, halo $C_{1-6}$ alkyl, $C_{3-7}$ cycloalkyl, $C_{3-7}$ cycloalkyl $C_{1-6}$ alkyl, $C_{1-6}$ alkoxy, $C_{1-6}$ alkyl sulfonyl, $C_{1-6}$ alkyl sulfinyl, $C_{1-6}$ alkylthio, mono- or di-$C_{1-6}$ alkyl substituted amino-sulfonyl, mono- or di-$C_{1-6}$ alkyl substituted amino-sulfinyl, mono- or di-$C_{1-6}$ alkyl substituted amino-thio, mono- or di-$C_{1-6}$ alkyl substituted amino-$C_{1-6}$ alkyl, mono- or di-$C_{1-6}$ alkyl substituted aminocarbonyl-$C_{1-6}$ alkyl, acyl and $C_{1-6}$ alkoxycarbonyl, preferably selected from the group consisting of hydroxy, $C_{1-6}$ alkyl, hydroxy $C_{1-6}$ alkyl, halo $C_{1-6}$ alkyl, $C_{3-7}$ cycloalkyl, $C_{3-7}$ cycloalkyl $C_{1-6}$ alkyl, $C_{1-6}$ alkoxy, $C_{1-6}$ alkyl sulfonyl, $C_{1-6}$ alkyl sulfinyl, $C_{1-6}$ alkylthio, mono- or di-$C_{1-6}$ alkyl substituted amino-sulfonyl, mono- or di-$C_{1-6}$ alkyl substituted amino-sulfinyl, mono- or di-$C_{1-6}$ alkyl substituted amino-thio, acyl and $C_{1-6}$ alkoxycarbonyl.

The term "acyl", alone or combination with other groups, means —C(=O)R, in which R is H or $C_{1-6}$ alkyl.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammoniumsalt. The term "pharmaceutically acceptable salts" also refers to such salts. Acid addition salts as described above are preferred.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino.

"Enantiomerically pure" means that the enantiomeric excess exceeds 95%.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) wherein E is E-1 or E-2 have at least two asymmetric centers on the adjacent carbon atoms belonging to a cyclopentane or cyclopropane ring. Thus, they can therefore exist as a diastereomeric mixture of trans and cis compounds, or as a pure trans compounds or a pure cis compounds. Moreover, each of trans and cis compounds can exist as an enantiomeric mixture or as optically pure compounds. The compounds of this invention wherein E is E-3 can possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

Thus, the invention provides novel dicarboxamide derivatives of the formula (I)

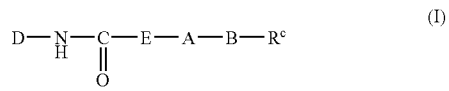

wherein

A is —CONH— or —NHCO—;

B is optionally substituted phenyl, optionally substituted heteroaryl or optionally substituted heterocyclyl;

$R^c$ is optionally substituted aryl, optionally substituted heteroaryl or optionally substituted heterocyclyl, one or two carbon atoms of said aryl, heteroaryl or heterocyclyl ring optionally being replaced with a carbonyl group;

D is aryl optionally substituted by one, two or three halogen atoms independently selected from chlorine, fluorine and bromine or heteroaryl optionally substituted by one, two or three halogen atoms independently selected from chlorine, fluorine and bromine;

E is E-1:

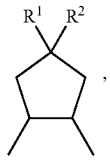

E-2:

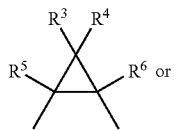

E-3:

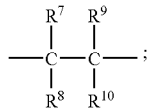

$R^1$ and $R^2$ are independently from each other hydrogen, halogen, $C_{1-6}$ alkyl, $C_{3-7}$ cycloalkyl, $C_{3-7}$ cycloalkyl $C_{1-6}$ alkyl, amino, mono-substituted amino, di-substituted amino, hydroxy, $C_{1-6}$ alkoxy, mono-substituted amino-$C_{1-6}$ alkyl, di-substituted amino-$C_{1-6}$ alkyl, hydroxyl $C_{1-6}$ alkyl or $R^1$ and $R^2$ together form

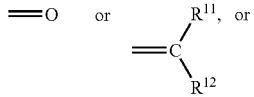

$R^1$ and $R^2$ are bonded to each other to form optionally substituted heterocyclyl, together with the carbon atom to which $R^1$ and $R^2$ are attached;

$R^3$ and $R^4$ are independently from each other hydrogen, $C_{1-6}$ alkyl, carboxyl, $C_{1-6}$ alkoxycarbonyl, carbamoyl, mono- or di-substituted amino-carbonyl, optionally substituted aryl carbonyl, optionally substituted heterocyclylcarbonyl, optionally substituted heteroarylcarbonyl, optionally substituted aryl, optionally substituted heteroaryl, optionally substituted heterocyclyl, hydroxyl $C_{1-6}$ alkyl, halo $C_{1-6}$ alkyl, cyano $C_{1-6}$ alkyl, $C_{1-6}$ alkoxy $C_{1-6}$ alkyl, amino $C_{1-6}$ alkyl, mono- or di-substituted amino-$C_{1-6}$ alkyl, optionally substituted aryl $C_{1-6}$ alkyl, optionally substituted heterocyclyl $C_{1-6}$ alkyl, optionally substituted heteroaryl $C_{1-6}$ alkyl, optionally substituted aryl $C_{1-6}$ alkoxy $C_{1-6}$ alkyl, optionally substituted heteroaryl $C_{1-6}$ alkoxy $C_{1-6}$ alkyl, optionally substituted heterocyclyl $C_{1-6}$ alkoxy $C_{1-6}$ alkyl or $R^3$ and $R^4$ are bonded to each other to form $C_{3-7}$ cycloalkyl, together with the carbon atom to which $R^3$ and $R^4$ are attached;

$R^5$ and $R^6$ are independently from each other hydrogen, $C_{1-6}$ alkyl, cyano, $C_{1-6}$ alkoxycarbonyl, $C_{2-6}$ alkenyloxycarbonyl, $C_{2-6}$ alkynyloxycarbonyl, hydroxyl $C_{1-6}$ alkyl, $C_{1-6}$ alkoxycarbonyl, carboxyl, mono- or di-$C_{1-6}$ alkyl substituted amino-carbonyl, aminocarbonyl, optionally substituted heterocyclyl carbonyl, optionally substituted heteroaryl carbonyl or optionally substituted aryl carbonyl;

$R^7$, $R^8$, $R^9$ and $R^{10}$ are independently from each other hydrogen, $C_{1-6}$ alkyl or hydroxy;

$R^{11}$ and $R^{12}$ are independently from each other hydrogen, $C_{1-6}$ alkyl or $C_{2-6}$ alkenyl;

and pharmaceutically acceptable salts thereof.

Preferably $R^3$ and $R^4$ are independently from each other hydrogen, $C_{1-6}$ alkyl, carboxyl, $C_{1-6}$ alkoxycarbonyl, carbamoyl, mono- or di-substituted amino-carbonyl, optionally substituted heterocyclylcarbonyl, optionally substituted heteroarylcarbonyl, aryl, optionally substituted heteroaryl, optionally substituted heterocyclyl, hydroxyl $C_{1-6}$ alkyl, $C_{1-6}$ alkoxy $C_{1-6}$ alkyl, amino $C_{1-6}$ alkyl, mono- or di-substituted amino-$C_{1-6}$ alkyl, optionally substituted heterocyclyl $C_{1-6}$ alkyl, optionally substituted heteroaryl $C_{1-6}$ alkyl or $R^3$ and $R^4$ are bonded to each other to form $C_{3-7}$ cycloalkyl, together with the carbon atom to which $R^3$ and $R^4$ are attached and $R^5$ and $R^6$ are independently from each other hydrogen or $C_{1-6}$ alkyl.

More preferably $R^3$ and $R^4$ are independently from each other hydrogen, $C_{1-6}$ alkyl, carboxyl, $C_{1-6}$ alkoxycarbonyl, mono- or di-substituted amino-carbonyl, optionally substituted heterocyclylcarbonyl, aryl, optionally substituted heteroaryl, optionally substituted heterocyclyl, hydroxyl $C_{1-6}$ alkyl, $C_{1-6}$ alkoxy $C_{1-6}$ alkyl, amino $C_{1-6}$ alkyl, mono- or di-substituted amino-$C_{1-6}$ alkyl, optionally substituted heterocyclyl $C_{1-6}$ alkyl, optionally substituted heteroaryl $C_{1-6}$ alkyl or $R^3$ and $R^4$ are bonded to each other to form $C_{3-7}$ cycloalkyl, together with the carbon atom to which $R^3$ and $R^4$ are attached.

While the broadest definition of this invention is described before, certain compounds of Formula (I) are preferred.

A preferred compound of the invention is a compound of Formula (I) wherein E is E-1. When E is E-1, D is preferably aryl optionally substituted by one halogen atom selected from chlorine and bromine or heteroaryl optionally substituted by one halogen atom selected from chlorine and bromine. More preferred halogen atom is chlorine. Aryl group for D is preferably phenyl. Heteroaryl group for D is preferably monocyclic or bicyclic radical of 5 to 12 ring atoms having at least one aromatic ring containing one or two ring heteroatoms selected from N and S, such as pyrrolyl, pyridyl, pyridazinyl, pyrimidinyl, pyrazinyl, pyrazolyl, imidazolyl, tetrazolyl, thienyl, isothiazolyl, indolyl, isoindolyl, indolizinyl, indazolyl, quinolyl, isoquinolyl, more preferably pyridyl, thienyl, pyrimidinyl, pyridazinyl or indolyl, especially phenyl or pyridyl.

When E is E-1, D is further more preferably chlorophenyl or chloropyridyl, especially 4-chlorophenyl or 5-chloro-pyridin-2-yl. 4-chlorophenyl is especially preferred.

When E is E-1, B is preferably optionally substituted phenyl or optionally substituted heteroaryl. Heteroaryl group for B is preferably a monocyclic radical of five or six ring atoms having one or two ring nitrogen atoms, such as pyridyl, pyridazinyl, pyrimidinyl, pyrazinyl, pyrazolyl, imidazolyl, pyrrolyl, especially pyridyl. B is more preferably phenyl or pyridyl, especially phenyl, optionally substituted by one or two halogen atoms selected independently from the group consisting of chlorine, fluorine and bromine. Further more preferred group for B is a phenyl substituted by one or two fluorine, especially one fluorine. 2-fluorophenyl is especially preferred.

When E is E-1, $R^c$ is preferably aryl, heteroaryl or heterocyclyl, one carbon atom of said aryl, heteroaryl or heterocyclyl ring optionally being replaced with a carbonyl group, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl, more preferably $R^c$ is aryl, heteroaryl or heterocyclyl, one carbon atom of said aryl, heteroaryl or heterocyclyl ring being replaced with a carbonyl group at ortho position with respect to B, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl. Aryl group for $R^c$ is preferably phenyl. Heteroaryl group for $R^c$ is preferably a monocyclic radical of five or six ring atoms having one or two ring nitrogen atoms, such as pyridyl, pyridazinyl, pyrimidinyl, pyrazinyl, pyrazolyl, imidazolyl, pyrrolyl, more preferably pyridyl, imidazolyl, pyrazinyl, especially pyridyl. Heterocyclyl group for $R^c$ is preferably pyrrolidinyl, pyrrolinyl, imidazolidinyl, imidazolinyl, pyrazolidinyl, pyrazolinyl, piperidyl, piperazinyl, morpholinyl, pyranyl, tetrahydropyranyl, 4,5-dihydro-oxazolyl, sultamyl or 4,5-dihydro-thiazolyl, more preferably morpholinyl, piperidyl or sultamyl. Further preferred group for $R^c$ is 2-oxo-2H-pyridin-1-yl optionally substituted by $C_{1-6}$ alkyl or $C_{1-6}$ alkoxy, especially 2-oxo-2H-pyridin-1-yl.

Especially preferred —B—$R^c$ is 2-fluoro-4-(2-oxo-2H-pyridin-1-yl)-phenyl.

When E is E-1, preferably $R^1$ and $R^2$ are independently from each other hydrogen, hydroxy, $C_{1-6}$ alkoxy, hydroxy $C_{1-6}$ alkyl or $R^1$ and $R^2$ together form

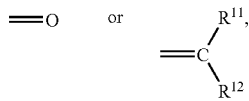

or $R^1$ and $R^2$ are bonded to each other to form optionally substituted heterocyclyl, together with the carbon atom to which $R^1$ and $R^2$ are attached. More preferably $R^1$ and $R^2$ are independently from each other hydrogen, hydroxy, $C_{1-6}$ alkoxy, hydroxy $C_{1-6}$ alkyl or $R^1$ and $R^2$ together form

in which $R^{11}$ and $R^{12}$ are hydrogen, or $R^1$ and $R^2$ are bonded to each other to form

together with the carbon atom to which $R^1$ and $R^2$ are attached. Especially $R^1$ and $R^2$ together form

in which $R^{11}$ and $R^{12}$ are hydrogen.

When E is E-1, A is preferably —CONH—.

When E is E-1, the compounds wherein —B—$R^c$ is 2-fluoro-4-(2-oxo-2H-pyridin-1-yl)-phenyl, D is 4-chlorophenyl and A is preferably —CONH— are especially preferred.

Particularly preferred compounds in this group are:

(1S,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide}, (1R,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide}, (1S,2S,4S)- or (1S,2S,4R)-4-Hydroxymethyl-4-methoxy-cyclopentane-1,2-dicarboxylic acid 1-[(4-chloro-phenyl)-amide]2-{[2-fluoro-4-(2-oxo-2H-pyridin-1-yl)-phenyl]-amide}, (5S,6S)-Spiro[2.4]heptane-5,6-dicarboxylic acid (4-chloro-phenyl)-amide[2-fluoro-4-(2-oxo-2H-pyridin-1-yl)-phenyl]-amide, (1S,2S,4S)-4-Fluoro-cyclopentane-1,2-dicarboxylic acid 1-[(4-chloro-phenyl)-amide]2-{[2-fluoro-4-(2-oxo-2H-pyridin-1-yl)-phenyl]-amide}, (1S,2S,4R)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide}, (1S,2S,4S)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide}.

Other particularly preferred compounds in this group are:

(1S,2S,4S)-4-fluoro-cyclopentane-1,2-dicarboxylic acid 1-[(4-chloro-phenyl)-amide]2-{[2-fluoro-4-(2-oxo-2H-pyridin-1-yl)-phenyl]-amide}, (1S,2S,4R)-4-fluoro-cyclopentane-1,2-dicarboxylic acid 1-[(5-chloro-pyridin-2-yl)-amide]2-{[2-fluoro-4-(2-oxo-2H-pyridin-1-yl)-phenyl]-amide}, (1S,2S,4R)-4-fluoro-cyclopentane-1,2-dicarboxylic acid 1-[(5-chloro-pyridin-2-yl)-amide]2-{[2-fluoro-4-(2-oxo-2H-pyrazin-1-yl)-phenyl]-amide}, ((1S,2S,4R)-4-fluoro-cyclopentane-1,2-dicarboxylic acid 1-[(5-chloro-pyridin-2-yl)-amide]2-{[4-(3-oxo-morpholin-4-yl)-phenyl]-amide}), (1S,2S,4R)-4-Fluoro-cyclopentane-1,2-dicarboxylic acid 1-[(5-chloro-pyridin-2-yl)-amide]2-{[2-fluoro-4-(3-oxo-morpholin-4-yl)-phenyl]-amide}.

Another preferred compound of the invention is a compound of Formula (I) wherein E is E-2.

When E is E-2, D is preferably aryl optionally substituted by one halogen atom selected from chlorine and bromine or heteroaryl optionally substituted by one halogen atom selected from chlorine and bromine. More preferred halogen atom is chlorine. Aryl group for D is preferably phenyl. Heteroaryl group for D is preferably monocyclic or bicyclic radical of 5 to 12 ring atoms having at least one aromatic ring containing one or two ring heteroatoms selected from N and S, such as pyrrolyl, pyridyl, pyridazinyl, pyrimidinyl, pyrazinyl, pyrazolyl, imidazolyl, tetrazolyl, thienyl, isothiazolyl, indolyl, isoindolyl, indolizinyl, indazolyl, quinolyl, isoquinolyl, more preferably pyridyl, thienyl, pyrimidinyl, pyridazinyl or indolyl, especially phenyl or pyridyl.

When E is E-2, D is further more preferably chlorophenyl or chloropyridyl, especially 4-chlorophenyl or 5-chloro-pyridin-2-yl. 4-chlorophenyl is especially preferred.

When E is E-2, B is preferably optionally substituted phenyl or optionally substituted heteroaryl. Heteroaryl group for B is preferably a monocyclic radical of five or six ring atoms having one or two ring nitrogen atoms, such as pyridyl, pyridazinyl, pyrimidinyl, pyrazinyl, pyrazolyl, imidazolyl, pyrrolyl, especially pyridyl. B is more preferably phenyl or pyridyl, especially phenyl, optionally substituted by one or two halogen atoms selected independently from the group consisting of chlorine, fluorine and bromine. Further more preferred group for B is a phenyl substituted by one or two fluorine, especially one fluorine. 2-fluorophenyl is especially preferred.

When E is E-2, $R^c$ is preferably aryl, heteroaryl or heterocyclyl, one carbon atom of said aryl, heteroaryl or heterocyclyl ring optionally being replaced with a carbonyl group, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, aminocarbonyl $C_{1-6}$ alkoxy, mono- or di-substituted aminocarbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy or carboxyl $C_{1-6}$ alkoxy, preferably said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl. More preferably $R^c$ is aryl, heteroaryl or heterocyclyl, one carbon atom of said aryl, heteroaryl or heterocyclyl ring being replaced with a carbonyl group at ortho position with respect to B, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl. Aryl group for $R^c$ is preferably phenyl. Heteroaryl group for $R^c$ is preferably a monocyclic radical of five or six ring atoms having one or two ring nitrogen atoms, such as pyridyl, pyridazinyl, pyrimidinyl, pyrazinyl, pyrazolyl, imidazolyl, pyrrolyl, more preferably pyridyl, imidazolyl, pyrazinyl, especially pyridyl. Heterocyclyl group for $R^c$ is preferably pyrrolidinyl, pyrrolinyl, imidazolidinyl, imidazolinyl, pyrazolidinyl, pyrazolinyl, piperidyl, piperazinyl, morpholinyl, pyranyl, tetrahydropyranyl, 4,5-dihydro-oxazolyl, sultamyl or 4,5-dihydro-thiazolyl, more preferably morpholinyl, piperidyl or sultamyl. Further preferred group for $R^c$ is 2-oxo-2H-pyridin-1-yl optionally substituted by $C_{1-6}$ alkyl or $C_{1-6}$ alkoxy, especially 2-oxo-2H-pyridin-1-yl.

Especially preferred —B—$R^c$ is 2-fluoro-4-(2-oxo-2H-pyridin-1-yl)-phenyl.

When E is E-2, A is preferably —CONH—.

When E is E-2, preferably $R^3$ and $R^4$ are independently from each other hydrogen, $C_{1-6}$ alkoxycarbonyl or hydroxy $C_{1-6}$ alkyl.

When E is E-2, the compounds wherein $R^4$ is mono- or di-substituted amino-carbonyl are also preferred. The compounds wherein $R^4$ is di-substituted amino-carbonyl are more preferred. Preferred di-substituted amino-carbonyl for $R^4$ is —C(O)—NRR' wherein R is $C_{1-6}$ alkyl, especially methyl, and R' is hydroxy $C_{1-6}$ alkyl, especially 2-hydroxyethyl. When $R^4$ is mono- or di-substituted amino-carbonyl, $R^3$ is preferably hydrogen.

When E is E-2, the compounds wherein $R^4$ is optionally substituted heterocyclylcarbonyl or optionally substituted heteroarylcarbonyl are also preferred. The compounds wherein $R^4$ is optionally substituted heterocyclylcarbonyl are more preferred. Heterocyclyl group of "optionally substituted heterocyclylcarbonyl" contains preferably a nitrogen atom as a ring member, and the carbonyl carbon atom is bonded to the nitrogen atom of the heterocyclyl group. A preferred optionally substituted heterocyclylcarbonyl is, for example, morpholinyl, pyrrolidinyl, 3-hydroxypyrrolidinyl, piperidinyl, 3-hydroxypiperidinyl, 4-methylpiperazinyl, azetidinyl. When $R^4$ is optionally substituted heterocyclylcarbonyl or optionally substituted heteroarylcarbonyl, $R^3$ is preferably hydrogen.

When E is E-2, the compounds wherein —B—$R^c$ is 2-fluoro-4-(2-oxo-2H-pyridin-1-yl)-phenyl, D is 4-chlorophenyl or 5-chloro-pyridin-2-yl and A is —CONH— are preferred.

When E is E-2, the compounds wherein A is —CONH—, —B—$R^c$ is 2-fluoro-4-(2-oxo-2H-pyridin-1-yl)-phenyl, D is 4-chlorophenyl or 5-chloro-pyridin-2-yl and $R^3$ is hydrogen and $R^4$ is mono- or di-substituted amino-carbonyl, optionally substituted heterocyclylcarbonyl or optionally substituted heteroarylcarbonyl are especially preferred. $R^4$ is more preferably di-substituted amino-carbonyl or optionally substituted heterocyclylcarbonyl. Preferred di-substituted amino-carbonyl for $R^4$ is —C(O)—NRR' wherein R is $C_{1-6}$ alkyl, especially methyl, and R' is hydroxy $C_{1-6}$ alkyl, especially 2-hydroxyethyl. A preferred optionally substituted heterocyclylcarbonyl for $R^4$ is one containing a nitrogen atom as a ring member, and the carbonyl carbon atom is bonded to the nitrogen atom of the heterocyclyl group, such as morpholinyl, pyrrolidinyl, 3-hydroxypyrrolidinyl, piperidinyl, 3-hydroxypiperidinyl, 4-methylpiperazinyl, azetidinyl.

When E is E-2, the compounds of the following enantiomeric form are preferred,

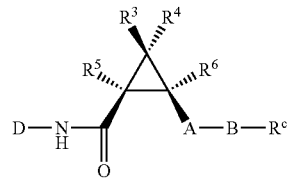

wherein A, B, $R^c$, D and $R^3$—$R^5$ are as defined before.

A is preferably —CONH—, —B—$R^c$ is preferably 2-fluoro-4-(2-oxo-2H-pyridin-1-yl)-phenyl, D is preferably 4-chlorophenyl or 5-chloro-pyridin-2-yl and $R^3$ is preferably hydrogen and $R^4$ is preferably mono- or di-substituted aminocarbonyl, optionally substituted heterocyclylcarbonyl or optionally substituted heteroarylcarbonyl.

Particularly preferred compounds in this group are:

(1RS,2SR)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}, (1RS,2SR)-1-methyl-cyclopropane-1,2-dicarboxylic acid 2-[(5-chloro-pyridin-2-yl)-amide]1-{[2-fluoro-4-(2-oxo-2H-pyridin-1-yl)-phenyl]-amide}, (1SR,2SR,3RS)-2-(4-chloro-phenylcarbamoyl)-3-[4-(2-oxo-2H-pyridin-1-yl)-phenylcarbamoyl]-cyclopropanecarboxylic acid ethyl ester, (1RS,2SR)-1-methyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}, (1SR,2RS,3SR)-3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2SR,3SR)-2-(4-Chloro-phenylcarbamoyl)-3-[4-(2-oxo-2H-pyridin-1-yl)-phenylcarbamoyl]-cyclopropanecarboxylic acid, (1SR,2RS,3SR)-3-(1-Hydroxy-1-methyl-ethyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2RS,3SR)-3-(1-Ethyl-1-hydroxy-propyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3RS)-3-(Piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-Cyclopropane-1,2,3-tricarboxylic acid 1-[(4-chloro-phenyl)-amide]2-dimethylamide 3-{[2-fluoro-4-(2-oxo-2H-pyridin-1-yl)-phenyl]-amide}, (1RS,2SR,3SR)-Cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-hydroxy-ethyl)-methyl-amide], (1SR,2RS,3SR)-2-(4-Chloro-phenylcarbamoyl)-3-[2-fluoro-4-(2-oxo-2H-pyridin-1-yl)-phenylcarbamoyl]-cyclopropanecarboxylic acid ethyl ester, (1SR,2RS,3SR)-2-(4-Chloro-phenylcarbamoyl)-3-[2-fluoro-4-(2-oxo-2H-pyridin-1-yl)-phenylcarbamoyl]-cyclopropanecarboxylic acid, (1S,2R,3S)-2-(4-Chloro-phenylcarbamoyl)-3-[2-fluoro-4-(2-oxo-2H-pyridin-1-yl)-phenylcarbamoyl]-cyclopropanecarboxylic acid ethyl ester, (1S,2R,3S)-2-(4-Chloro-phenylcarbamoyl)-3-[2-fluoro-4-(2-oxo-2H-pyridin-1-yl)-phenylcarbamoyl]-cyclopropanecarboxylic acid, (1RS,2SR,3SR)-3-(Morpholine-4-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1R,2S,3S)-3-(Morpholine-4-carbonyl)-cyclopropane-1,2-dicarboxylic acid 1-[(4-chlorophenyl)-amide]2-{[2-fluoro-4-(2-oxo-2H-pyridin-1-yl)-phenyl]-amide}, (1RS,2SR,3SR)-3-(3-Hydroxy-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2SR,3RS)-Cyclopropane-1,2,3-tricarboxylic acid 1-amide 2-[(4-chloro-phenyl)-amide]3-{[2-fluoro-4-(2-oxo-2H-pyridin-1-yl)-phenyl]-amide}, (1RS,2SR,3SR)-Cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-methoxy-ethyl)-methyl-amide], (1SR,2RS,3SR)-Cyclopropane-1,2,3-tricarboxylic acid 1-(carbamoylmethyl-methyl-amide)2-[(4-chloro-phenyl)-amide]3-{[2-fluoro-4-(2-oxo-2H-pyridin-1-yl)-phenyl]-amide}, (1RS,2SR,3SR)-3-(Azepane-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-3-(3-Oxo-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-3-(3,3-Difluoro-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2SR,3RS)-Cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2,2,2-trifluoro-ethyl)-amide], (1RS,2SR,3SR)-Cyclopropane-1,2,3-tricarboxylic acid 1-[(4-chloro-phenyl)-amide]2-diethylamide 3-{[2-fluoro-4-(2-oxo-2H-pyridin-1-yl)-phenyl]-amide}, (1RS,2SR,3SR)-3-(Pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-3-(Azetidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2SR,3RS)-Cyclopropane-1,2,3-tricarboxylic acid 1-[(4-chloro-phenyl)-amide]2-ethylamide 3-{[2-fluoro-4-(2-oxo-2H-pyridin-1-yl)-phenyl]-amide}, (1SR,2SR,3RS)-Cyclopropane-1,2,3-tricarboxylic acid 1-[(4-chloro-phenyl)-amide]2-[(2,2-difluoro-ethyl)-amide]3-{[2-fluoro-4-(2-oxo-2H-pyridin-1-yl)-phenyl]-amide}, (1RS,2SR,3SR)-3-(3-Hydroxy-azetidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-3-(3-Hydroxy-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-Cyclopropane-1,2,3-tricarboxylic acid 1-[(4-chloro-phenyl)-amide]2-[(2,3-dihydroxy-propyl)-methyl-amide]3-{[2-fluoro-4-(2-oxo-2H-pyridin-1-yl)-phenyl]-amide}, (1RS,2SR,3SR)-3-(4-Hydroxy-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-3-(4-Methyl-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-Cyclopropane-1,2,3-tricarboxylic acid 1-[(4-chloro-phenyl)-amide]2-[(2-dimethylamino-ethyl)-methyl-amide]3-{[2-fluoro-4-(2-oxo-2H-pyridin-1-yl)-phenyl]-amide}, (1RS,2SR,3RS)-3-(4-Acetyl-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-3-(4-Dimethylamino-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-3-(4-Carbamoyl-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}, (1RS,2SR,3SR)-Cyclopropane-1,2,3-tricarboxylic acid 1-[(4-chloro-phenyl)-amide]2-(dimethylcarbamoylmethyl-methyl-amide) 3-{[2-fluoro-4-(2-oxo-2H-pyridin-1-yl)-phenyl]-amide}, (1R,2S,3S)-Cyclopropane-1,2,3-tricarboxylic acid 1-[(4-chloro-phenyl)-amide]2-dimethylamide 3-{[2-fluoro-4-(2-oxo-2H-pyridin-1-yl)-phenyl]-amide}, (1R,2S,3S)-Cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-hydroxy-ethyl)-methyl-amide].

Particularly preferred compounds in this group are:

(1S,2R,3S)-3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1S,2R,3S)-3-pyrrolidin-1-ylmethyl-cyclopropane-1,2-dicarboxylic acid 1-[(4-chlorophenyl)-amide]2-{[2-fluoro-4-(2-oxo-2H-pyridin-1-yl)-phenyl]-amide}, (1S,2R,3S)-3-cyanomethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1S,2R,3S)-3-methoxymethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2RS)-1-cyano-cyclopropane-1,2-dicarboxylic acid 1-[(5-chloro-pyridin-2-yl)-amide]2-{[2-fluoro-4-(2-oxo-2H-pyridin-1-yl)-phenyl]-amide}, (1SR,2RS)-1-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2RS)-1-cyano-cyclopropane-1,2-dicarboxylic acid 2-[(5-chloro-pyridin-2-yl)-amide]1-{[2-fluoro-4-(2-oxo-2H-pyridin-1-yl)-phenyl]-amide}, (1SR,2RS)-1-hydroxymethyl-cyclopropane-1,2-dicarboxylic acid 2-[(4-chloro-phenyl)-amide]1-{[2-fluoro-4-(2-oxo-2H-pyridin-1-yl)-phenyl]-amide}, (1R,2S)-1-methyl-cyclopropane-1,2-dicarboxylic acid 2-[(5-chloro-pyridin-2-yl)-amide]1-{[2-fluoro-4-(2-oxo-pyridin-1-yl)-phenyl]-amide}, (1S,2R,3R)-3-hydroxymethyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}.

Another preferred compound of the invention is a compound of Formula (I) wherein E is E-3.

When E is E-3, D is preferably aryl optionally substituted by one halogen atom selected from chlorine and bromine or heteroaryl optionally substituted by one halogen atom selected from chlorine and bromine. More preferred halogen atom is chlorine. Aryl group for D is preferably phenyl. Heteroaryl group for D is preferably monocyclic or bicyclic radical of 5 to 12 ring atoms having at least one aromatic ring containing one or two ring heteroatoms selected from N and S, such as pyrrolyl, pyridyl, pyridazinyl, pyrimidinyl, pyrazinyl, pyrazolyl, imidazolyl, tetrazolyl, thienyl, isothiazolyl, indolyl, isoindolyl, indolizinyl, indazolyl, quinolyl, isoquinolyl, more preferably pyridyl, thienyl, pyrimidinyl, pyridazinyl or indolyl, especially phenyl or pyridyl.

When E is E-3, D is further more preferably chlorophenyl or chloropyridyl, especially 4-chlorophenyl or 5-chloro-pyridin-2-yl. 4-chlorophenyl is especially preferred.

When E is E-3, B is preferably optionally substituted phenyl or optionally substituted heteroaryl. Heteroaryl group for B is preferably a monocyclic radical of five or six ring atoms having one or two ring nitrogen atoms, such as pyridyl, pyridazinyl, pyrimidinyl, pyrazinyl, pyrazolyl, imidazolyl, pyrrolyl, especially pyridyl. B is more preferably phenyl or pyridyl, especially phenyl, optionally substituted by one or two halogen atoms selected independently from the group consisting of chlorine, fluorine and bromine. Further more preferred group for B is a phenyl substituted by one or two fluorine, especially one fluorine. 2-fluorophenyl is especially preferred.

When E is E-3, $R^c$ is preferably aryl, heteroaryl or heterocyclyl, one carbon atom of said aryl, heteroaryl or heterocyclyl ring optionally being replaced with a carbonyl group, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl, more preferably $R^c$ is aryl, heteroaryl or heterocyclyl, one carbon atom of said aryl, heteroaryl or heterocyclyl ring being replaced with a carbonyl group at ortho position with respect to B, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl. Aryl group for $R^c$ is preferably phenyl. Heteroaryl group for $R^c$ is preferably a monocyclic radical of five or six ring atoms having one or two ring nitrogen atoms, such as pyridyl, pyridazinyl, pyrimidinyl, pyrazinyl, pyrazolyl, imidazolyl, pyrrolyl, more preferably pyridyl, imidazolyl, pyrazinyl, especially pyridyl. Heterocyclyl group for $R^c$ is preferably pyrrolidinyl, pyrrolinyl, imidazolidinyl, imidazolinyl, pyrazolidinyl, pyrazolinyl, piperidyl, piperazinyl, morpholinyl, pyranyl, tetrahydropyranyl, 4,5-dihydro-oxazolyl, sultamyl or 4,5-dihydro-thiazolyl, more preferably morpholinyl, piperidyl or sultamyl. Further preferred group for $R^c$ is 2-oxo-2H-pyridin-1-yl optionally substituted by $C_{1-6}$ alkyl or $C_{1-6}$ alkoxy, especially 2-oxo-2H-pyridin-1-yl.

Especially preferred —B—$R^c$ is 2-fluoro-4-(2-oxo-2H-pyridin-1-yl)-phenyl.

When E is E-3, A is preferably —CONH—.

When E is E-3, the compounds wherein —B—$R^c$ is 2-fluoro-4-(2-oxo-2H-pyridin-1-yl)-phenyl, D is 4-chlorophenyl and A is preferably —CONH— are especially preferred.

Particularly preferred compounds in this group are:

N1-(4-Chloro-phenyl)-N-4-[2-fluoro-4-(2-oxo-2H-pyridin-1-yl)-phenyl]-succinamide, N4-(4-Chloro-phenyl)-N1-[2-fluoro-4-(2-oxo-2H-pyridin-1-yl)-phenyl]-2,2-dimethyl-succinamide, (4-Chloro-phenyl)-3,3-dimethyl-4-[4-(1-methyl-piperidin-4-yl)-piperazin-1-yl]-4-oxo-butyramide, (R)—N4-(4-Chloro-phenyl)-N1-[2-fluoro-4-(2-oxo-2H-pyridin-1-yl)-phenyl]-2-hydroxy-succinamide, (4-chloro-phenyl)-[2-fluoro-4-(3-oxo-morpholin-4-yl)-phenyl]-2,2-dimethyl-succinamide, (S)-(4-Chloro-phenyl)-[2-fluoro-4-(2-oxo-pyridin-1-yl)-phenyl]-2-hydroxy-2-methyl-succinamide, (R)—N1-(4-Chloro-phenyl)-N4-[2-fluoro-4-(2-oxo-2H-pyridin-1-yl)-phenyl]-2-hydroxy-succinamide, (S)—N1-(4-Chloro-phenyl)-N4-[2-fluoro-4-(2-oxo-2H-pyridin-1-yl)-phenyl]-2-hydroxy-succinamide, (R)-(4-Chloro-phenyl)-[2-fluoro-4-(2-oxo-pyridin-1-yl)-phenyl]-2-hydroxy-2-methyl-succinamide, (S)—N4-(4-Chloro-phenyl)-N1-[2-fluoro-4-(2-oxo-2H-pyridin-1-yl)-phenyl]-2-hydroxy-succinamide.

Also within the scope of the present invention are intermediate compounds, for example, an enantiomerically pure compound with formula

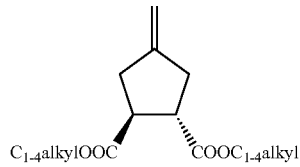

or compounds with the formula

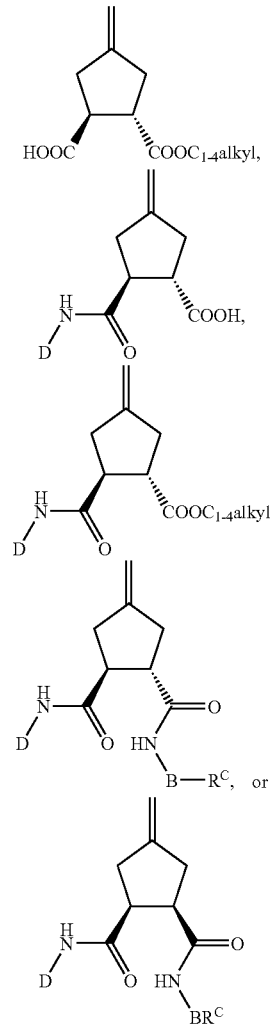

wherein

B is optionally substituted phenyl, optionally substituted heteroaryl or optionally substituted heterocyclyl;

$R^c$ is optionally substituted aryl, optionally substituted heteroaryl or optionally substituted heterocyclyl, one or two carbon atoms of said aryl, heteroaryl or heterocyclyl ring optionally being replaced with a carbonyl group; and D is aryl optionally substituted by one, two or three halogen atoms independently selected from chlorine, fluorine and bromine or heteroaryl optionally substituted by one, two or three halogen atoms independently selected from chlorine, fluorine and bromine.

The compounds of the present invention can be prepared, for example, by the general synthetic procedures described below.

General Synthetic Procedures

Abbreviations:

BOP: Benzotriazolyl-N-oxy-tris(dimethylamino)-phosphonium hexafluorophosphate

BOP-Cl: Bis-(2-oxo-3-oxazolidinyl)-phosphinic acid chloride

CDI: Carbonyldiimidazole

DCC: N,N'-Dicyclohexylcarbodiimide

DIC: N,N'-Diisopropylcarbodiimide

DMA: N,N-Dimethylacetamide

DMF: N,N-Dimethylformamide

EDC: N-(3-Dimetylaminopropyl)-N'-ethyl-carbodiimide hydrochloride

EEDQ: N-Ethoxycarbonyl-2-ethoxy-1,2-dihydroquinoline

HATU: O-(7-Azabenzotriazol-1-yl)-N,N,N',N'-tetramethyluronium hexafluorophosphate HBTU: O-(Benzotriazol-1-yl)-N,N,N',N'-tetramethyluronium hexafluorophosphate HOBt: N-Hydroxybenzotriazole MCPBA: m-Chloroperbenzoic acid NMP: N-methylpyrrolidone PyBOP: Benzotriazol-1-yl-oxytripyrrolidinephosphonium hexafluorophosphate PyBrOP: Brom-tripyrrolidinophosphonium hexafluorophosphate TBTU: O-(Benzotriazol-1-yl)-N,N,N',N'-tetramethyluronium terafluoroborate THF: Tetrahydrofurane 1. Synthesis of Cyclopentane Dicarboxamide Derivatives (Racemic)

a) Synthesis of Key Intermediates Trans- and Cis-Ketones and Epoxides

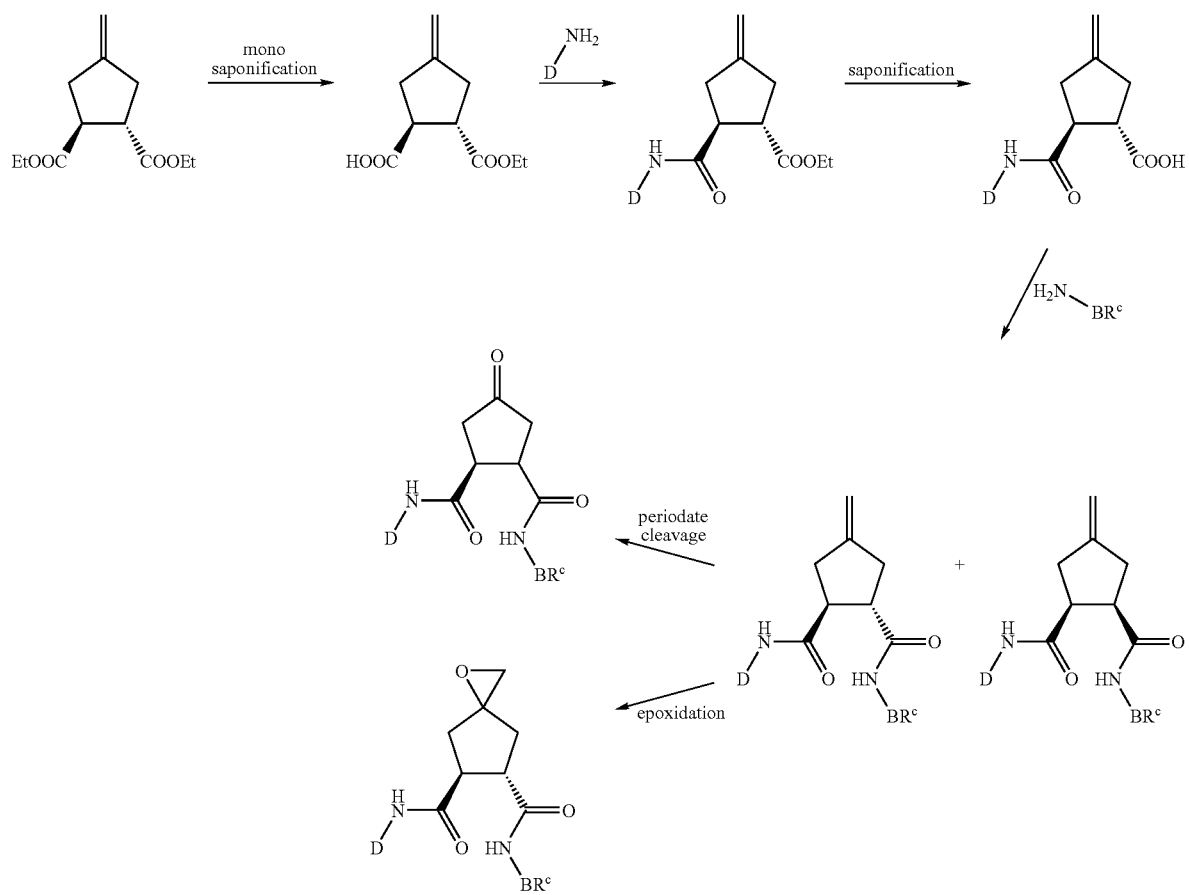

The mono saponification of methylene-cyclopentane-1,2-dicarboxylic acid diethyl ester (available by the method decribed by B. M. Trost et al., J. Am. Chem. Soc., 105, 2315, 1983) can be effected by dissolving it in a suitable solvent like MeOH, EtOH, THF, 1,4-dioxane, water or mixtures thereof and a base like LiOH, NaOH, KOH, $Na_2CO_3$, $K_2CO_3$ or $Cs_2CO_3$, preferably MeOH and $K_2CO_3$.

The mono acid is dissolved in a suitable solvent like dichloromethane, DMF, acetonitrile, THF, NMP, DMA, etc. and activated with an amide coupling reagent like EDC, DIC, DCC, CDI, TBTU, HBTU, EEDQ, HOBt, HATU, PyBOP, PyBrOP, BOP, BOP-Cl, etc. in the presence of a base like $NEt_3$, hünigs base, N-methylmorpholine etc. at −20° C. to 120° C. By adding one to two equivalents of the amine D-$NH_2$ the corresponding monoamide is obtained after reaction for 0.5-120 h at −20° C. to 120° C. Alternatively, transformation of the acid into the corresponding acid chloride or anhydride by means of oxalyl chloride, thionylchloride, isobutylcarbamoyl chloride or related reagents and a base like $NEt_3$, hünigs base, N-methylmorpholine etc, and reaction with $D-NH_2$ (all $D-NH_2$ commercially available) yields also the corresponding monoamide. The preferred conditions involve THF, EDC, HOBt and $NEt_3$.

Saponification of the ester group can be effected as described above. The second amide group can be introduced as described above using $R^c$—B—$NH_2$, the preferred method involves isobutylcarbamoyl chloride as activating agent and N-methylmorpholine as base at −20 to 60° C. The trans- and cis-isomers can be separated by chromatography on silica.

Preparation of the aniline derivative $R^c$—B—$NH_2$ can be carried out according to the method described by C. F. Bigge et al. (patent application WO 2003045912).

Conversion of the olefine to the ketone group by periodate cleavage can be accomplished under standard conditions using $OsO_4$ and $NaIO_4$ in a solvent like an alcohol e.g. MeOH and water at 0° to 70° C. preferably at 20° C. for 1 to 20 h.

Epoxidation of the olefine can be accomplished with an oxidizing agent such as peracids, e.g. MeCOOOH or MCPBA in a solvent like e.g. $CH_2Cl_2$ at 0 to 50° C., preferably at 20° C. to give a mixture of epimers which can be separated by chromatography on silica.

b) Modifications of the Trans- and Cis-Ketones

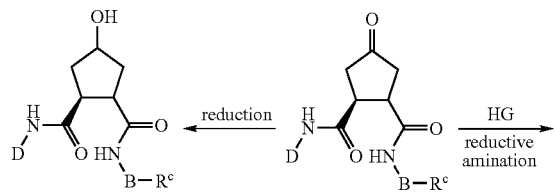

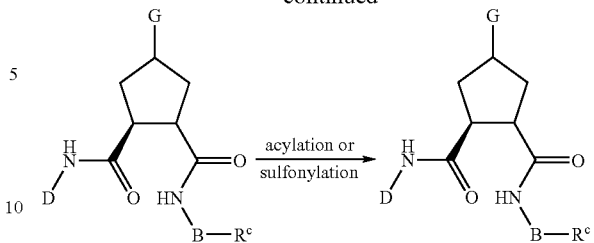
-continued

G in the scheme is mono or di-substituted amino as defined before. Reductive amination of the ketone with HG (all bases commercially available) can be accomplished with a reducing agent such as e.g. $NaBH_4$, $LiBH_4$, $Li(CN)BH_3$ or preferably $Na(CN)BH_3$ in a solvent such as an alcohol, e.g. MeOH or an ether, e.g. THF and an acid e.g. HCl, $H_2SO_4$, $H_3PO_4$ or a carboxylic acid, preferably $CH_3COOH$ at a temperature of −10 to 60° C., preferably at 20° C. for 1-40 h. The products obtained consist of a mixture of epimers at the newly formed stereo center.

Acylation and sulfonylation can be performed by reaction of the amine with a chloroformate, nitrophenylformate or a sulfochloride in the presence of a base, e.g. $NEt_3$ or preferably N,N-diisopropylethylamine in a solvent such as e.g. THF, $CH_2Cl_2$ or preferably $CH_3CN$ at −10 to 60° C., preferably at 20° C. for 1-40 h. The products obtained consist of a mixture of epimers at the G stereo center.

Reduction of the ketone to the alcohol can be effected by reducing agents e.g. $Li(CN)BH_3$, $Na(CN)BH_3$, $LiBH_4$ or preferably $NaBH_4$ in a solvent such as e.g. MeOH or preferably THF at a temperature of −10 to 60° C., preferably at 20° C. for 1-40 h. The products obtained consist of a mixture of epimers at the newly formed stereo center.

c) Modifications of the Trans-Epoxide

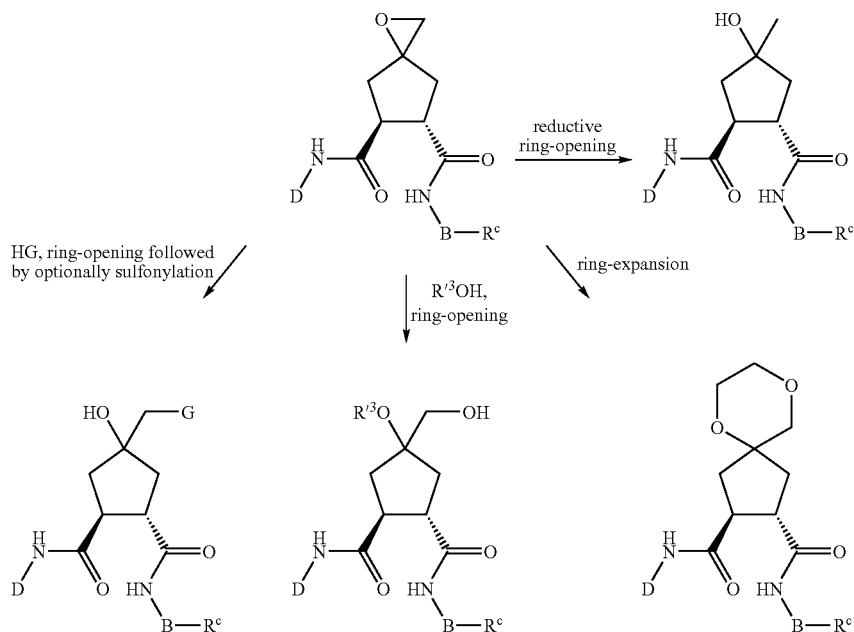

G in the scheme is mono- or di-substituted amino as defined before. $R^{t3}$ is hydrogen or $C_{1-6}$ alkyl.

Ring-opening of the epoxide with HG can be accomplished in an alcohol as solvent such as MeOH, EtOH, PrOH etc., preferably EtOH at a temperature of 20 to 120° C. for 1-40 h. Sulfonylation of the amines can be performed as described above. The products obtained consist of a mixture of epimers at the alcohol stereo center.

Ring-opening of the epoxide with $R^{t3}OH$, particularly $R^{t3}$=H can be effected in the presence of a mineral acid such as HCl, $H_2SO_4$, $H_3PO_4$ or a carboxylic acid, e.g. $CH_3COOH$, preferably $H_2SO_4$ in a solvent mixture such as THF/water at 0 to 100° C., preferably at 20° C. for 1 to 40 h. For $R^{t3}$=$C_{1-6}$ alkyl the reaction can be performed in the presence of a Lewis acid e.g. $BF_3.OEt_2$ using the alcohol $R^{t3}OH$ as the solvent at 0 to 100° C., preferably at 20° C. for 1 to 40 h. The products obtained consist of a mixture of epimers at the alcohol stereo center.

Ring-expansion of the epoxide can be accomplished with 2-chloroethanol as $R^{t3}OH$ in the presence of $BF_3.OEt_2$ as described above followed by cyclization of the intermediate chloroalcohol using KI as activating agent and a strong base such as LiOH, NaOH, KOH, preferably NaOH in a solvent mixture of $CH_3CN$ and water at 50 to 150° C. in a microwave apparatus. The products obtained consist of a mixture of epimers at the ether stereo center.

Reductive ring-opening of the epoxide can be effected according to A. Heydari et al. (Synthesis, 10, 1563, 2004) with a reducing agent such as $BH_3$ or preferably $BH_3.NEt_3$ in the presence of a promoter such as $LiClO_4$ in $Et_2O$ as the solvent at 0 to 50° C., preferably at 20° C. for 1-40 h. The products obtained consist of a mixture of epimers at the alcohol stereo center.

d) Modifications of the Amide Group

Curtius rearrangement (step i) of methylene-cyclopentane-1,2-dicarboxylic acid ethyl ester to the t-butyloxycarbonyl protected amine was accomplished with diphenylphosphoryl azide and an amine, e.g. $NEt_3$ in a solvent such as benzene or preferably toluene at 20 to 150° C., preferably at 80° C. for 1-40 h. The intermediate isocyanate can be trapped with an alcohol such as MeOH, EtOH or preferably t-BuOH at 20 to 150° C., preferably at 80 to 90° C.

Saponification (step ii) and amide formation (step iii) can be accomplished as described in the synthetic procedure 1a).

Deprotection (step iv) can be effected with a mineral acid such as HCl, $H_2SO_4$ or $H_3PO_4$ or a carbonic acid, preferably $CF_3COOH$ in a solvent such as $CH_2Cl_2$ at 0 to 60° C., preferably at 20° C. for 1-40 h.

Amide formation (step v) using $R^c$—B—COOH, which can be prepared according to the method described by C. F. Bigge et al. (patent application WO 2003045912) and steps vi-ix can be carried out as described in the synthetic procedures 1a) and 1b). The products obtained consist of a mixture of epimers at the newly formed stereo center.

Et in the schemes under procedure 1. a) to d) can be replaced with another $C_{1-6}$ alkyl group, preferably $C_{1-4}$ alkyl group. B, $R^c$ and D in the schemes under procedure I.a) to d) are as defined before. D is preferably 4-chloro phenyl. —B—$R^c$ is preferably 2-fluoro-4-(2-oxo-2H-pyridin-1-yl)-phenyl.

2. Synthesis of Cyclopentane Dicarboxamide Derivatives (Homochiral)

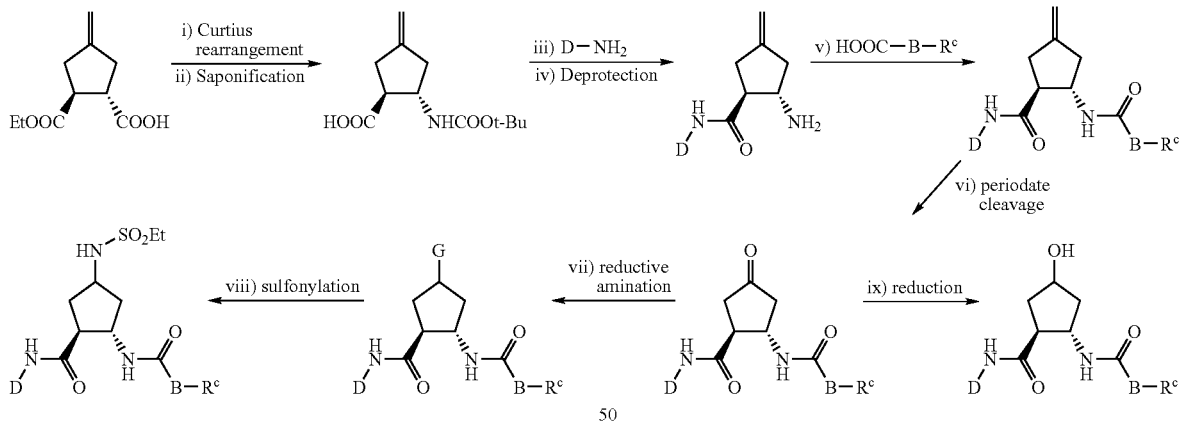

G in the scheme is mono or di-substituted amino as defined before.

a) Synthesis of Key Intermediates Trans-Ketones and Epoxides

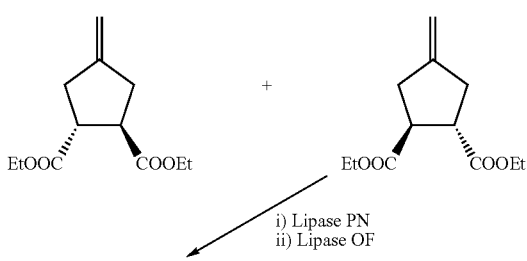

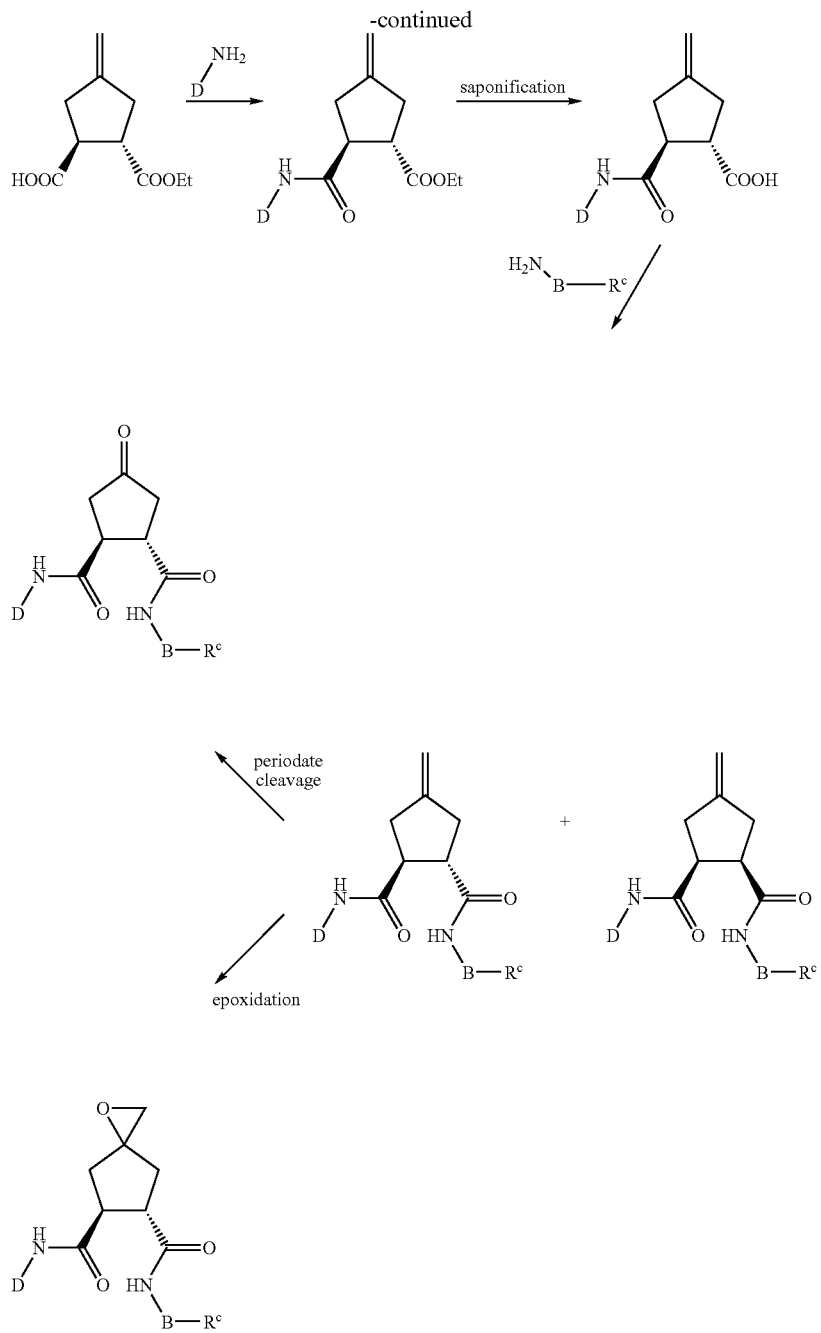

The resolution of racemic trans-methylene-cyclopentane-1,2-dicarboxylic acid diethyl ester via mono saponification can be accomplished with lipase PN from *Phycomyces nitens* to afford the enantiomerically pure S,S-diethyl ester as retained enantiomer.

The following selective mono saponification with lipase OF from *Candida rugosa* delivered the enantiomerically pure S,S-monoethyl ester. The used hydrolases were selected from a set of selective ones (like e.g. lipase G from *Penicilium camenberti*, lipase N from *Rhizopus niveus* or lipase PN from *Phycomyces nitens*) and active ones (like e.g. lipase OF from *Candida rugosa*, lipase RMM from *Rhizomucor miehei*, esterase PLE from pig liver or protease Subtilisin A from *Bacillus licheniformis*) discovered in a library out of 118 commercially available enzymes. Interestingly, the esterase from pig liver, which was used in a resolution of racemic trans-4-oxo-cyclopentane-1,2-dicarboxylic acid diethyl ester published by A. Rosenquist et al. (Acta Chem. Scan., 46, 1127, 1992), turned out to be not enantioselective for the resolution of racemic trans-methylene-cyclopentane-1,2-dicarboxylic acid diethyl ester.

Both enzymatic hydrolysis steps were performed as emulsion of the substrates in an aqueous buffer system. During the reaction the selected pH-value was maintained by controlled addition of a base. The selectivity and/or activity could be influenced by the addition of salts or organic solvents or by lowering the reaction temperature as shown in the preparative example. The work up of the products was achieved by conventional extractive procedures with different organic solvents at a proper pH-value.

Conversion of the mono acid to the ketone and epoxide epimers can be carried out as described in the synthetic procedures 1a)

b) Modifications of the Epoxide and Olefine

In a different strategy, modifications of the keto- and hydroxyl-group can be effected prior to the introduction of —B—$R^c$, since e.g. the intermediate epimers of the hydroxyester (only one epimer depicted in the scheme) can be conveniently separated.

Periodate cleavage of the olefine (step i) followed by reduction of the ketone (step ii) can be performed as described in

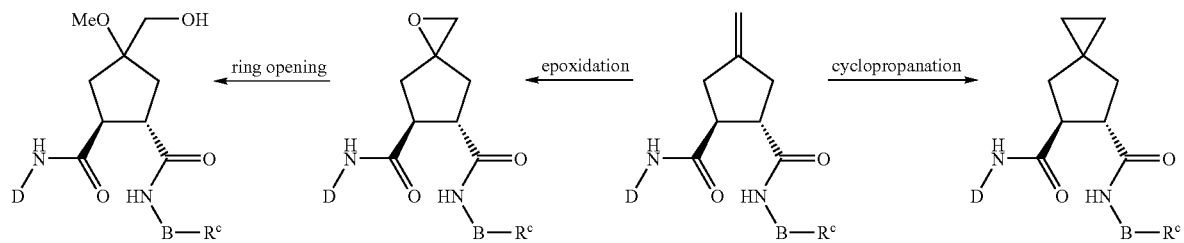

Ring opening of the epoxide can be effected as described in the synthetic procedure 1c). Both epimers are available as single isomer.

Cyclopropanation of the olefine can be carried out according to the method described by H. E. Simmons and R. D. Smith (J. Am. Chem. Soc. 80, 5323, 1958) involving diethylzinc, $CH_2I_2$ and trifluoroacetic acid in a solvent such as toluene or $CH_2Cl_2$ or a mixture thereof.

c) Modifications of the Intermediate Keto- and Hydroxyl-Esters the synthetic procedures 1a) and 1b). The hydroxyester epimers are separable by chromatography on silica.

Fluorination of the alcohol (step iii) with inversion of the configuration can be carried out with diethylamino sulphur trifluoride or preferably with bis-(2-methoxyethyl)-aminosulphur trifluoride in $CH_2Cl_2$ at −80 to 20° C.

Saponification of the ester (step iv) can be carried out as described in the synthetic procedure 1a). Amide formation by reaction of the acid with $R^c$—B—$NH_2$ (step v) can be accom-

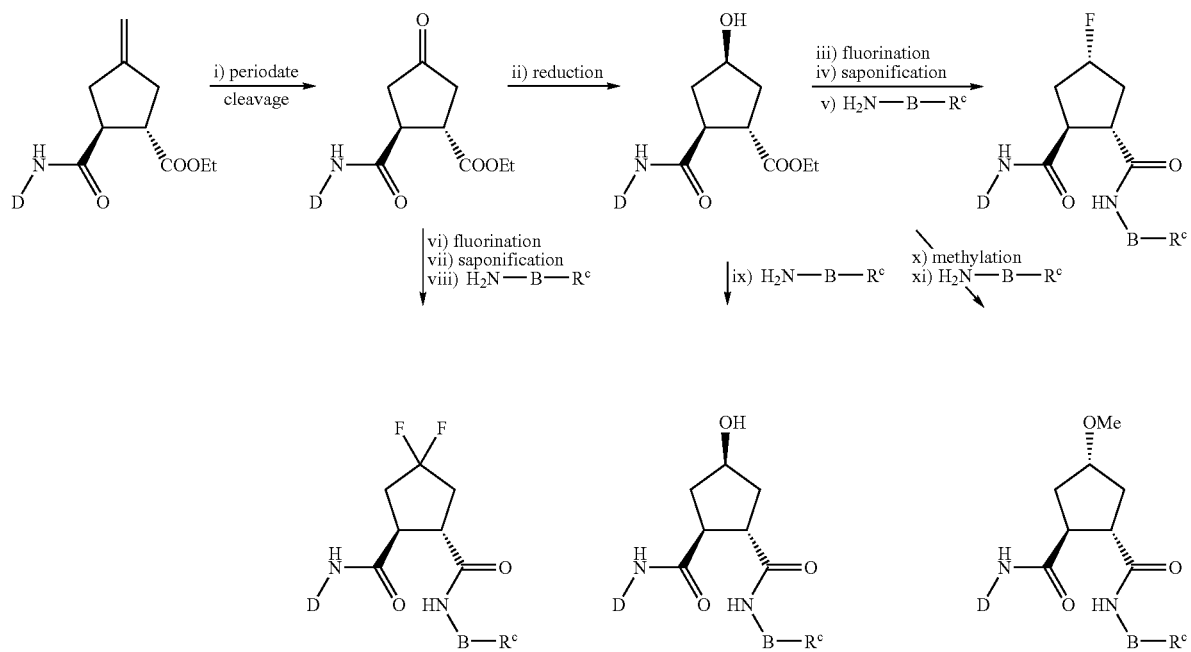

plished as described in the synthetic procedure 1a) preferably by using isobutylcarbamoyl chloride as the activating agent.

Fluorination of the ketone (step vi), saponification (step vii) and subsequent amide formation with $R^c$—B—$NH_2$ (step viii) can be accomplished as described for step iii)-v).

Alternatively, the hydroxyester can be converted to the amide with $R^c$—B—$NH_2$ (step ix) with $AlMe_3$ according to the method of M. Weinreb et al. (Tetrahedron Lett., 48, 4171, 1977). The relative and absolute configuration of the amide shown in the scheme was determined by an X-ray analysis of the amide complexed with factor Xa.

The alcohol group can be converted to the methylether (step x) using MeCl, MeBr or preferably MeI in a solvent like THF or MeCN, preferably a mixture of both and an additive such as AgO at 0-40° C. preferably at 20° C. Amide formation (xi) can be accomplished according to step ix) using $AlMe_3$. Both epimers of the ethers are available as pure isomers.

d) Modifications of D

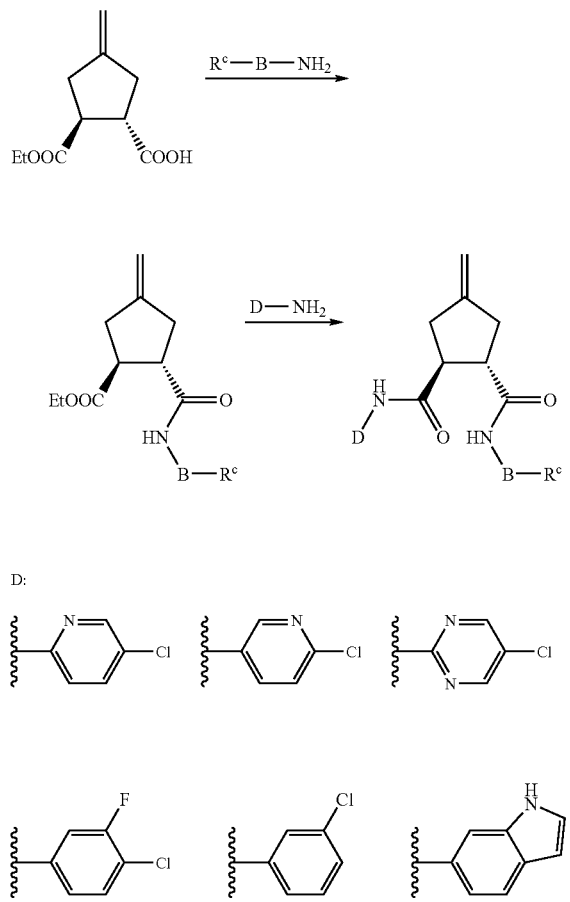

Amide formation by reaction of the acid with $R^c$—B—$NH_2$ can be accomplished as described in the synthetic procedures 1a), the preferred method involves isobutylcarbamoyl chloride as activating agent and N-methylmorpholine as base at −20 to 60° C., preferably at 45° C.

The second amide group can be introduced by reaction of the ester with D-$NH_2$ in the presence of $AlMe_3$ as described in the synthetic procedure 2c).

e) Modifications of —B—$R^c$

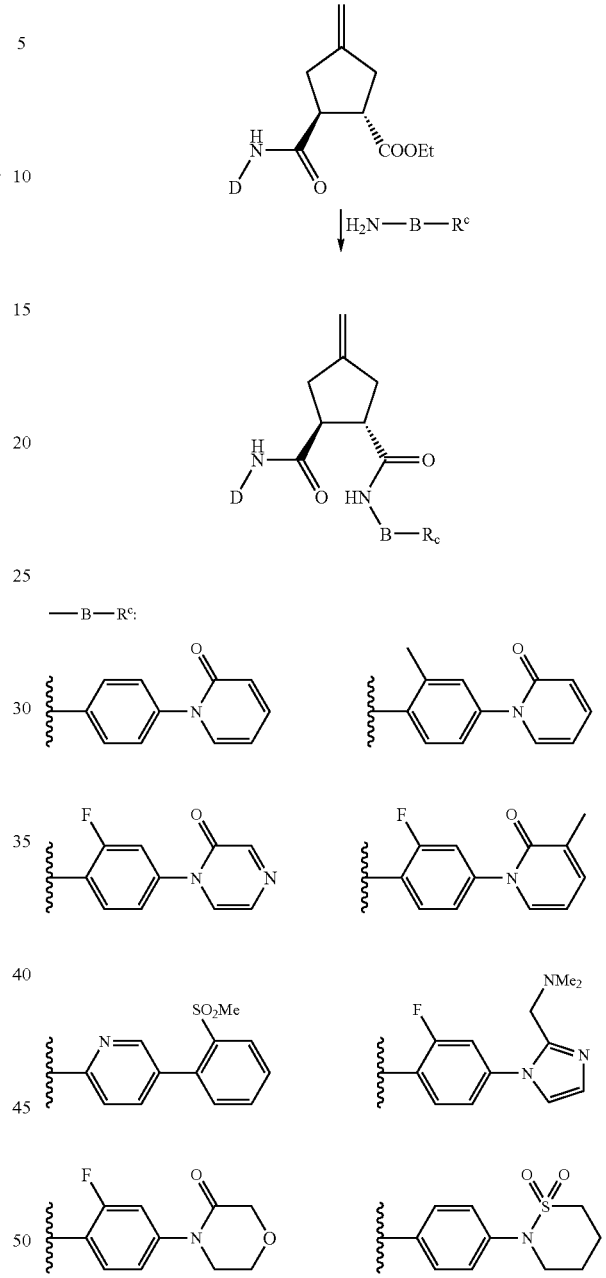

The second amide group can be introduced by reaction of the ester with $R^c$—B—$NH_2$ in the presence of $AlMe_3$ as described in the synthetic procedure 2c). Preparation of the anilines $R^c$—B—$NH_2$ are described in C. F. Bigge et al. (patent application WO 2003045912); R. A. Galemmo et al. (patent application WO9857937); M. L. Quan et al. (patent application WO 2003047517); I. Zeid et al. (Journal de la Societe Algerienne de Chimie 4(2), 171, 1994.

Et in the schemes under procedure 1. a) to e) can be replaced with another $C_{1-6}$ alkyl group, preferably $C_{1-4}$ alkyl group. B, $R^c$ and D in the schemes under procedure 2.a) to e) are as defined before. D is preferably 4-chlorophenyl. —B—$R^c$ is preferably 2-fluoro-4-(2-oxo-2H-pyridin-1-yl)phenyl.

3. Synthesis of Cyclopropane Dicarboxamide Derivatives Via Succinimide

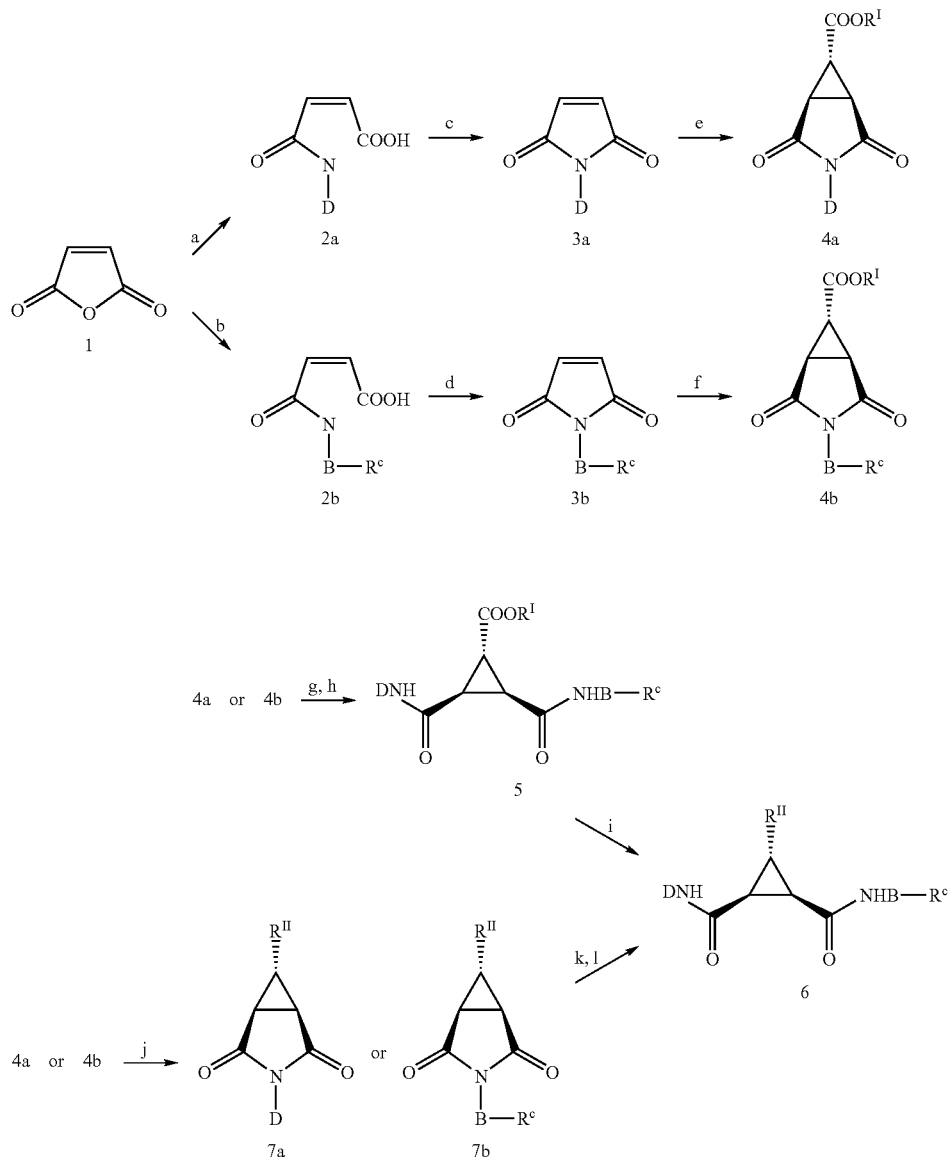

B, $R^c$ and D are as defined before.

Preferably D is 4-chlorophenyl. Preferably —B—$R^c$ is 2-fluoro-4-(2-oxo-2H-pyridin-1-yl)-phenyl. In a suitable solvent such as e.g. acetonitrile, maleic anhydride 1 is treated with D-NH$_2$ or $R^c$—B—NH$_2$ to give amido carboxamide-carboxylic acids 2a or 2b, respectively (steps a/b). They can be converted to the cyclic imides 3a/b, respectively, e.g. by treatment with an acid (e.g. HCl) a Lewis Acid (e.g ZnCl$_2$) or an anhydride (e.g. acetic anhydride) in analogy to e.g. Pal et al., Synthesis, 10, 2003, 1549; Yoshitake et al., J. Chem. Soc. Perkin II, 2002, 1611; Dubovchich et al., Bioorg. Med. Chem. Lett., 12, 2002, 1529; Shin et al., Tet. Lett., 42, 7, 2001, 1325 (steps c/d). Cyclopropanation of 3a/b to racemic 4a/b, respectively ($R^I$=$C_{1-6}$ alkyl), is usually carried out by treatment with an α-diazo acetic acid alkyl ester (preferably α-diazo acetic acid ethyl ester) in a solvent such as e.g. toluene or xylene at 80-160° C., though conditions analogous to those described e.g. by Kozhushkov et al., Synthesis, 2003, 956; Kurihara et al., Heterocycles 20, 1983, 1919, or Saegusa et al., J. Org. Chem. 38, 1973, 2319 may also be used (steps e/f). The racemic cyclopropano-imides 4a/b are then treated with $R^c$—BNH$_2$ or DNH$_2$, respectively, to give racemic opened derivative 5 (step g/h). Usually this is carried out in a suitable solvent such as DMF, whereas usually $R^c$—BNH$_2$/DNH$_2$ is previously deprotonated with a strong base such as e.g. NaH. The ester moiety can be derivatized to various functional groups (leading to racemic 6, step i) using methods generally known to those skilled in the art. Some typical examples are given below:

Hydrolysis of racemic 5 (e.g. with aq. LiOH) leads to the corresponding carboxylic acid ($R^{II}$=COOH) which can be converted into amides (e.g. $R^{II}$=CONMe$_2$) by treatment with a suited amine and a condensating reagent such as e.g. DCC (dicyclohexylcarbodiimide) or EDCI (N-3-dimethylaminopropyl)-N'-ethylcarbodiimide hydrochloride).

Treatment of racemic 5 with an excess of an alkyllithium or alkylmagnesiumhalide leads to derivatives with $R^{II}$=C(C$_{1-6}$ alkyl)$_2$OH. Reduction of racemic 5 (e.g. with NaBH$_4$ in MeOH) leads to the derivative with $R^{II}$=CH$_2$OH that can be oxidized to the aldehyde ($R^{II}$=CHO) e.g. by a Swern-oxidation. Treatment of derivatives with $R^{II}$=CH$_2$OH with a sulfonylating agent such as e.g. mesylchloride, tosylchloride, triflic anhydride leads to intermediates with e.g. $R^{II}$=CH$_2$OMs, CH$_2$OTs, CH$_2$OTf that can be reacted with a nucleophile "Nu or NuH" such as e.g. an amine or a heterocycle (e.g. imidazole) to give derivatives with $R^{II}$=CH$_2$-Nu. Derivatives obtained by this method for which $R^{II}$=CH$_2$—NHC$_{1-6}$ alkyl$^1$ are readily converted to derivatives with $R^{II}$=CH$_2$—NC$_{1-6}$ alkyl$^1$(SO$_2$C$_{1-6}$ alkyl$^2$), $R^{II}$=CH$_2$—NC$_{1-6}$ alkyl$^1$(COC$_{1-6}$ alkyl$^2$), with $R^{II}$=CH$_2$—NC$_{1-6}$ alkyl$^1$ (COOalkyl$^2$) by treatment with a reagent Cl—SO$_2$ C$_{1-6}$ alkyl$^2$, ClCO C$_{1-6}$ alkyl$^2$, ClCOOC$_{1-6}$ alkyl$^2$, respectively, preferably in the presence of a base such as e.g. triethylamine.

Derivatives with $R^{II}$=CHO, COOH, CONHR$^{III}$ (wherein $R^{III}$=H or C$_{1-6}$ alkyl) may readily be transformed (in one or more steps) into derivatives with $R^{II}$=heterocycle using methodologies analogous to those described or mentioned e.g. in "Advances in Heterocyclic chemistry, Monograph series by A. Katritzky (Editor) and Comprehensive Heterocyclic Chemistry II, a review of Literature 1982-1995, Monograph Series by A. Katritzky (editor); for more specific examples (e.g. oxazolidines) see e.g.: Cwik et al., Tet. Lett., 43, 2002, 3985; Vorbrueggen et al., Tetrahedron, 49, 1993, 9353.

Alternatively, the COOR$^I$-group of racemic 4a/b may be transformed to the above mentioned groups $R^{II}$ (step j, leading to racemic 7a/b) prior to the $R^c$—BNH$_2$/DNH$_2$-promoted imide opening using the same methods described for step i. The imide opening of 7a/b to racemic 6 is carried out thereafter (steps k/l) in analogy to steps g/h. If desired or required separation of the enantiomers of the racemic 4a/b, 5, 6, or 7a/b can be carried out by suitable chiral HPLC. Steps g-l may, if desired, be carried out on enantiomerically pure 4a/b, 5 or 7a/b as well.

4. Synthesis of Cyclopropane Dicarboxamide Derivatives via Succinic Anhydrides

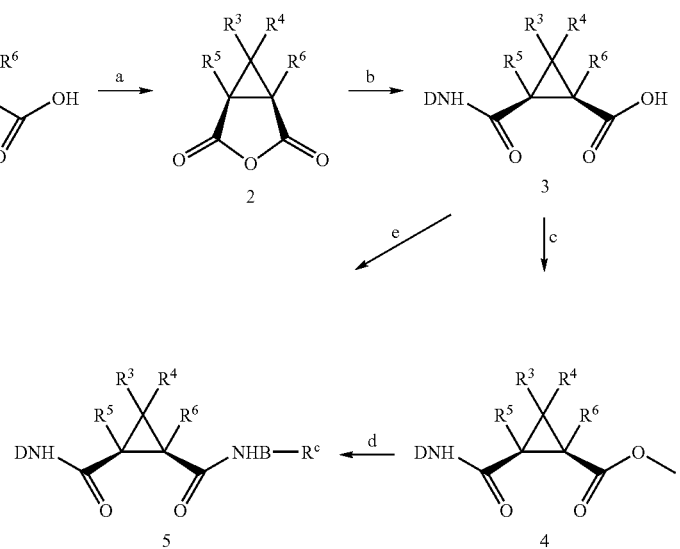

$R^3$ to $R^6$ in the scheme are hydrogen, C$_{1-6}$ alkyl or C$_{3-7}$ cycloalkyl. B, $R^c$ and D are as defined before.

Preferably D is 4-chlorophenyl. Preferably —B—$R^c$ is 2-fluoro-4-(2-oxo-2H-pyridin-1-yl)-phenyl. Diacids 1 (Commercially Available or Known from the Literature) which can exist as mixture of the racemic cis isomer and the racemic trans isomer are converted to the racemic cis anhydrides 2 by treatment with neat acetic anhydride at reflux temperature or with trifluoroacetic anhydride at 0° (scheme 1, step a). The trans diacids cannot react to the corresponding anhydrides. The racemic cis anhydrides 2 are separated off by destillation. Alternatively, the reaction mixture is concentrated and the crude product is used for the next step without further purification. Racemic anhydrides 2 are reacted with anilines D-NH$_2$ in an inert solvent such as THF to give racemic cyclopropane monocarboxamides 3 (step b). The products resulting from attack at the less hindered carbon are formed predominantly. Esterification of monocarboxamides 3 (step c) is usually accomplished by dissolving them in an alcohol such as MeOH and EtOH followed by treatment with thionyl chloride at 0° C. in analogy to J. Ind. Chem. Soc. 1992, 69(10), 683-4. Racemic esters 4 are then reacted with anilines $R^c$—B—NH$_2$ (step d). Anilines are preactivated with AlMe$_3$ in a solvent such as toluene or dioxane and then treated with an ester 4 at elevated temperature (usually 90° C.) to give racemic 1,2-cyclopropandicarboxamides 5.

5. Synthesis of Cyclopropane Dicarboxamide Derivatives via Intramolecular Cyclopropanation

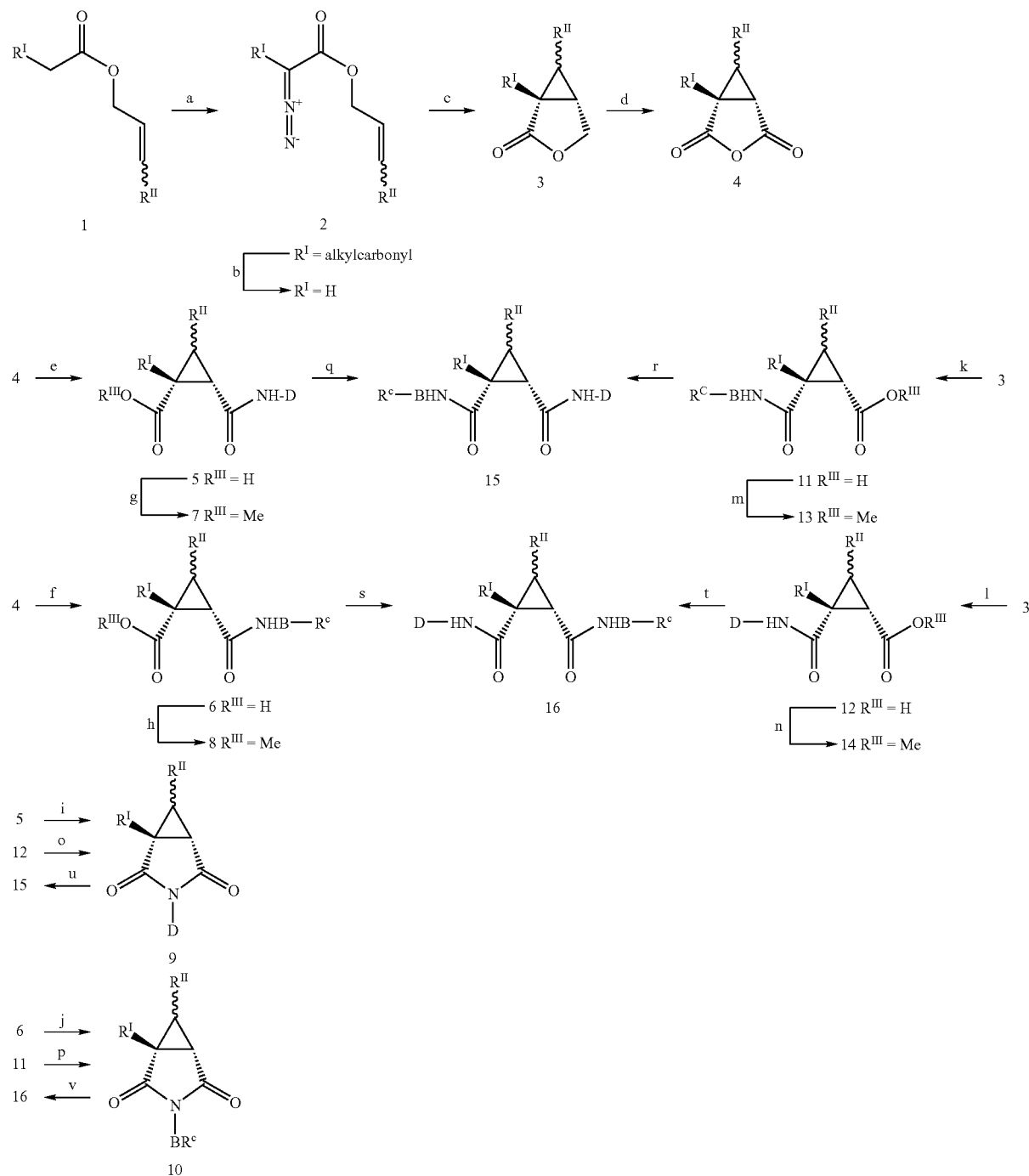

B, $R^c$ and D are as defined before.

An Allylester derivative 1, wherein $R^I$=$COC_{1-6}$ alkyl, $COOC_{1-6}$ alkyl or COOallyl and $R^{II}$=H, $C_{1-6}$ alkyl or a suitably O-protected hydroxymethyl, is converted to the diazo derivative 2 using a diazo transfer reagent such as e.g. tosylazide, diphenylphosphorylazide or 4-acetamidobenzensulfonyl azide in the presence of a base such as e.g. N,N-ethyldiisopropylamine (step a). Optionally, for derivatives with $R^I$=$COC_{1-6}$ alkyl a deacylation to $R^I$=H may be carried out by treatment with e.g. LiOH (step b). Intramolecular cyclopropanation e.g. using a chiral or a achiral catalyst derived e.g. from rhodium, copper, cobalt or ruthenium (as described e.g. in *J. Med. Chem.* 2004, 47, p 456-66, *Chem. Commun.* 1997, p211-2, *Org. Lett.* 2002, p1911-4, *Tet. Lett*, 2001, p 2521-4, *Ang. Chem.* Int. Ed. 1999, p700-2.) leads to the racemic or enantiomerically enriched (up to >98% ee) bicyclic lactone derivative 3 (step c). Alternatively, for $R^I$=$COC_{1-6}$ alkyl, COO $C_{1-6}$ alkyl, COOallyl, Allylester 1 can be directly transformed into lactone 3, e.g. by treatment with $I_2$ in presence of $K_2CO_3$ as described e.g. by Toeke et al. in Tetrahedron 1993, 49, p5133-46, or by treatment with a chloro-, bromo, iodo-, methanesulfonyloxy- or trifluormethanesulfonyloxy-methyloxirane after deprotonation of 1 with a strong base such as e.g. NaH as described e.g. by Burgess et al. in J. Org. Chem. 1992, 57, p5931-6. The lactone 3 can be converted to the anhydride 4 by treatment with an oxidizing agent such as e.g. Jones reagent, pyridinium dichromate, pyridinium chlorochromate and subsequent treatment with a dehydrating agent such as e.g. thionylchloride or oxalylchloride (step d). Treatment of the anhydride 4 with either $H_2N$—B—$R^c$ or $H_2N$-D in the presence of a base such as e.g. pyridine leads to the amido carboxylic acids 5 (step e) and 6 (step f), respectively, or mixtures of the two (attack of the amine usually occurring preferentially at the sterically less hindered carbonyl group). Both 5 and 6 can be converted to the methyl esters 7 and 8 by treatment with thionylchloride in MeOH or with iodomethane in presence of potassium carbonate (steps g and h) or to the imides 9 and 10 (steps i and j), respectively, by treatment with a dehydrating agent such as e.g. thionylchloride. Amido carboxylic acids 11 and 12 can be obtained by opening of the lactone 3 with either $H_2N$—B—$R^c$ or $H_2N$-D (previously treated with a strong base such as e.g. lithium bis(trimethylsilyl)amide) and subsequent oxidation of the resulting alcohol using a oxidative agent such as e.g. Jones reagent (steps k and l). In analogy to steps g or h they can be converted to the corresponding methylesters 13 or 14 (steps m and n) or to the imides 9 or 10 (steps o and p).

Esters 7 and 13 are reacted with $H_2N$—B—$R^c$ or $H_2N$-D, respectively (preactivated with $AlMe_3$) to bisamide 15 (steps q and r). Similarly esters 8 and 14 are reacted to bisamide 16 (steps s and t). Bisamide 15 may alternatively be obtained by reaction of imide 9 with $H_2N$—B—$R^c$ previously pretreated with a strong base such as e.g. lithium bis(trimethylsilyl) amide (step u), bisamide 16 by reaction of imide 10 with $H_2N$-D (pretreated with a strong base such as e.g. lithium bis(trimethylsilyl)amide (step v). These reactions are usually carried out in an inert solvent such as THF, dioxane or toluene at temperatures ranging from RT to 150° C.

If desired $R^I$ may be derivatized to other functional groups. Typical transformations are e.g.: Hydrolysis of $R^I$=$COOC_{1-6}$ Alkyl to $R^I$=COOH with e.g. LiOH, reduction of $R^I$=$COOC_{1-6}$ Alkyl to $R^I$=$CH_2OH$ with e.g. $NaBH_4$. Derivatives with $R^I$=COOH can be converted into amides (e.g. $R^I$=$CONMe_2$) by treatment with a suited amine and a condensating reagent such as e.g. DCC (dicyclohexylcarbodiimide) or EDCI (N-3-dimethylaminopropyl)-N'-ethylcarbodiimide hydrochloride). Treatment of derivatives with $R^I$=$CH_2OH$ with a sulfonylating agent such as e.g. mesylchloride, tosylchloride, triflic anhydride leads to intermediates with e.g. $R^{II}$=$CH_2OMs$, $CH_2OTs$, $CH_2OTf$ that can be reacted with a nucleophile "Nu or NuH" such as e.g. an amine, a heterocycle, or a source of a cyanide or a fluoride anion, or a heterocycle, to give derivatives with $R^I$=$CH_2$-Nu. $R^I$ or $R^{II}$=$CH_2OH$ can be oxidized to $R^I$ or $R^{II}$=CHO e.g. by a Swern-oxidation and derivatized to $R^I$ or $R^{II}$=$C_{1-6}$ alkyl by Wittig-type reaction and subsequent hydrogenation of the double bond.

For derivatives with $R^{II}$=suitably protected hydroxymethyl, deprotection may be carried out to $R^{II}$=$CH_2OH$ using standard procedures commonly known to those in the art (e.g. desilylation with TBAF, or de-paramethoxybenzylation with DDQ) and e.g. oxidized to $R^{II}$=COOH or formyl. $R^{II}$=$CH_2OH$, COOH or formyl can be further derivatized using the same methodologies described above for $R^I$=$CH_2OH$ or COOH.

As described above, the compounds of formula (I) are active compounds and inhibit the coagulation factor Xa. These compounds consequently influence both platelet activation which is induced by this factors and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumor cells and prevent metastases. They can therefore also be used as antitumor agents.

Prevention and/or treatment of thrombotic disorders, particularly arterial or deep vein thrombosis, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of diseases which are associated with the coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumor In another preferred embodiment, the invention relates to a method for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumor, which method comprises administering a compound as defined above to a human being or animal subject suffering from a disease associated with the coagulation factor Xa.

The inhibition of the coagulation factor Xa by the compounds of the present invention can be demonstrated with the aid of a chromogenic peptide substrate assay such as described in the Examples hereinafter.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 µl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 µl of plasma/inhibitor mixture in the measurement container. The clotting reaction was initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking was determined photooptically from the ACL. The inhibitor concentration, which brought about a doubling of the PT clotting time, was determined by fitting the data to an exponential regression (XLfit).

The compounds of the present invention can furthermore be characterised by the Activated Partial Thromboplastin time (aPTT). This coagulation test can e.g. be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in $1.0 \times 10^{-4}$ M ellagic acid, stabilizers and preservative, Dade Behring, Inc., Cat. B4218-100) Thereafter, 0.25 ml aliquots of human plasma (obtained from whole blood anti-coagulated with ⅒ volume of 108 mM Na citrate) are spiked with 5 µl of test compound in at least 6 concentrations. 50 µl plasma at 4° C. containing ⅕₀ vol. inhibitor in solvent are incubated with 50 µl Dade® Actin® FS Activated PTT reagent in water at 37° C. for 3 min., then 50 µl CaCl2.2H2O 25 mM in water at 37° C. are added. The time up to the fibrin cross-linking was determined photooptically from the ACL. The inhibitor concentration, which brought about a doubling of the APTT clotting time, was determined by fitting the data to an exponential regression (XLfit).

The Ki values of the active compounds of the present invention preferably amount to about 0.001 to 50 µM, especially about 0.001 to 1 µM. The PT values preferably amount to about 0.5 to 100 µM, especially to about 0.5 to 10 µM. The aPTT values preferably amount to about 0.5 to 100 µM, especially to about 0.5 to 10 µM.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Example 1 and 2

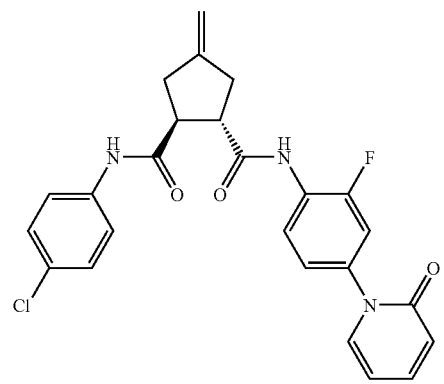

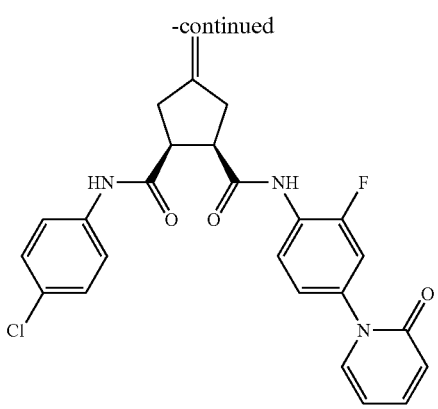

Trans-(1SR,2SR)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide} (1) and Cis-(1SR,2RS)-4-methylene-cyclopentane-1,2-dicarboxylic acid 1-[(4-chloro-phenyl)-amide]2-{[2-fluoro-4-(2-oxo-2H-pyridin-1-yl)-phenyl]-amide} (2)

Step 1: trans-(1SR,2SR)-4-Methylene-cyclopentane-1,2-dicarboxylic acid ethyl ester (1a)

A suspension of 20.0 g of trans-(1SR,2SR)-4-methylene-cyclopentane-1,2-dicarboxylic acid diethyl ester and 36.6 g of potassium carbonate in 200 ml of MeOH was heated at reflux temperature for 2 h. The mixture was cooled to 22°, diluted with 200 ml of water, the pH was adjusted to 2 using 80 ml of 25% HCl and the mixture was evaporated to half of the volume. The aqueous layer was extracted with AcOEt, the organic layer was washed with water, dried and evaporated to give 16.7 g of a crude mixture of mono and diacid. Optionally this mixture can be purified on silica using $CH_2Cl_2$/MeOH (19:1) to give 8.60 g of the pure title compound 1a. MS: 183.3 $(M-H)^-$.

Step 2: trans-(1SR,2SR)-2-(4-Chloro-phenylcarbamoyl)-4-methylene-cyclopentane carboxylic acid methyl ester (1b)

The crude mixture containing 1a (16.7 g) was dissolved in 500 ml of $CH_3CN$ and treated subsequently with 51 ml of $NEt_3$, 25.0 g hydroxybenzotriazole and 31.3 g of N-(3-dimethylaminopropyl)-N'-ethylcarbodiimide hydrochloride and stirring was continued at 22° C. for 30 min. The mixture was treated with 23.1 g of 4-chloroaniline and stirring was continued at 22° C. for 16 h and at 60° C. for 5 h. The mixture was evaporated and the residue partitioned between AcOEt and 0.1 N NaOH. The organic layer was washed with 0.1 N NaOH, 1 N HCl and brine, dried and evaporated to give 13.7 g of the crude title compound 1b.

Step 3: trans-(1SR,2SR)-2-(4-Chloro-phenylcarbamoyl)-4-methylene-cyclopentane carboxylic acid (1c)

The crude material 1b (13.7 g) was dissolved in 200 ml of MeOH and 20 ml of 7 N NaOH, the solution was stirred at 22° C. for 2 h and evaporated. The residue was partitioned between 0.1 N NaOH and $CH_2Cl_2$, the aqueous layer was washed with $CH_2Cl_2$ and the aqueous layer was acidified with 25% HCl, the suspension was filtered and the residue dried to give 11.0 g (45% overall) of the pure title compound 1c as a pale brown solid. MS: 278.3 $(M-H)^-$.

Step 4: Trans-(1SR,2SR)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide} (1) and cis-(1SR,2RS)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide} (2)

To a solution of 6.0 g of 1c and 2.6 ml of 4-methylmorpholine in 60 ml of THF was added at −16° C. 3.1 ml of isobutyl chloroformate over 20 min, the suspension was stirred at −16° C. for 20 min and then warmed to 0° C. The mixture was diluted with 4 ml of DMF and after 10 min cooled to −16° C. The mixture was treated with a suspension of 4.82 g of 1-(4-amino-3-fluoro-phenyl)-1H-pyridin-2-one (prepared according to C. F. Bigge et al., patent application WO 2003045912) in 40 ml of DMF and heated at 60° C. for 1 h. A further portion of 0.56 ml of isobutyl chloroformate was added and stirring was continued at 22° C. for 16 h. The mixture was evaporated, the residue partitioned between 1 N HCl and $CH_2Cl_2$, the organic layer was washed with 1 N HCl, 1 N NaOH and brine, dried and evaporated. The brown residue was chromatographed on silica (700 g) using a gradient of $CH_2Cl_2$/MeOH (100:1 to 95:5) to give 3.67 g (37%) of the pure title compound 1. MS: 466.3 $(M+H)^+$.

The second fraction contained 2.04 g (20%) of the pure title compound 2. MS: 466.1 $(M+H)^+$.

Example 3

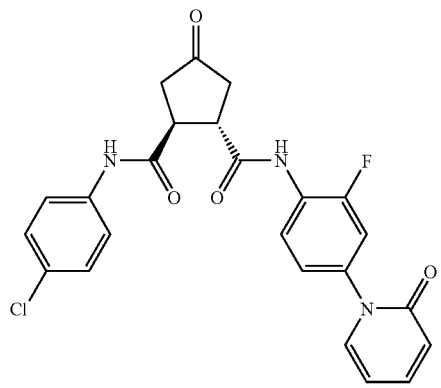

Trans-(1SR,2SR)-4-Oxo-cyclopentane-1,2-dicarboxylic acid 1-[(4-chloro-phenyl)-amide]2-{[2-fluoro-4-(2-oxo-2H-pyridin-1-yl)-phenyl]-amide}

To a solution of 2.80 g of compound 1 in 200 ml of MeOH and 65 ml of water was added at 22° C. 3.8 ml of a 2.5% solution of $OsO_4$ in t-BuOH and 3.89 g of $NaIO_4$ and stirring was continued at 22° C. for 1 h. The suspension was evaporated to a volume of ca. 50 ml and partitioned between AcOEt and brine. The organic layer was dried, evaporated and the residue chromatographed on silica using a gradient of AcOEt/ heptane (3:1 to 5:1) to give 2.27 g (81%) of the pure title compound. MS: 468.5 (M+H)+.

Example 4

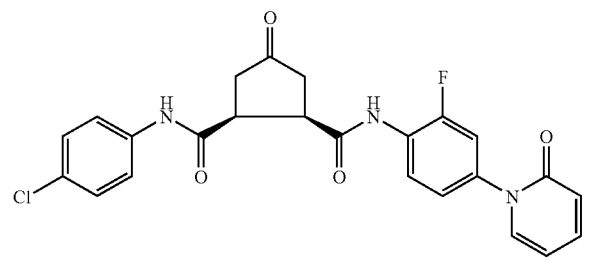

Cis-(1SR,2RS)-4-Oxo-cyclopentane-1,2-dicarboxylic acid 1-[(4-chloro-phenyl)-amide]2-{[2-fluoro-4-(2-oxo-2H-pyridin-1-yl)-phenyl]-amide}

Starting from 2 the title compound was prepared in 90% yield according to the procedure described in example 3. MS: 468.4 (M+H)+.

Example 5

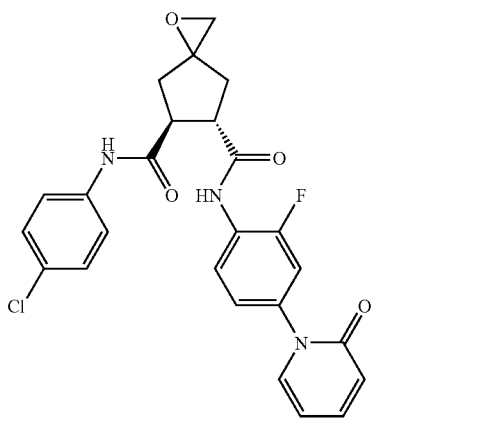

Mixture of (3RS,5SR,6SR)- and (3SR,5SR,6SR)-1-Oxa-spiro[2.4]heptane-5,6-dicarboxylic acid 5-[(4-chloro-phenyl)-amide]6-{[2-fluoro-4-(2-oxo-2H-pyridin-1-yl)-phenyl]-amide}

A suspension of 0.54 g of compound 1 (from example 1 and 2) in 20 ml of CH$_2$Cl$_2$ was treated at 22° C. with 0.51 g of 70% m-chloroperbenzoic acid and stirring was continued for 3 h. The mixture was treated with 10 ml of a saturated aqueous solution of Na$_2$SO$_3$ and stirring was continued for 30 min. The mixture was washed with 1 N NaOH and brine, the organic layer was dried and evaporated. The residue was chromatographed on silica (epoxide pre-adsorbed on silica) using AcOEt to give 0.41 g (73%) of the pure title compound.

MS: 482.5 (M+H)+. The epoxide epimers (3RS,5SR,6SR)- and (3SR,5SR,6SR) can be separated using a larger amount of silica.

Example 6

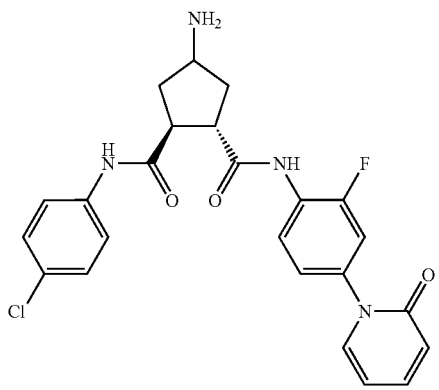

Mixture of (1SR,2SR,4RS)- and (1SR,2SR,4SR)-4-Amino-cyclopentane-1,2-dicarboxylic acid 1-[(4-chloro-phenyl)-amide]2-{[2-fluoro-4-(2-oxo-2H-pyridin-1-yl)-phenyl]-amide}

A solution of 500 mg of the ketone from example 3 and 8.25 g of ammonium acetate in 100 ml of MeOH was treated with 77 mg of sodium cyanoborohydride and stirring was continued for 16 h. The solution was evaporated, the residue partitioned between CH$_2$Cl$_2$ and 0.1 N HCl, the pH of the aqueous layer was adjusted to 9 using 1 N NaOH and extracted with CH$_2$Cl$_2$. The organic layer was washed with brine, dried and evaporated to give 60% of the title compound. MS: 569.4 (M+H)+.

Example 7

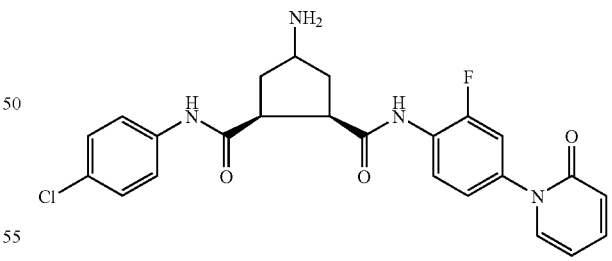

Mixture of (1SR,2RS,4RS)- and (1SR,2RS,4SR)-4-Amino-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the ketone from example 4, the title compound was prepared in 64% yield according to the procedure described in example 6. MS: 569.5 (M+H)+.

Example 8

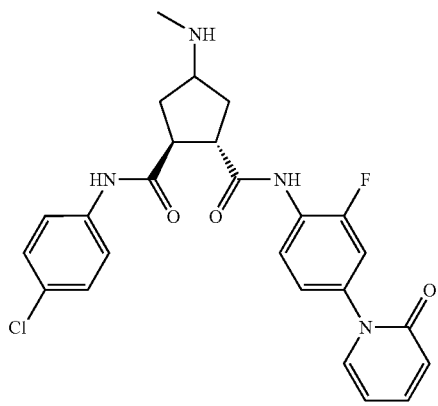

Mixture of (1SR,2SR,4RS)- and (1SR,2SR,4SR)-4-ethylamino-cyclopentane-1,2-dicarboxylic acid 1-[(4-chloro-phenyl)-amide]2-{[2-fluoro-4-(2-oxo-2H-pyridin-1-yl)-phenyl]-amide}

General Procedure

To a solution of 0.1 mmole of the ketone from example 3 and 0.2 mmole of the amine in 2.5 ml of THF was added at 0° C. AcOH until the pH was 5 followed by addition of 0.11 mmole of sodium cyanoborohydride and stirring was continued at 22° C. for 16 h. The mixture was evaporated and the residue purified by prep. HPLC (RP-18) using a gradient of $CH_3CN/H_2O$ (containing 0.1% of HCOOH) (20:80 to 95:5).

Starting from the ketone from example 3 and methylamine, the title compound was prepared in 65% yield. MS: 583.5 $(M+H)^+$.

Example 9

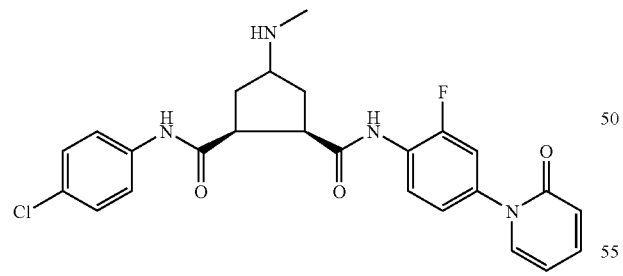

Mixture of (1SR,2RS,4RS)- and (1SR,2RS,4SR)-ethylamino-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the ketone from example 4 and methylamine, the title compound was prepared in 70% yield. MS: 583.1 $(M+H)^+$.

Example 10

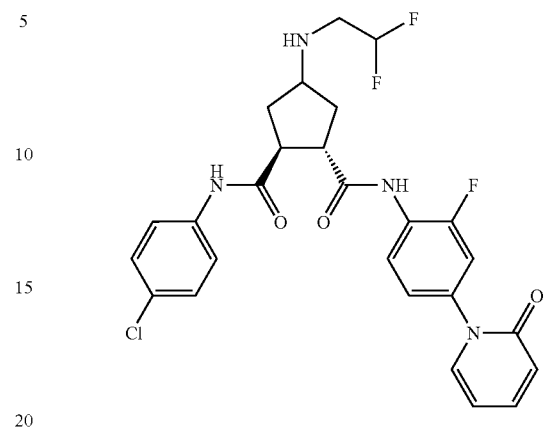

Mixture of (1SR,2SR,4RS)- and (1SR,SR,4SR)-4-(2,2-difluoro-ethylamino)-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the ketone from example 3 and 2,2-difluoroethylamine, the title compound was prepared in 87% yield. MS: 533.3 $(M+H)^+$.

Example 11

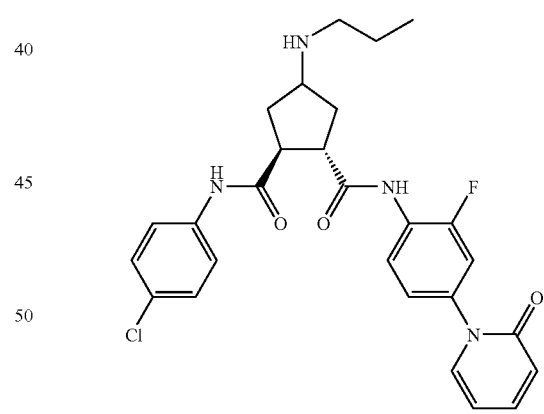

Mixture of (1SR,2SR,4RS)- and (1SR,SR,4SR)-4-Propylamino-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the ketone from example 3 and propylamine, the title compound was prepared in 67% yield. MS: 511.5 $(M+H)^+$.

Example 12

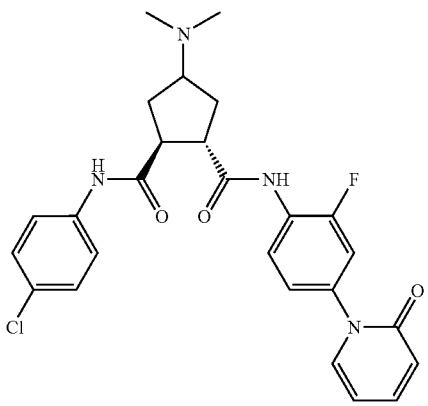

Mixture of (1SR,2SR,4RS)- and (1SR,2SR,4SR)-4-Dimethylamino-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the ketone from example 3 and dimethylamine, the title compound was prepared in 22% yield. MS: 497.1 (M+H)$^+$.

Example 13

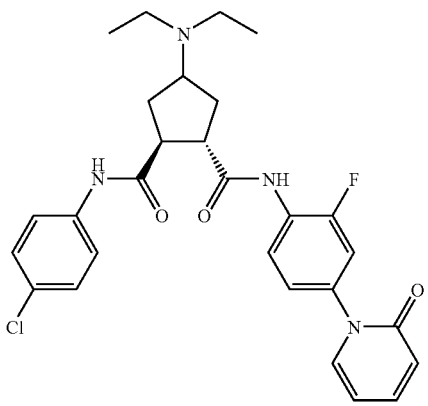

Mixture of (1SR,2SR,4RS)- and (1SR,2SR,4SR)-4-Diethylamino-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the ketone from example 3 and diethylamine, the title compound was prepared in 52% yield. MS: 525.5 (M+H)$^+$.

Example 14

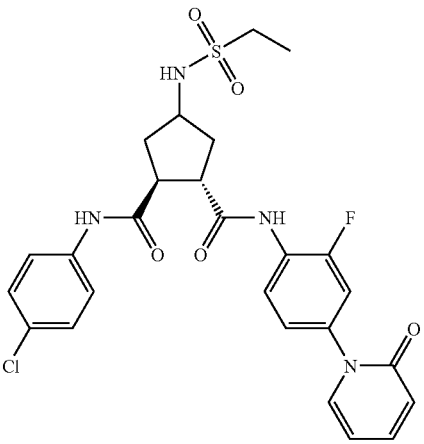

Mixture of (1SR,2SR,4RS)- and (1SR,2SR,4SR)-4-Ethanesulfonylamino-cydopentane-1,2-dicarboxylic acid 1-[(4-chloro-phenyl)-amide]2-{[2-fluoro-4-(2-oxo-2H-pyridin-1-yl)-phenyl]-amide}

General Procedure

To a solution of 0.1 mmole of the amine and 0.25 mmole of N,N-diisopropylethylamine in 0.7 ml of CH$_3$CN was added at 22° C. 0.15 mmole of the sulfonylchloride or methyl chloroformate or p-nitrophenylformate and stirring was continued for 1-16 h. The mixture was evaporated and the residue chromatographed on silica using CH$_2$Cl$_2$/MeOH (97:3).

Starting from the amine from example 6 and ethylsulfonyl chloride, the title compound was prepared in 61% yield. MS: 560.9 (M+H)$^+$.

Example 15

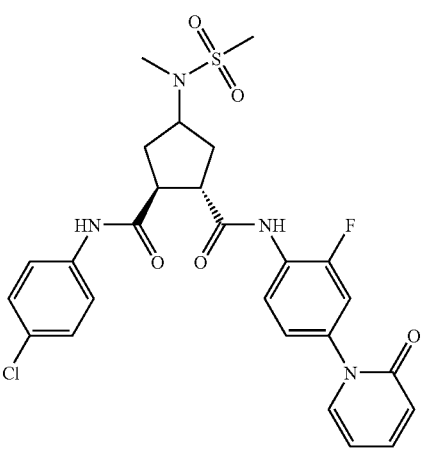

Mixture of (1SR,2SR,4RS)- and (1SR,2SR,4SR)-(Methanesulfonyl-methyl-amino)-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the amine from example 8 and methylsulfonyl chloride, the title compound was prepared in 69% yield. MS: 561.3 (M+H)$^+$.

Example 16

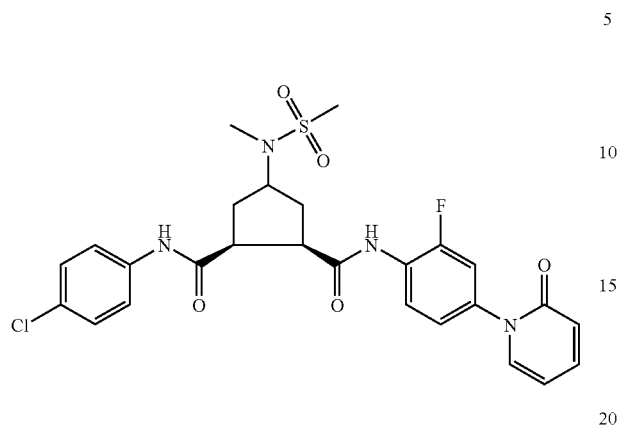

Mixture of (1SR,2RS,4RS)- and (1SR,2RS,4SR)-4-(Methanesulfonyl-methyl-amino)-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the amine from example 9 and methylsulfonyl chloride, the title compound was prepared in 74% yield. MS: 561.0 (M+H)$^+$.

Example 17

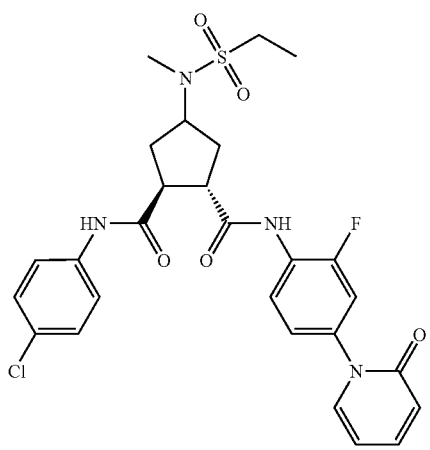

Mixture of (1SR,2SR,4RS)- and (1SR,2SR,4SR)-4-(Ethanesulfonyl-methyl-amino)-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the amine from example 8 and ethylsulfonyl chloride, the title compound was prepared in 45% yield. MS: 575.0 (M+H)$^+$.

Example 18

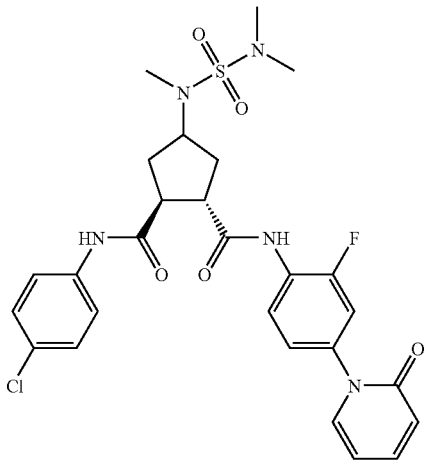

Mixture of (1SR,2SR,4RS)- and (1SR,2SR,4SR)-4-(Dimethylsulfamoyl-methyl-amino)-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the amine from example 8 and dimethylsulfamoyl chloride, the title compound was prepared in 78% yield. MS: 590.5 (M+H)$^+$.

Example 19

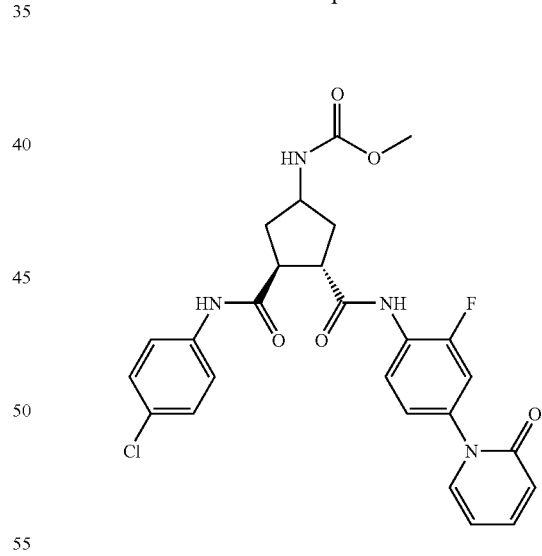

Mixture of (1RS,3SR,4SR)- and (1SR,3SR,4SR)-3-(4-Chloro-phenylcarbamoyl)-4-[2-fluoro-4-(2-oxo-2H-pyridin-1-yl)-phenylcarbamoyl]-cyclopentyl}-carbamic acid methyl ester Starting from the amine from example 6 and methyl chloroformate, the title compound was prepared in 96% yield. MS: 527.3 (M+H)$^+$.

Example 20

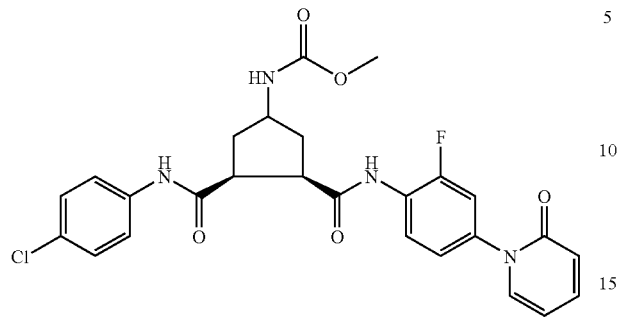

(1RS,3SR,4RS)- or (1SR,3SR,4RS)-3-(4-Chloro-phenylcarbamoyl)-4-[2-fluoro-4-(2-oxo-2-pyridin-1-yl)-phenylcarbamoyl]-cyclopentyl}-carbamic acid methyl ester Starting from the amine from example 6 and methyl chloroformate, the title compound was prepared in 30% yield after crystallization from EtOH. MS: 527.0 (M+H)+.

Example 21

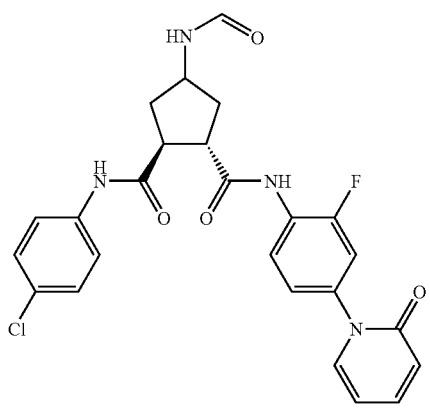

Mixture of (1SR,2SR,4RS)- and (1SR,2SR,4SR)-4-Formylamino-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the amine from example 6 and p-nitrophenylformate, the title compound was prepared in 77% yield. MS: 497.1 (M+H)+.

Example 22

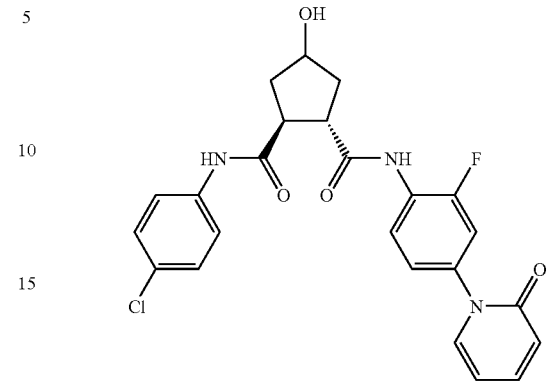

Mixture of (1SR,2SR,4RS)- and (1SR,2SR,4SR)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide}

To a solution of 450 mg of the ketone from example 3 in 9 ml of THF was added at 22° C. 110 mg of sodium borohydride and stirring was continued for 1 h. The solution was quenched with 3 drops of 1 N HCl and 10 ml of brine and the aqueous layer was extracted with AcOEt. The organic layer was dried, evaporated and the residue chromatographed on silica using $CH_2Cl_2$/MeOH (20:1) to give 417 mg (92%) of the title compound. MS: 470.1 (M+H)+.

Example 23

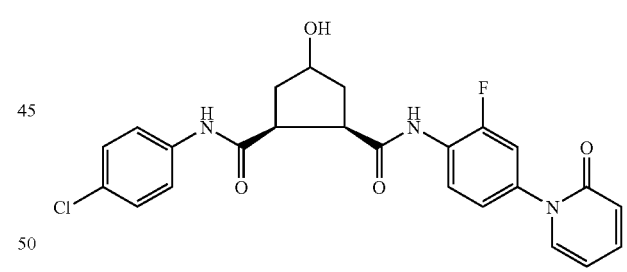

Mixture of (1SR,2RS,4RS)- and (1SR,2RS,4SR)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide}

To a suspension of 93 mg of the ketone from example 4 in 5 ml of THF was added at 22° C. 38 mg of sodium borohydride and stirring was continued for 2 h. The suspension was diluted with 1 ml of MeOH and stirring was continued for 15 min. The solution was evaporated and the residue partitioned between 1 N HCl and $CH_2Cl_2$. The organic layer was dried, evaporated and the residue triturated with AcOEt to give 67 mg (72%) of the title compound. MS: 469.5 (M+H)+.

Example 24

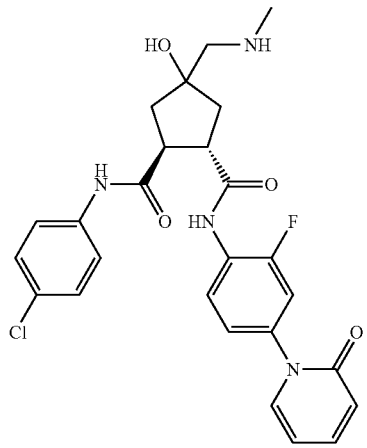

Mixture of (1SR,2SR,4RS)- and (1SR,2SR,4SR)-4-Hydroxy-4-methylaminomethyl-cyclopentane-1,2-dicarboxylic acid 1-[(4-chloro-phenyl)-amide]2-{[2-fluoro-4-(2-oxo-2H-pyridin-1-yl)-phenyl]-amide}

General Procedure

A solution of 0.5 mmole of the epoxide from example 5 and 5 mmole of the amine in 10 ml of EtOH was heated in a sealed tube to 40° C. for 1-20 h. The solution was evaporated and the residue chromatographed on silica using a gradient of $CH_2Cl_2$ to $CH_2Cl_2$/MeOH 10:1. Starting from the epoxide from example 5 and $MeNH_2$, the title compound was prepared in 78% yield. MS: 513.5 $(M+H)^+$.

Example 25

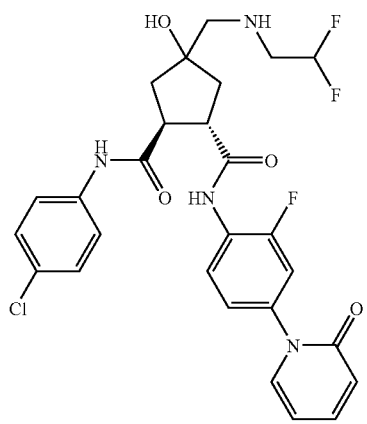

Mixture of (1SR,2SR,4RS)- and (1SR,2SR,4SR)-4-[(2,2-Difluoro-ethylamino)-methyl]-4-hydroxy-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the epoxide from example 5 and $CHF_2CH_2NH_2$, the title compound was prepared in 78% yield. MS: 563.5 $(M+H)^+$.

Example 26

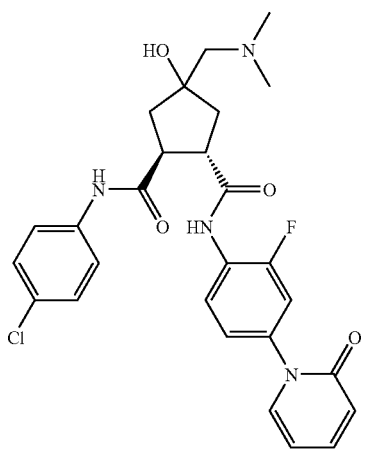

Mixture of (1SR,2SR,4RS)- and (1SR,2SR,4SR)-4-Dimethylaminomethyl-4-hydroxy-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the epoxide from example 5 and $Me_2NH$ the title compound was prepared in 70% yield. MS: 527.2 $(M)^+$.

Example 27

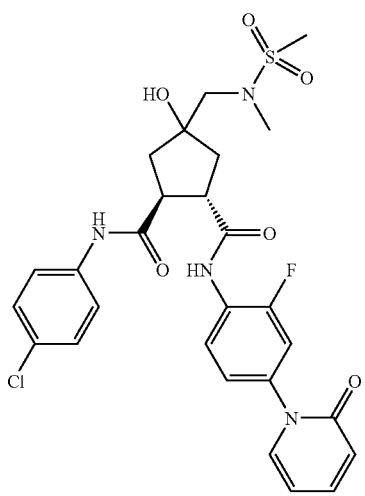

Mixture of (1SR,2SR,4RS)- and (1SR,2SR,4SR)-4-Hydroxy-4-[(methanesulfonyl-methyl-amino)-methyl]-cyclopentane-1,2-dicarboxylic acid 1-[(4-chloro-phenyl)-amide]2-{[2-fluoro-4-(2-oxo-2H-pyridin-1-yl)-phenyl]-amide}

General Procedure

To a suspension of 0.1 mmole of the aminoalcohol from example 24 in 1.5 ml of $CH_3CN$ was added subsequently at 22° C. 0.3 mmole of N-ethyldiisopropylamine and 0.3 mmole of the sulfochloride and stirring was continued for 4 h. The mixture was evaporated and the residue partitioned between $CH_2Cl_2$ and 1 N HCl. The organic layer was washed with 1 N NaOH and brine, dried and evaporated. The residue was purified by prep. HPLC (RP-18) using a gradient of $CH_3CN$/$H_2O$ (containing 0.1% of HCOOH) (20:80 to 95:5).

Starting from the aminoalcohol from example 24 and MeSO₂Cl, the title compound was prepared in 58% yield. MS: 591.5 (M)⁺.

Example 28

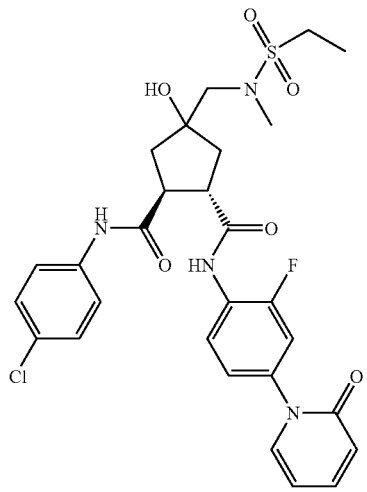

Mixture of (1SR,2SR,4RS)- and (1SR,2SR,4SR)-4-[(Ethanesulfonyl-methyl-amino)-methyl]-4-hydroxy-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the aminoalcohol from example 24 and EtSO₂Cl, the title compound was prepared in 69% yield. MS: 605.3 (M)⁺.

Example 29

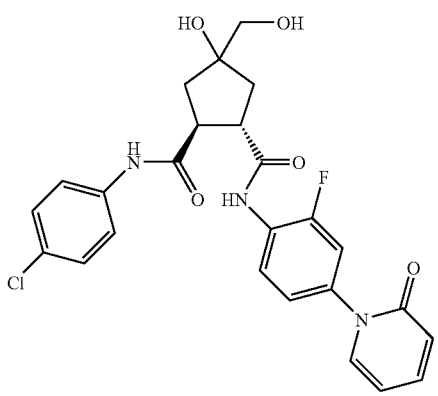

Mixture of (1SR,2SR,4RS)- and (1SR,2SR,4SR)-4-Hydroxy-4-hydroxymethyl-cyclopentane-1,2-dicarboxylic acid 1-[(4-chloro-phenyl)-amide]2-{[2-fluoro-4-(2-oxo-2H-pyridin-1-yl)-phenyl]-amide}

To a suspension of 30 mg of the epoxide from example 5 in 0.5 ml of THF was added at 22° C. 0.5 ml of 1M H₂SO₄ and stirring was continued for 2 h. The solution was neutralized with Na₂CO₃ and evaporated. The residue was chromatographed on a thick layer silica plate using CH₂Cl₂/MeOH (9:1) to give the title compound in 74% yield. MS: 498.3 (M−H)⁻.

Example 30

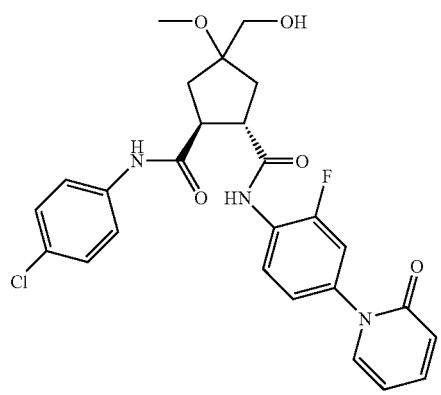

Mixture of (1SR,2SR,4RS)- and (1SR,2SR,4SR)-4-Hydroxymethyl-4-methoxy-cyclopentane-1,2-dicarboxylic acid 1-[(4-chloro-phenyl)-amide]2-{[2-fluoro-4-(2-oxo-2H-pyridin-1-yl)-phenyl]-amide}

General Procedure

To a solution of 0.1 mmole of the epoxide from example 5 in 1.5 ml of the alcohol was added at 0° C. 0.2 mmole BF₃.OEt₂ and stirring was continued at 22° C. for 2 h. The solution was evaporated and the residue chromatographed on a thick layer silica plate using CH₂Cl₂/MeOH (15:1) to give the pure product.

Starting from the epoxide from example 5 and MeOH, the title compound was prepared in 52% yield. MS: 514.5 (M+H)⁺.

Example 31

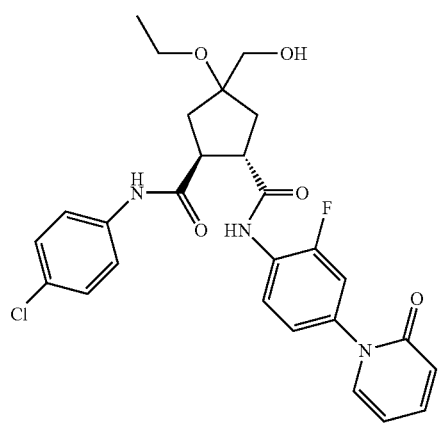

Mixture of (1SR,2SR,4RS)- and (1SR,2SR,4SR)-4-Ethoxy-4-hydroxymethyl-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the epoxide from example 5 and EtOH, the title compound was prepared in 34% yield. MS: 528.5 (M+H)⁺.

Example 32

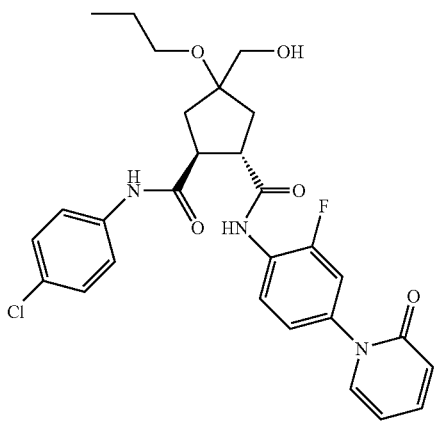

Mixture of (1SR,2SR,4RS)- and (1SR,2SR,4SR)-4-Hydroxymethyl-4-propoxy-cyclopentane-1,2-dicarboxylic acid 1-[(4-chloro-phenyl)-amide]2-{[2-fluoro-4-(2-oxo-2H-pyridin-1-yl)-phenyl]-amide}

Starting from the epoxide from example 5 and PrOH, the title compound was prepared in 52% yield. MS: 542.3 (M)$^+$.

Example 33

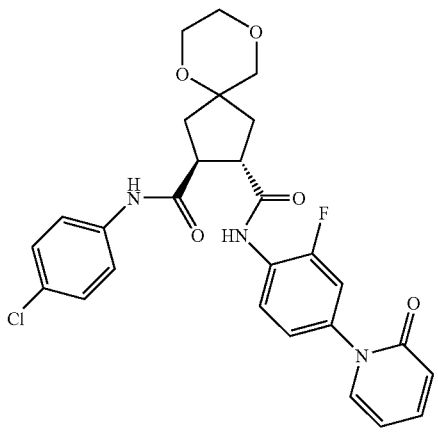

Mixture of (2SR,3SR,5RS)- and (2SR,3SR,5SR)-6,9-Dioxa-spiro[4.5]decane-2,3-dicarboxylic acid 2-[(4-chloro-phenyl)-amide]3-{[2-fluoro-4-(2-oxo-2H-pyridin-1-yl)-phenyl]-amide}

To a solution of 0.2 mmole of the epoxide from example 5 in 2 ml of 2-chloroethanol was added at 0° C. 0.01 mmole of BF$_3$.OEt$_2$ and stirring was continued at 22° C. for 1 h. The solution was evaporated, the residue partitioned between water and AcOEt and the organic layer was dried and evaporated. The residue was chromatographed on silica using a gradient of CH$_2$Cl$_2$ to CH$_2$Cl$_2$/MeOH (30:1) to give 60 mg of the intermediate chloroalcohol. The material was dissolved in 2 ml of CH$_3$CN, 30 mg of KI and 0.17 ml of 32% NaOH were added and the mixture was heated in a microwave apparatus to 100° C. for 15 min. The mixture was evaporated and the residue partitioned between sat. NH$_4$Cl and AcOEt, the organic layer was dried and evaporated. The residue was purified by prep. HPLC (RP-18) using a gradient of CH$_3$CN/H$_2$O (containing 0.1% of HCOOH) (20:80 to 95:5) to give 6 mg of the title compound. MS: 526.3 (M+H)$^+$.

Example 34

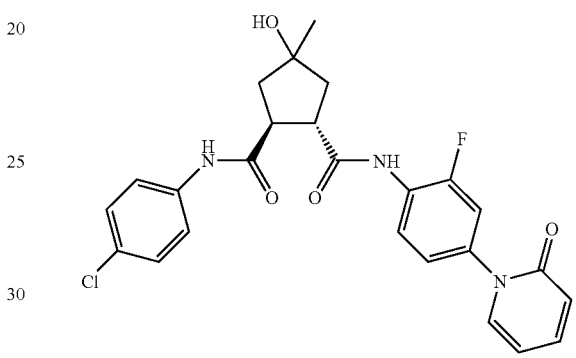

Mixture of (1SR,2SR,4RS)- and (1SR,2SR,4SR)-4-Hydroxy-4-methyl-cyclopentane-1,2-dicarboxylic acid 1-[(4-chloro-phenyl)-amide]2-{[2-fluoro-4-(2-oxo-2H-pyridin-1-yl)-phenyl]-amide}

To a solution of 72 mg of the epoxide from example 5 in 0.5 ml of a 5 M LiClO$_4$ in Et$_2$O was added at 22° C. 32 μl of BH$_3$.NEt$_3$ and stirring was continued at 22° C. for 3 h. The solution was partitioned between water and CH$_2$Cl$_2$ and the organic layer was dried and evaporated. The residue was chromatographed on silica using CH$_2$Cl$_2$/MeOH (9:1) to give 26 mg (36%) of the title compound. MS: 484.5 (M+H)$^+$.

Example 35

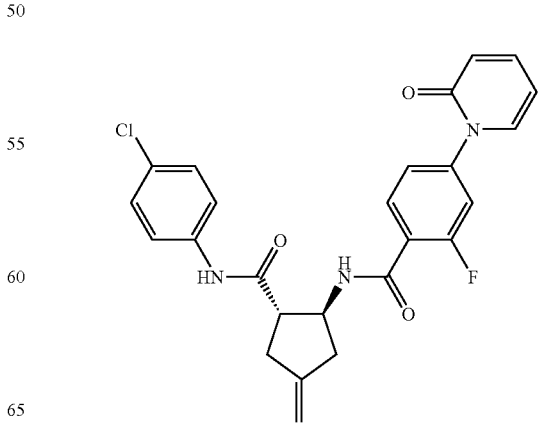

N-[(1SR,2SR)-2-(4-Chloro-phenylcarbamoyl)-4-methylene-cyclopentyl]-2-fluoro-4-(2-oxo-2H-pyridin-1-yl)-benzamide

Step 1: (1RS,2RS)-2-tert-butoxycarbonylamino-4-methylene-cyclopentanecarboxylic acid methyl ester (35a)

To a solution of 2.03 g trans-(1SR,2SR)-4-methylene-cyclopentane-1,2-dicarboxylic acid ethyl ester (prepared and purified according to example 1 and 2, step 1) and 1.13 g of NEt$_3$ in 25 ml of toluene was added drop wise at 22° C. 3.03 g of diphenylphosphoryl azide and the mixture was heated at 80° C. for 30 min. The mixture was diluted with 4.08 g of t-BuOH and heating was continued at 90° C. for 16 h. The mixture was evaporated and the residue chromatographed on silica using a gradient of CH$_2$Cl$_2$ to CH$_2$Cl$_2$/MeOH (99:1) to give 1.55 g (55%) of the title compound 35a.

Step 2: (1RS,2RS)-2-tert-Butoxycarbonylamino-4-methylene-cyclopentanecarboxylic acid (35b)

To a solution of 1.28 g of 35a in 30 ml of MeOH was added a solution of 0.42 g of LiOH.H$_2$O in 10 ml of H$_2$O and stirring was continued at 50° C. for 1 h. The solution was evaporated to approximately half of the volume, the aqueous layer was washed with Et$_2$O, acidified with HCl, the suspension was filtered and the residue dried to give 1.13 g (93%) of the title compound 35b. MS: 242.4 (M+H)$^+$.

Step 3: [(1SR,2SR)-2-(4-Chloro-phenylcarbamoyl)-4-methylene-cyclopentyl]-carbamic acid tert-butyl ester (35c)

A stirred solution of 1.085 g of 35b in 10 ml of THF was treated subsequently with 1.25 ml of NEt$_3$, 0.69 g hydroxybenzotriazole, 1.21 g of N-(3-dimethylaminopropyl)-N'-ethylcarbodiimide hydrochloride and 0.63 g of 4-chloroaniline and stirring was continued at 22° C. for 16 h. The mixture was evaporated and the residue partitioned between CH$_2$Cl$_2$ and 1 N HCl. The separated organic layer consisting of a white suspension was filtered and the residue dried to give 1.01 g (64%) of the title compound 35c. MS: 351.4 (M+H)$^+$.

Step 4: (1SR,2SR)-2-Amino-4-methylene-cyclopentanecarboxylic acid (4-chloro-phenyl)-amide (35d)

A solution of 0.98 g of 35c in 10 ml of CH$_2$Cl$_2$ and 1.07 ml of trifluoroacetic acid was stirred at 22° C. for 2 h. The solution was evaporated and the residue partitioned between H$_2$O and CH$_2$Cl$_2$. The aqueous layer was treated slowly with NaHCO$_3$ until pH=8, the suspension was filtered, the residue washed with H$_2$O and dried to give 0.48 g (69%) of the title compound 35d. MS: 251.3 (M+H)$^+$.

Step 5: 2-Fluoro-4-(2-oxo-2H-pyridin-1-yl)-benzoic acid (35e)

To a solution of 10.96 g of 4-bromo-2-fluoro-benzoic acid in 40 ml of DMSO was added subsequently 6.67 g of 2-hydroxypyridine, 1.10 g of 8-hydroxyquinoline, 1.43 g of Cu(I)I and 7.61 g of K$_2$CO$_3$ and the mixture was heated to 150° C. for 18 h. The suspension was diluted with water, filtered, the residue was washed with AcOEt, triturated with MeOH, filtered and dried to give 5.77 g of the title compound 35e. MS: 234.1 (M+H)$^+$.

Step 6: N-[(1SR,2SR)-2-(4-Chloro-phenylcarbamoyl)-4-methylene-cyclopentyl]-2-fluoro-4-(2-oxo-2H-pyridin-1-yl)-benzamide (35)

Starting from 35d and 35e, the title compound was prepared in 69% yield according to the procedure for example 1 and 2, step 2. MS: 466.3 (M+H)$^+$.

Example 36

N-[(1SR,2SR)-2-(4-Chloro-phenylcarbamoyl)-4-oxo-cyclopentyl]-2-fluoro-4-(2-oxo-2H-pyridin-1-yl)-benzamide

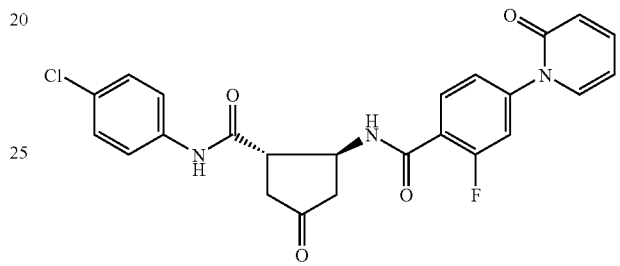

Starting from the olefin from example 35 the title compound was prepared in 41% yield according to the procedure in example 3. MS: 468.5 (M+H)$^+$.

Example 37

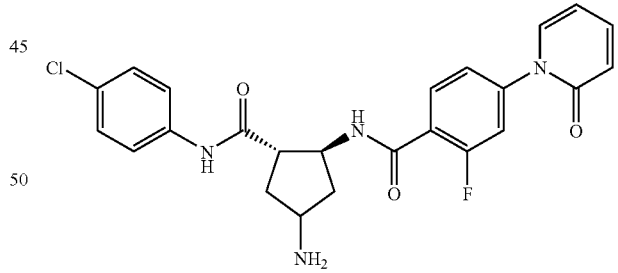

Mixture of (1SR,2SR,4SR)- and (1SR,2SR,4RS)-N-[4-Amino-2-(4-chloro-phenylcarbamoyl)-cyclopentyl]-2-fluoro-4-(2-oxo-2H-pyridin-1-yl)-benzamide Starting from the ketone of example 36, the title compound was prepared in 62% yield according to the procedure in example 6. MS: 469.5 (M+H)$^+$.

Example 38

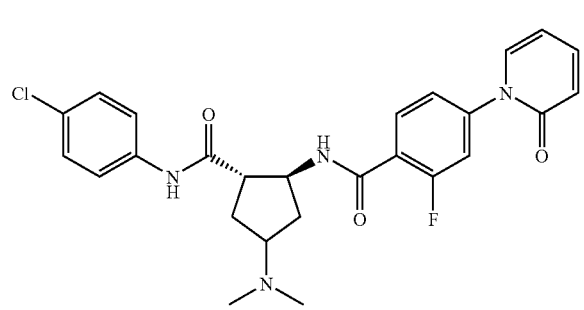

Mixture of (1SR,2SR,4SR)- and (1SR,2SR,4RS)-N-[2-(4-Chloro-phenylcarbamoyl)-4-dimethylamino-cyclopentyl]-2-fluoro-4-(2-oxo-2H-pyridin-1-yl)-benzamide Starting from the ketone of example 36, the title compound was prepared in 48% yield according to the procedure in example 12. MS: 497.1 (M+H)$^+$.

Example 39

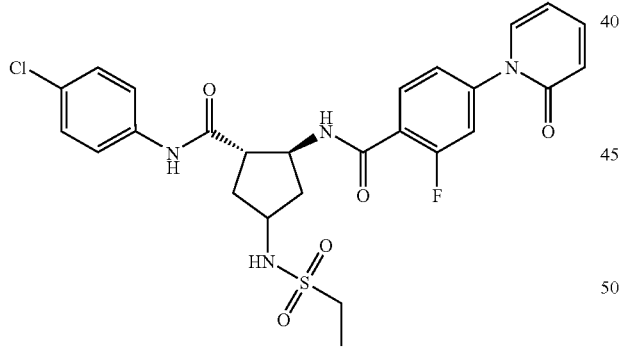

Mixture of (1SR,2SR,4SR)- and (1SR,2SR,4RS)-N-[2-(4-Chloro-phenylcarbamoyl)-4-ethanesulfonylamino-cyclopentyl]-2-fluoro-4-(2-oxo-2H-pyridin-1-yl)-benzamide Starting from the amine of example 37, the title compound was prepared in 60% yield according to the procedure in example 14. MS: 560.9 (M)$^+$.

Example 40

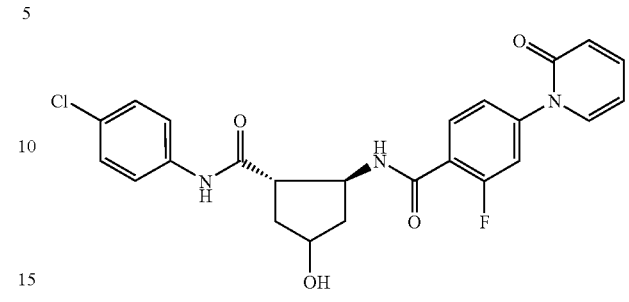

Mixture of (1SR,2SR,4SR)- and (1SR,2SR,4RS)-N-[2-(4-Chloro-phenylcarbamoyl)-4-hydroxy-cyclopentyl]-2-fluoro-4-(2-oxo-2H-pyridin-1-yl)-benzamide Starting from the ketone of example 36, the title compound was prepared in 47% yield according to the procedure in example 22. MS: 470.5 (M+H)$^+$.

Example 41 and 42

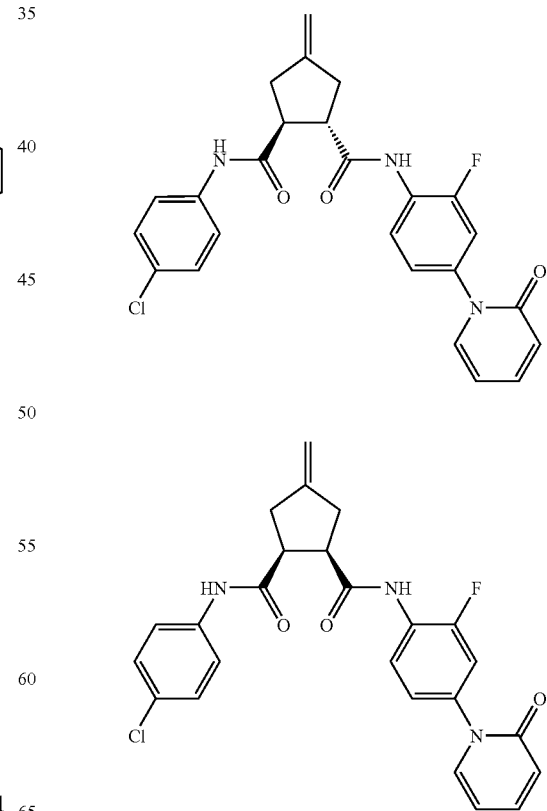

(1S,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide} (41) and (1R,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide} (42)

Step 1:
(1S,2S)-4-Methylene-cyclopentane-1,2-dicarboxylic acid diethyl ester (41a)

An emulsion of 1.1 g racemic trans-4-Methylene-cyclopentane-1,2-dicarboxylic acid diethyl ester (Merck8.14188.0010) in an aqueous buffer (potassium phosphate 5 mM, NaCl 0.1 M) was adjusted to pH 7.0. Under stirring at 7° C. the hydrolysis was performed with 14 mg lipase PN from *Phycomyces nitens* [Wako Chemicals GmbH Nissanstrasse 2 D-41468 Neuss Germany; catalog # 122-02651] under pH control (pH-stat, 1M NaOH). After consumption of 2.4 ml 1 M NaOH solution within 24 h the reaction mixture was extracted twice with 250 ml t-butyl methyl ether. The organic phase was subsequently washed with 250 ml saturated sodium bicarbonate and 250 ml saturated NaCl solution. Evaporation and drying in vacuo overnight yielded 0.49 g of the title compound 41a. MS: 226.0 (M)$^+$; chiral GC: ee >99% (BGB-175, 30 m×0.25 mm; H$_2$, 120 kPa, Split ⅟20; 100-180° C., 2° C./min; Inj.-T.: 200° C.; Dect.-T.: 220° C.).

Step 2:
(1S,2S)-4-Methylene-cyclopentane-1,2-dicarboxylic acid monoethyl ester (41b)

An emulsion of 1.7 g 41a in an aqueous buffer (potassium phosphate 3 mM, NaCl 0.1 M) was adjusted to pH 7.5. Under stirring at room temperature the hydrolysis was performed with 15 mg lipase OF from *Candida rugosa* under pH control (pH-static, 1M NaOH). After consumption of 6.5 ml 1M NaOH solution and 7 h the reaction mixture was washed with 50 ml t-butyl methyl ether. The aqueous layer was adjusted to pH 2.0 (conc. HCl) and was extracted with 85 ml ethyl acetate. Drying over sodium sulfate, evaporation and drying overnight on a high vacuum yielded 1.28 g of the title compound 41b. MS: 197.2 (M−H)$^-$; chiral GC: ee 99.4%.

Step 3: (1S,2S)-2-(4-Chloro-phenylcarbamoyl)-4-methylene-cyclopentanecarboxylic acid ethyl ester (41c)

Starting from 41b, the title compound was prepared in 73% yield according to the procedure for example 1 and 2, step 2. MS: 308.3 (M+H)$^+$.

Step 4: (1S,2S)-2-(4-Chloro-phenylcarbamoyl)-4-methylene-cyclopentanecarboxylic acid (41d)

Starting from 41c, the title compound was prepared in 100% yield according to the procedure for example 1 and 2, step 3. MS: 278.3 (M−H)$^-$.

Step 5: (1S,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide} (41) and (1R,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide} (42)

Starting from 41d, the title compound 41 was prepared according to the procedure for example 1 and 2, step 4. MS: 466.1 (M+H)$^+$.

The second fraction afforded the title compound 42. MS: 466.3 (M+H)$^+$.

Example 43

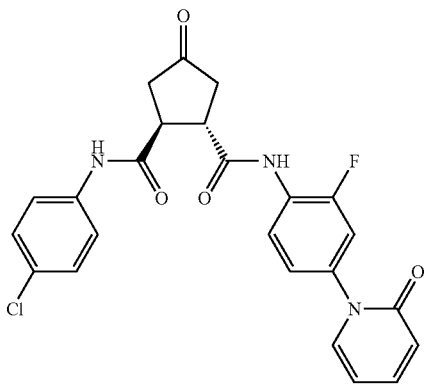

(1S,2S)-4-Oxo-cyclopentane-1,2-dicarboxylic acid 1-[(4-chloro-phenyl)-amide]2-{[2-fluoro-4-(2-oxo-2H-pyridin-1-yl)-phenyl]-amide}

Starting from 41, the title compound 43 was prepared in quantitative yield according to the procedure for example 3. MS: 468.5 (M+H)$^+$.

Example 44 and 45

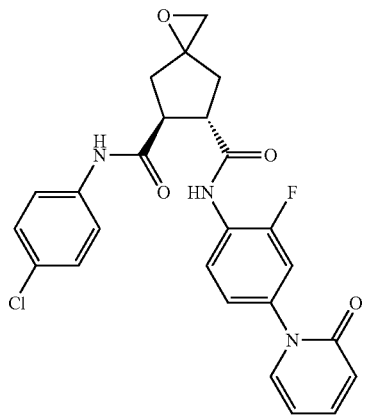

(3R or 3S,5S,6S)-1-Oxa-spiro[2.4]heptane-5,6-dicarboxylic acid 5-[(4-chloro-phenyl)-amide]6-{[2-fluoro-4-(2-oxo-2H-pyridin-1-yl)-phenyl]-amide} (44) and (3S or 3R,5S,6S)-1-Oxa-spiro[2.4]heptane-5,6-dicarboxylic acid 5-[(4-chloro-phenyl)-amide]6-{[2-fluoro-4-(2-oxo-2H-pyridin-1-yl)-phenyl]-amide} (45)

Starting from 41, the title compounds 44 and 45 were prepared according to the procedure for example 5 to give in the first fraction compound 44. MS: 482.5 (M+H)$^+$. The second fraction afforded compound 45. MS: 482.5 (M+H)$^+$.

Example 46

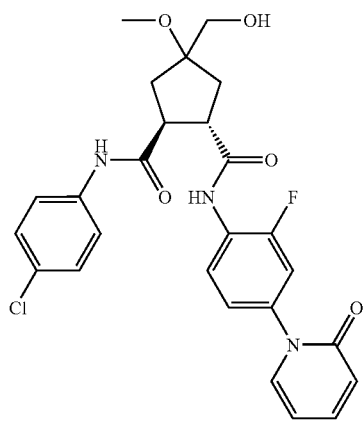

(1S,2S,4R)- or (1S,2S,4S)-4-Hydroxymethyl-4-methoxy-cyclopentane-1,2-dicarboxylic acid 1-[(4-chloro-phenyl)-amide]2-{[2-fluoro-4-(2-oxo-2H-pyridin-1-yl)-phenyl]-amide}

Starting from 44, the title compound was prepared according to the procedure for example 30. MS: 514.5 (M+H)⁺.

Example 47

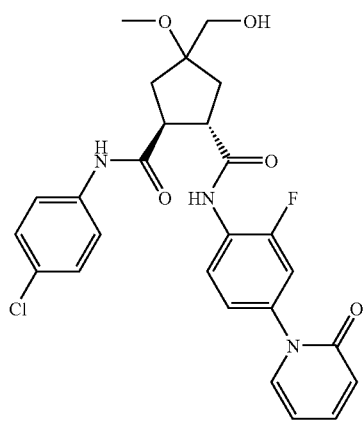

(1S,2S,4S)- or (1S,2S,4R)-4-Hydroxymethyl-4-methoxy-cyclopentane-1,2-dicarboxylic acid 1-[(4-chloro-phenyl)-amide]2-{[2-fluoro-4-(2-oxo-2H-pyridin-1-yl)-phenyl]-amide}

Starting from 45, the title compound was prepared according to the procedure for example 30. MS: 514.5 (M+H)⁺.

Example 48

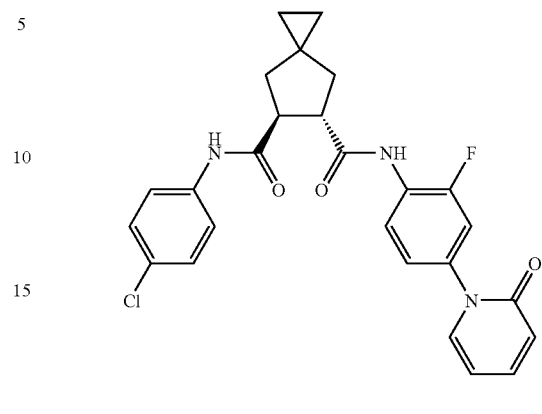

(5S,6S)-Spiro[2.4]heptane-5,6-dicarboxylic acid (4-chloro-phenyl)-amide [2-fluoro-4-(2-oxo-2H-pyridin-1-yl)-phenyl]-amide To a solution of 0.69 ml of a 1M diethylzinc solution in hexane and 2 ml of CH₂Cl₂ was subsequently added at 0° C. 54 μl of CF₃COOH and 10 min later 55 μl of CH₂I₂. After a further 10 min at 0° C., a solution of 80 mg of 41 in 1 ml of CH₂Cl₂ was added and stirring was continued at 20° C. for 20 h. The mixture was partitioned between AcOEt and 1 N HCl, the organic layer was washed with brine, dried and evaporated. The residue was chromatographed on silica using CH₂Cl₂/MeOH (50:1) to give the title compound in 52% yield. MS: 480.5 (M+H)⁺.

Example 49

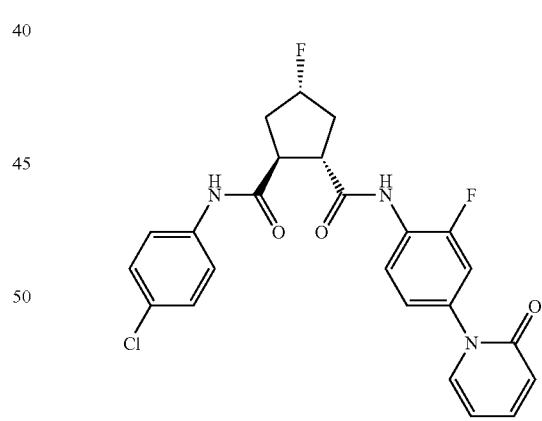

(1S,2S,4S)-4-Fluoro-cyclopentane-1,2-dicarboxylic acid 1-[(4-chloro-phenyl)-amide]2-{[2-fluoro-4-(2-oxo-2H-pyridin-1-yl)-phenyl]-amide}

Step 1: (1S,2S)-2-(4-Chloro-phenylcarbamoyl)-4-oxo-cyclopentanecarboxylic acid ethyl ester (49a)

Starting from 41c, the title compound was prepared in quantitative yield according to the procedure for example 3. MS: 310.0 (M+H)⁺.

Step 2: (1S,2S,4R)- and (1S,2S,4S)-2-(4-Chloro-phenylcarbamoyl)-4-hydroxy-cyclopentanecarboxylic acid ethyl ester (49b and 49c)

Starting from 49a, the title compounds were prepared according to the procedure for example 22. Separation of the epimers 49b and 49c was accomplished by chromatography on silica using $CH_2Cl_2$/MeOH (100:1). The first fraction afforded 49b in 49% yield. MS: 312.3 (M+H)$^+$. The second fraction gave 49c in 29% yield. MS: 312.3 (M+H)$^+$.

Step 3: (1S,2S,4S)-2-(4-Chloro-phenylcarbamoyl)-4-fluoro-cyclopentanecarboxylic acid ethyl ester (49d)

To a solution of 100 mg of 49b in 2 ml of $CH_2Cl_2$ was added at −60° C. 0.13 ml of a 50% solution of bis-(2-methoxyethyl)-aminosulfur trifluoride in THF and stirring was continued at −60° C. for 30 min. The solution was warmed to 20° C., washed with saturated aqueous $NaHCO_3$ and water, the organic layer was dried and evaporated. The residue was chromatographed on silica using heptane/AcOEt (6:1) to give the title compound in 70% yield. MS: 314.0 (M+H)$^+$.

Step 4: (1S,2S,4S)-2-(4-Chloro-phenylcarbamoyl)-4-fluoro-cyclopentanecarboxylic acid (49e)

Starting from 49d, the title compound was prepared in quantitative yield according to the procedure for example 1 and 2, step 3. MS: 284.1 (M−H)$^−$.

Step 5: (1S,2S,4S)-4-Fluoro-cyclopentane-1,2-dicarboxylic acid 1-[(4-chloro-phenyl)-amide]2-{[2-fluoro-4-(2-oxo-2H-pyridin-1-yl)-phenyl]-amide} (49)

Starting from 49e, the title compound was prepared in 50% yield according to the procedure for example 1 and 2, step 4. MS: 472.4 (M+H)$^+$.

Example 50

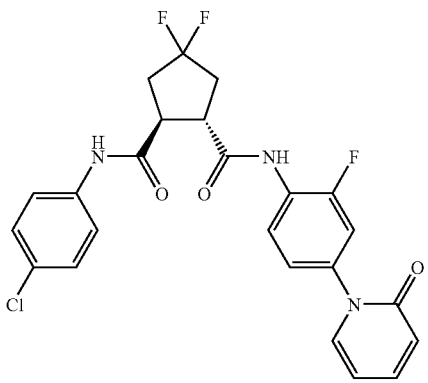

(1S,2S)-4,4-Difluoro-cyclopentane-1,2-dicarboxylic acid 1-[(4-chloro-phenyl)-amide]2-{[2-fluoro-4-(2-oxo-2H-pyridin-1-yl)-phenyl]-amide}

Step 1: (1S,2S)-2-(4-Chloro-phenylcarbamoyl)-4,4-difluoro-cyclopentanecarboxylic acid (50a)

To a solution of 52 mg of 49a in 1 ml of $CH_2Cl_2$ was added at 0° C. 0.40 ml of a 50% solution of bis-(2-methoxyethyl)-aminosulfur trifluoride in THF and stirring was continued at 20° C. for 30 min. The solution was washed with saturated aqueous $NaHCO_3$ and water, the organic layer was dried and evaporated. The residue was chromatographed on silica using heptane/AcOEt (7:1) to give the title compound in 31% yield. MS: 330.1 (M−H)$^−$.

Step 2: (1S,2S)-2-(4-Chloro-phenylcarbamoyl)-4,4-difluoro-cyclopentanecarboxylic acid (50b)

Starting from 50a, the title compound was prepared in quantitative yield according to the procedure for example 1 and 2, step 3. MS: 302.0 (M−H)$^−$.

Step 3: (1S,2S)-4,4-Difluoro-cyclopentane-1,2-dicarboxylic acid 1-[(4-chloro-phenyl)-amide]2-{[2-fluoro-4-(2-oxo-2H-pyridin-1-yl)-phenyl]-amide} (50c)

Starting from 50b, the title compound was prepared in 50% yield according to the procedure for example 1 and 2, step 4. MS: 488.0 (M−H)$^−$.

Example 51

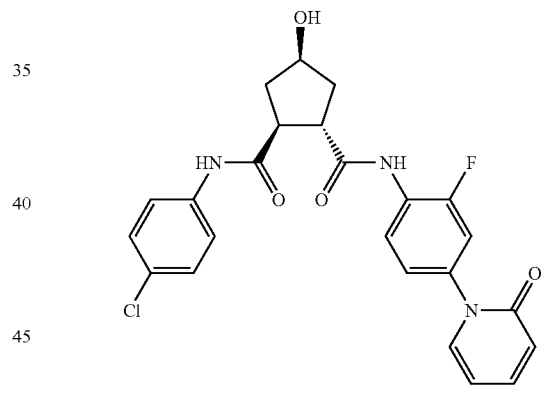

(1S,2S,4R)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide}

A suspension of 262 mg of 1-(4-amino-3-fluoro-phenyl)-1H-pyridin-2-one (prepared according to C. F. Bigge et al., patent application WO 2003045912) in 10 ml of toluene was treated at 20° C. with 0.64 ml of a 2 M $AlMe_3$ in heptane and stirring was continued for 1 h. 100 mg of 49b was added and the solution was stirred at reflux temperature for 1 h. The mixture was cooled to 20° C. and partitioned between 1 N HCl and AcOEt. The organic layer was washed with water, dried and evaporated. The residue was chromatographed on silica using $CH_2Cl_2$/MeOH (25:1) to give the title product in

Example 52

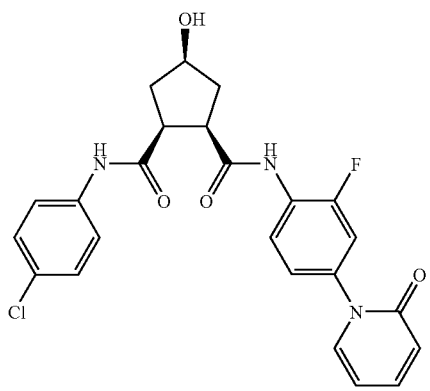

(1S,2S,4S)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide}

Starting from 49c, the title compound was prepared according to the procedure for example 51. MS: 470.4 (M+H)$^+$.

Example 53

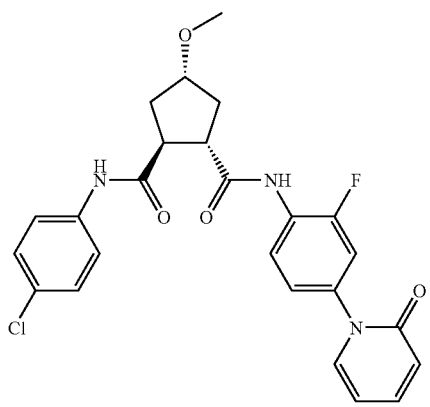

(1S,2S,4S)-4-Methoxy-cyclopentane-1,2-dicarboxylic acid 1-[(4-chloro-phenyl)-amide]2-{[2-fluoro-4-(2-oxo-2H-pyridin-1-yl)-phenyl]-amide}

Step 1: (1S,2S,4S)-2-(4-Chloro-phenylcarbamoyl)-4-methoxy-cyclopentanecarboxylic acid ethyl ester (53a)

A mixture of 50 mg of 49c, 263 mg of Ag$_2$O and 229 mg of MeI in 0.5 ml of MeCN and 0.2 ml of THF was stirred at 20° C. for 48 h. The suspension was filtered, the filtrate evaporated and the residue chromatographed on silica using heptane/AcOEt (3:1) to give the title compound in 23% yield. MS: 326.1 (M+H)$^+$.

73% yield. 470.5 (M+H)$^+$. The relative and absolute configuration was determined by an X-ray analysis of 51 complexed with factor Xa.

Step 2: (1S,2S,4S)-4-Methoxy-cyclopentane-1,2-dicarboxylic acid 1-[(4-chloro-phenyl)-amide]2-{[2-fluoro-4-(2-oxo-2H-pyridin-1-yl)-phenyl]-amide} (53)

Starting from 53a, the title compound was prepared according to the procedure for example 51. MS: 482.0 (M−H)$^-$.

Example 54

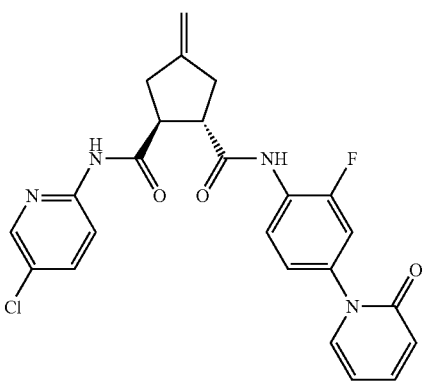

(1S,2S)-4-Methylene-cyclopentane-1,2-dicarboxylic acid 1-[(5-chloro-pyridin-2-yl)-amide]2-{[2-fluoro-4-(2-oxo-2H-pyridin-1-yl)-phenyl]-amide}

Step 1: (1S,2S)-2-[2-Fluoro-4-(2-oxo-2H-pyridin-1-yl)-phenylcarbamoyl]-4-methylene-cyclopentanecarboxylic acid ethyl ester (54a)

To a solution of 1.0 g of 41b in 10 ml of THF and 0.61 ml of N-methylmorpholine was added at −12° C. 0.72 ml of isobutyl chloroformate and stirring was continued at −15° C. for 30 min and at 20° C. for 1 h. The suspension obtained was added to a hot (60° C.) solution of 1.13 g of 1-(4-amino-3-fluoro-phenyl)-1H-pyridin-2-one (prepared according to C. F. Bigge et al., patent application WO 2003045912) in 8 ml of DMF and stirring was continued at 60° C. for 1 h. The reaction mixture was evaporated and the residue partitioned between 1 N HCl and AcOEt, the organic layer was washed with HCl and brine, dried and evaporated. The residue was chromatographed on silica using heptane/AcOEt (1:2) to give 1.28 g of the title compound 54a. MS: 385.0 (M+H)$^+$.

Step 2: (1S,2S)-4-Methylene-cyclopentane-1,2-dicarboxylic acid 1-[(5-chloro-pyridin-2-yl)-amide]2-{[2-fluoro-4-(2-oxo-2H-pyridin-1-yl)-phenyl]-amide}

A suspension of 69 mg of 2-amino-5-chloro-pyridine in 2 ml of toluene was treated at 20° C. with 0.26 ml of a 2 M AlMe$_3$ in heptane and stirring was continued for 1 h. 50 mg of 54a was added and the solution was stirred at reflux temperature for 2 h. The mixture was cooled to 20° C. and partitioned between 1 N HCl and AcOEt. The organic layer was washed with water, dried and evaporated. The residue was chromatographed on a thick layer silica plate using CH₂Cl₂/MeOH (9:1) to give the title product in 79% yield. MS: 467.1 (M+H)⁺.

Example 55

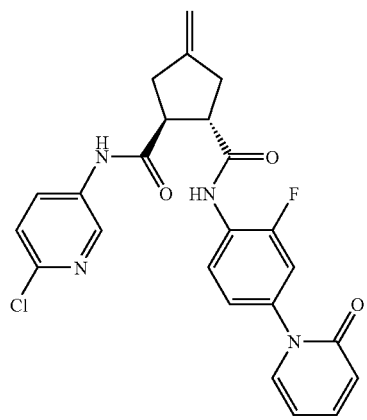

(1S,2S)-4-Methylene-cyclopentane-1,2-dicarboxylic acid 1-[(6-chloro-pyridin-3-yl)-amide]2-{[2-fluoro-4-(2-oxo-2H-pyridin-1-yl)-phenyl]-amide}

Starting from 54a and 5-amino-2-chloropyridine, the title compound was prepared in 29% yield according to the procedure for example 54, step 2. MS: 467.2 (M+H)⁺.

Example 56

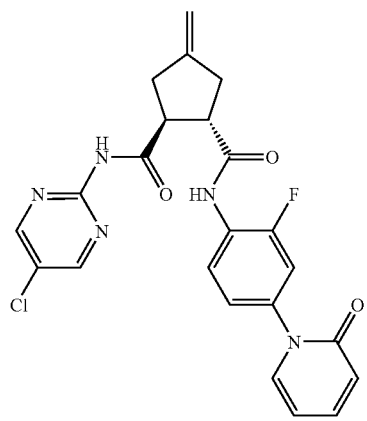

(1S,2S)-4-Methylene-cyclopentane-1,2-dicarboxylic acid 1-[(5-chloro-pyrimidin-2-yl)-amide]2-{[2-fluoro-4-(2-oxo-2H-pyridin-1-yl)-phenyl]-amide}

Starting from 54a and 2-amino-5-chloropyrimidine, the title compound was prepared in 6% yield according to the procedure for example 54, step 2. MS: 468.0 (M+H)⁺.

Example 57

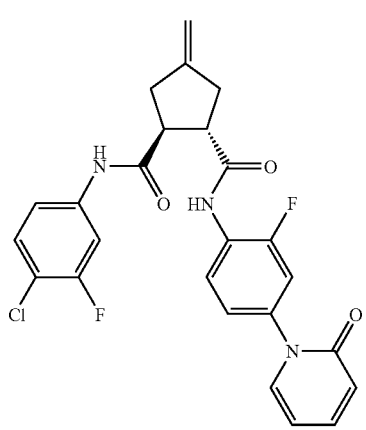

(1S,2S)-4-Methylene-cyclopentane-1,2-dicarboxylic acid 1-[(4-chloro-3-fluoro-phenyl)-amide]2-{[2-fluoro-4-(2-oxo-2H-pyridin-1-yl)-phenyl]-amide}

Starting from 54a and 4-chloro-3-fluoroaniline, the title compound was prepared in 28% yield according to the procedure for example 54, step 2. MS: 481.9 (M−H)⁻.

Example 58

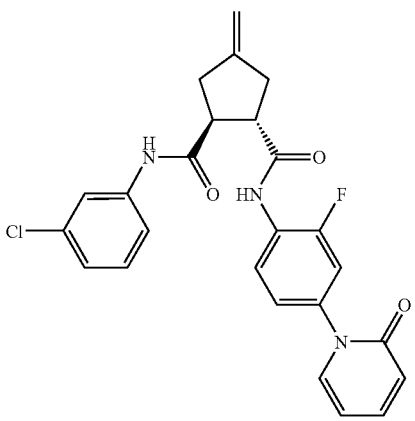

(1S,2S)-4-Methylene-cyclopentane-1,2-dicarboxylic acid 1-[(3-chloro-phenyl)-amide]2-{[2-fluoro-4-(2-oxo-2H-pyridin-1-yl)-phenyl]-amide}

Starting from 54a and 3-chloroaniline, the title compound was prepared in 58% yield according to the procedure for example 54, step 2. MS: 466.1 (M+H)⁺.

Example 59

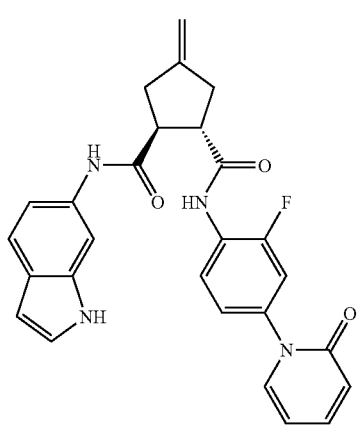

(1S,2S)-4-Methylene-cyclopentane-1,2-dicarboxylic acid 1-{[2-fluoro-4-(2-oxo-2H-pyridin-1-yl)-phenyl]-amide}2-[(1H-indol-6-yl)-amide]

Starting from 54a and 6-aminoindole, the titlecompound was prepared in 25% yield according to the procedure for example 54, step 2. MS: 471.3 (M+H)⁺.

Example 60

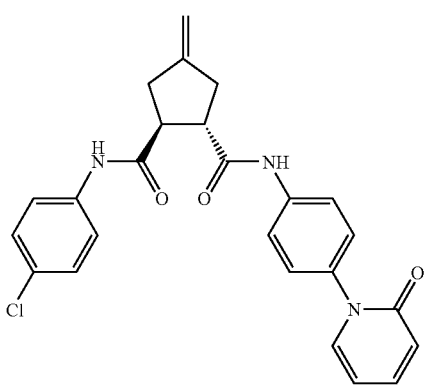

(1S,2S)-4-Methylene-cyclopentane-1,2-dicarboxylic acid 1-[(4-chloro-phenyl)-amide]2-{[4-(2-oxo-2H-pyridin-1-yl)-phenyl]-amide}

Starting from 41c and 1-(4-Amino-phenyl)-1H-pyridin-2-one (prepared according to C. F. Bigge et al., patent application WO 2003045912), the title compound was prepared in 23% yield according to the procedure for example 51. MS: 448.0 (M+H)⁺.

Example 61

(1S,2S)-4-Methylene-cyclopentane-1,2-dicarboxylic acid 1-[(4-chloro-phenyl)-amide]2-{[2-methyl-4-(2-oxo-2H-pyridin-1-yl)-phenyl]-amide}

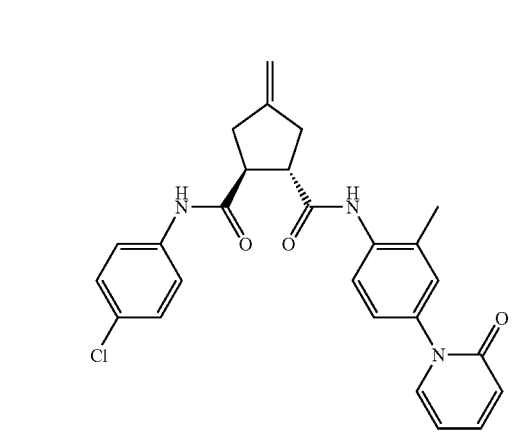

Starting from 41c and 1-(4-Amino-3-methyl-phenyl)-1H-pyridin-2-one (prepared according to C. F. Bigge et al., patent application WO 2003045912), the title compound was prepared in 48% yield according to the procedure for example 51. MS: 462.0 (M+H)⁺.

Example 62

(1S,2S)-4-Methylene-cyclopentane-1,2-dicarboxylic acid 1-[(4-chloro-phenyl)-amide]2-{[2-fluoro-4-(2-oxo-2H-pyrazin-1-yl)-phenyl]-amide}

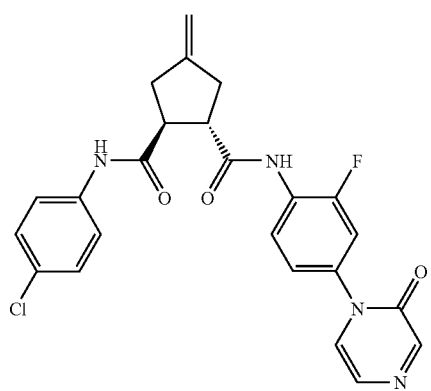

Starting from 41c and 1-(4-Amino-3-fluoro-phenyl)-1H-pyrazin-2-one (prepared according to C. F. Bigge et al., patent application WO 2003045912), the title compound was prepared in 54% yield according to the procedure for example 51. MS: 467.4 (M+H)⁺.

Example 63

(1S,2S)-4-Methylene-cyclopentane-1,2-dicarboxylic acid 1-[(4-chloro-phenyl)-amide]2-{[2-fluoro-4-(3-methyl-2-oxo-2H-pyridin-1-yl)-phenyl]-amide}

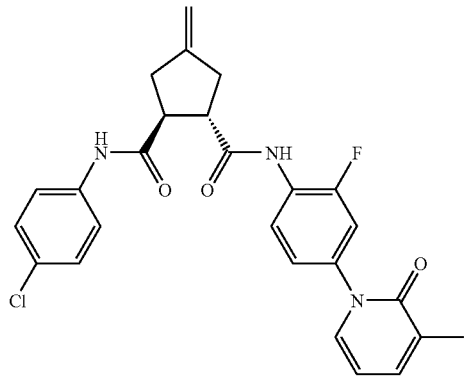

Starting from 41c and 1-(4-Amino-3-fluoro-phenyl)-3-methyl-1H-pyridin-2-one (prepared according to C. F. Bigge et al., patent application WO 2003045912), the title compound was prepared in 59% yield according to the procedure for example 51. MS: 480.0 (M+H)$^+$.

Example 64

(1S,2S)-4-Methylene-cyclopentane-1,2-dicarboxylic acid 1-[(4-chloro-phenyl)-amide]2-{[5-(2-methanesulfonyl-phenyl)-pyridin-2-yl]-amide}

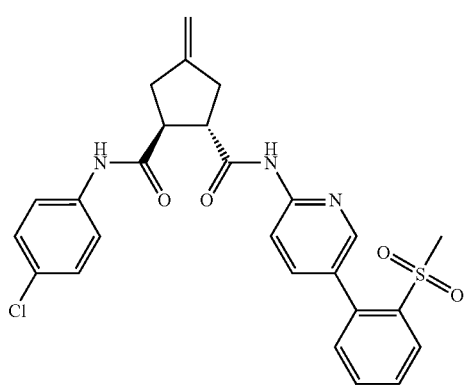

Starting from 41c and 5-(2-Methanesulfonyl-phenyl)-pyridin-2-ylamine (prepared according to R. A. Galemmo et al., patent application WO9857937), the title compound was prepared in quantitative yield according to the procedure for example 51. MS: 510.0 (M+H)$^+$.

Example 65

(1S,2S)-4-Methylene-cyclopentane-1,2-dicarboxylic acid 1-[(4-chloro-phenyl)-amide]2-{[4-(2-dimethylaminomethyl-imidazol-1-yl)-2-fluoro-phenyl]-amide}

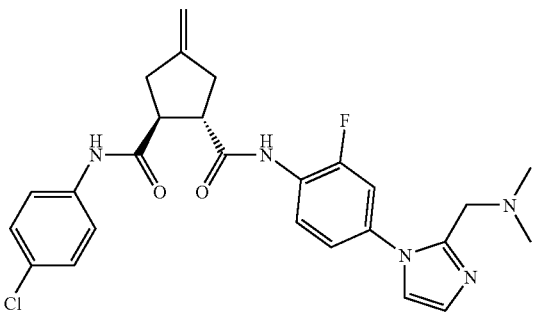

Starting from 41c and 4-(2-Dimethylaminomethyl-imidazol-1-yl)-2-fluoro-phenylamine (prepared according to M. L. Quan et al., patent application WO 2003047517), the title compound was prepared in 5% yield according to the procedure for example 51. MS: 496.1 (M+H)$^+$.

Example 66

(1S,2S)-4-Methylene-cyclopentane-1,2-dicarboxylic acid 1-[(4-chloro-phenyl)-amide]2-{[2-fluoro-4-(3-oxo-morpholin-4-yl)-phenyl]-amide}

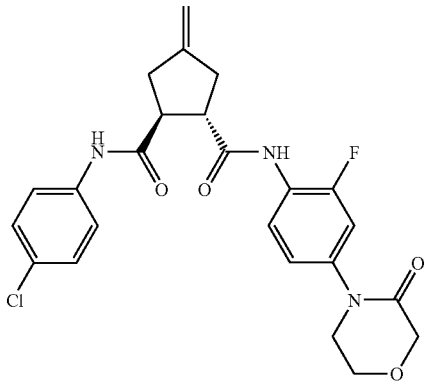

Starting from 41c and 4-(4-Amino-3-fluoro-phenyl)-morpholin-3-one (prepared according to C. F. Bigge et al., patent application WO 2003045912), the title compound was prepared in 53% yield according to the procedure for example 51. MS: 472.1 (M+H)$^+$.

Example 67

(1S,2S)-4-Methylene-cyclopentane-1,2-dicarboxylic acid 1-[(4-chloro-phenyl)-amide]2-{[4-(tetrahydro-1,1-dioxido-2H-1,2-thiazin-2-yl)-phenyl]-amide}

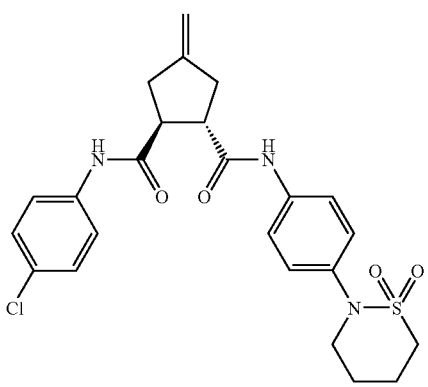

Starting from 41c and 4-(Tetrahydro-1,1-dioxido-2H-1,2-thiazin-2-yl)-phenylamine (prepared according to I. Zeid et al., Journal de la Societe Algerienne de Chimie 4(2), 171, 1994), the title compound was prepared in 79% yield according to the procedure for example 51. MS: 488.1 (M+H)$^+$.

Example 68

(1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid ethyl ester

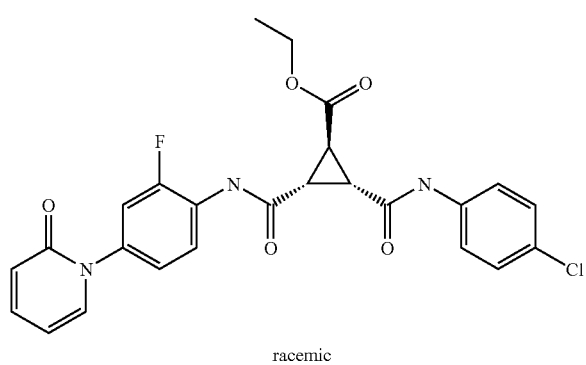

racemic

Step 1: (Z)-3-(4-chloro-phenylcarbamoyl)-acrylic acid

A solution of 29.3 g (300 mmol) of maleic anhydride in 500 ml of acetonitrile was treated portionwise with 40 g (310 mmol) of 4-chloroaniline and stirred at room temperature during 24 hrs. The thick precipitate that had formed was filtered off, washed with cold acetonitrile and dried i.v. to yield 65.7 g (97%) of the title compound. Yellow solid. MS: 226 (M+H)$^+$.

Step 2: 1-(4-chloro-phenyl)-pyrrole-2,5-dione

In Analogy to the procedure given in Mhaske et al., Synthesis, 2003, p863-870: A solution of 65 g (288 mmol) of (Z)-3-(4-chloro-phenylcarbamoyl)-acrylic acid in 300 ml of benzene was treated with 41.2 g (302 mmol) of zinc dichloride, dropwise with 90.1 ml (432 mmol) of bis(trimethylsilyl)amine and refluxed during 5 hrs. The mixture was poured into 300 ml of aqueous HCl (0.5 M). The aqueous phase was extracted with AcOEt, the combined organic phases were washed successively with saturated aqueous NaHCO$_3$ and brine, and finally dried over Na$_2$SO$_4$. Evaporation of the solvent gave 58 g (97%) of the title compound. Brown amorphous solid. MS: 208 (M+H)$^+$.

Step 3: (1RS, 5SR, 6R)-3-(4-chloro-phenyl)-2,4-dioxo-3-aza-bicyclo[3.1.0]hexane-6-carboxylic acid ethyl ester A solution of 19.4 g (93 mmol) of 1-(4-chloro-phenyl)-pyrrole-2,5-dione in 120 ml of xylene was treated with 19.4 ml (187 mmol) of ethyldiazoacetate and refluxed during 12 hrs. Evaporation of the solvent and chromatography on silica gel with toluene and then a gradient of toluene/AcOEt from 95:5 to 90:10 gave 9.5 g (35%) of the title compound. Off white solid. MS: 294 (M+H)$^+$.

Step 4: (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid ethyl ester A solution of 7 g (34 mmol) of 1-(4-amino-3-fluoro-phenyl)-1H-pyridin-2-one (prepared according to C. F. Bigge et al., patent application WO 2003045912) in 25 ml of THF was cooled to −78° C. and treated dropwise with 41 ml of a 1M lithium bis(trimethylsilyl)amide-solution in THF and stirred for 30 min. To this solution 9.5 g (32 mmol) of (1RS, 5SR, 6R)-3-(4-chloro-phenyl)-2,4-dioxo-3-aza-bicyclo[3.1.0]hexane-6-carboxylic acid ethyl ester were added portionwise and the mixture was allowed to reach room temperature within a few hours. The mixture was then poured into a diluted aqueous HCl-solution (ca. 0.2 M) and extracted with AcOEt. The combined organic phases were dried with Na$_2$SO$_4$. Evaporation of the solvent and chromatography on silica gel with dichloromethane and then with a gradient of dichloromethane/MeOH from 98:2 to 95:5 gave 4.1 g (24%) of the title compound. Light brown solid. MS: 496 (M−H)$^-$.

Example 69

(1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid

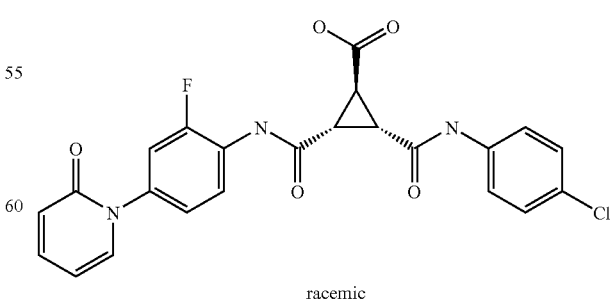

racemic

A solution of 80 mg (0.16 mmol) of (1RS,2RS,3SR)-2-(4-chloro-phenylcarbamoyl)-3-[2-fluoro-4-(2-oxo-2H-pyridin- 1-yl)-phenylcarbamoyl]-cyclopropanecarboxylic acid ethyl ester (example 68) in a mixture of 10 ml of THF and 10 ml of a 1M aqueous LiOH-solution was stirred during 2 hrs at room temperature. The mixture was poured into 50 ml of a aqueous HCl-solution (0.5 M), extracted with AcOEt and the combined organic phases were dried over $Na_2SO_4$. Evaporation of the solvent gave 65 mg (86%) of the title compound. Off-white solid. MS: 468 (M−H)⁻.

Example 70

(1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid ethyl ester

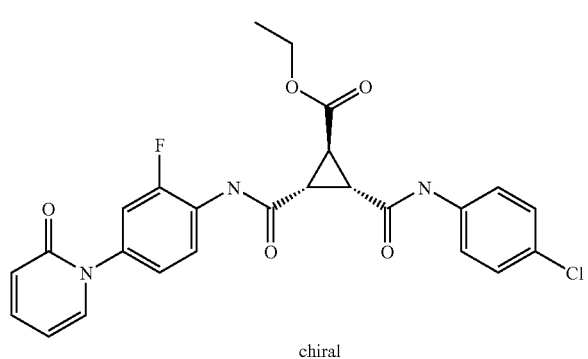

chiral

Chiral HPLC of 4 g (8.0 mmol) of (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid ethyl ester (example 68.4) on "Chiracel OD" with ethanol/heptane 1:4 gave ca. 1.5 g (37%) title compound as white solid, MS: 496 (M−H)⁻ along with ca. 1.5 g (37%) of the other enantiomer (1R,2S,3R)-2-(4-chloro-phenylcarbamoyl)-3-[2-fluoro-4-(2-oxo-2H-pyridin-1-yl)-phenylcarbamoyl]-cyclopropanecarboxylic acid ethyl ester, off-white solid. MS: 496 (M−H)⁻.

Example 71

(1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid

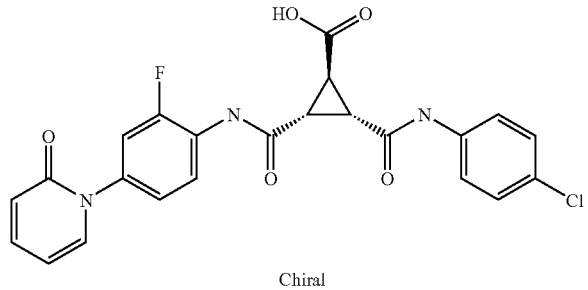

Chiral

In analogy to example 69, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid ethyl ester (example 70) was prepared the title compound. White solid. MS: 468 (M−H)⁻.

Example 72

(1RS,2SR,3SR)-3-(morpholine-4-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

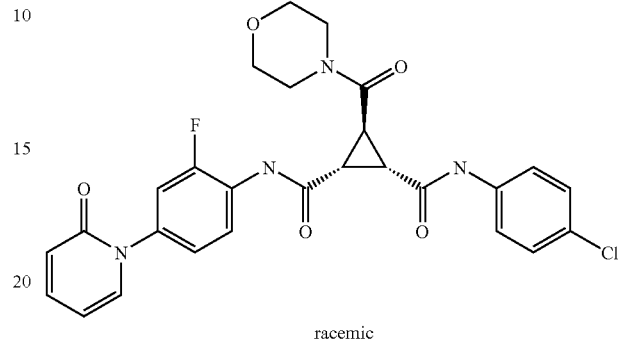

racemic

A solution of 27 mg (0.057 mmol) of (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69), 25 mg (0.29 mmol) of morpholine, 35 mg (0.34 mmol) of N-methylmorpholine, 2 mg (0.015 mmol) of 1-hydroxybenzotriazole in 1.2 ml of DMF was treated at room temperature with 17 mg (0.089 mmol) of 1-(3-dimethylaminopropyl)-3-ethylcarbodiimide hydrochloride and stirred for 48 hours at room temperature. The mixture was poured into 5 ml of a aqueous NaOH-solution (0.5 M), extracted with AcOEt and the combined organic phases were dried with $Na_2SO_4$. Evaporation of the solvent and chromatography on silica gel with dichloromethane/MeOH 98:2 gave 28 mg (90%) of the title compound. Brown solid. MS: 537 (M−H)⁻.

Example 73

(1R,2S,3S)-3-(morpholine-4-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

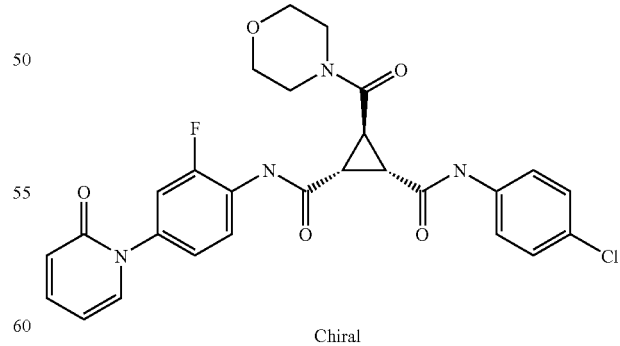

Chiral

In analogy to example 72, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid (example 72) was prepared the title compound. White solid. MS: 539 (M+H⁺).

Example 74

(1RS,2SR,3SR)-3-(3-hydroxy-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)phenyl]amide}

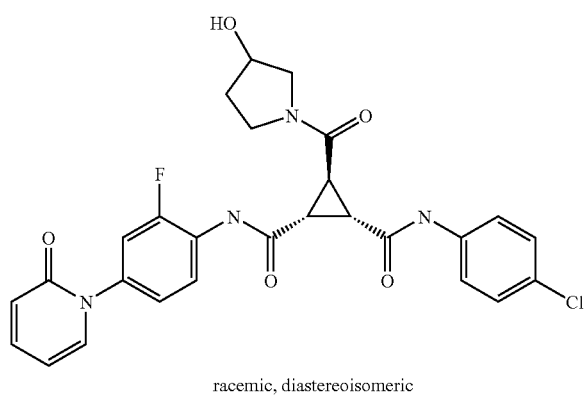

racemic, diastereoisomeric

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and racemic 3-hydroxypyrrolidine was prepared the titlecompound (racemic mixture of diastereomers). White solid. MS: 539 (M+H)$^+$.

Example 75

(1S,2S,4R)-4-Fluoro-cyclopentane-1,2-dicarboxylic acid 1-[(5-chloro-pyridin-2-yl)-amide]2-{[2-fluoro-4-(2-oxo-2H-pyridin-1-yl)-phenyl]-amide}

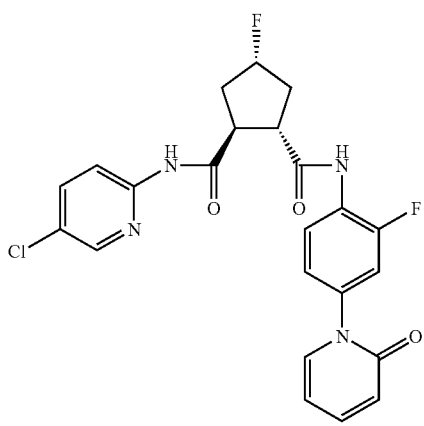

Step 1: (1S,2S)-2-(5-Chloro-pyridin-2-ylcarbamoyl)-4-methylene-cyclopentanecar-boxylic acid ethyl ester (75a)

Starting from 41b, the title compound was prepared in 48% yield according to the procedure for example 1 and 2, step 2 using 2-amino-5-chloropyridine. MS: 309.1 (M+H)$^+$.

Step 2: (1S,2S)-2-(5-Chloro-pyridin-2-ylcarbamoyl)-4-oxo-cyclopentanecarboxylic acid ethyl ester (75b)

Starting from 75a, the title compound was prepared in quantitative yield according to the procedure for example 3. MS: 311.1 (M+H)$^+$.

Step 3: (1S,2S,4R)- and (1S,2S,4S)-2-(5-Chloro-pyridin-2-ylcarbamoyl)-4-hydroxy-cyclopentanecarboxylic acid ethyl ester (75c and 75d)

Starting from 75b, the title compounds were prepared according to the procedure for example 22. Separation of the epimers 75c and 75d was accomplished by chromatography on silica using diethylether. The first fraction afforded 75c in 40% yield. MS: 313.1 (M+H)$^+$. The second fraction gave 75d in 17% yield. MS: 3131 (M+H)$^+$.

Step 4: (1S,2S,4S)-2-(5-Chloro-pyridin-2-ylcarbamoyl)-4-fluoro-cyclopentanecar-boxylic acid ethyl ester (75e)

Starting from 75c, the title compound was prepared in 81% yield according to the procedure for example 49, step 3. MS: 315.3 (M+H)$^+$.

Step 5: (1S,2S,4S)-2-(5-Chloro-pyridin-2-ylcarbamoyl)-4-fluoro-cyclopentanecar-boxylic acid (75f)

Starting from 75e, the title compound was prepared in 87% yield according to the procedure for example 1 and 2, step 3. MS: 287.1 (M+H)$^+$.

Step 6: (1S,2S,4R)-4-Fluoro-cyclopentane-1,2-dicarboxylic acid 1-[(5-chloro-pyridin-2-yl)-amide]2-{[2-fluoro-4-(2-oxo-2H-pyridin-1-yl)-phenyl]-amide} (75g)

Starting from 75f, the title compound was prepared in 45% yield according to the procedure for example 1 and 2, step 4. MS: 473.0 (M+H)$^+$.

Example 76

(1S,2S,4S)-4-Fluoro-cyclopentane-1,2-dicarboxylic acid 1-[(5-chloro-pyridin-2-yl)-amide]2-{[2-fluoro-4-(2-oxo-2H-pyridin-1-yl)-phenyl]-amide}

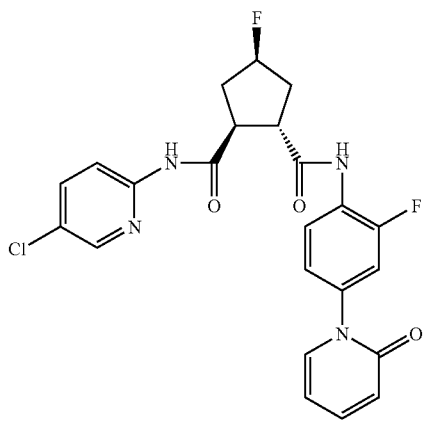

Step 1: (1S,2S,4R)-2-(5-Chloro-pyridin-2-ylcarbamoyl)-4-fluoro-cyclopentanecar-boxylic acid ethyl ester (76a)

Starting from 75d, the title compound was prepared in 60% yield according to the procedure for example 49, step 3. MS: 315.0 (M+H)+.

Step 2: (1S,2S,4R)-2-(5-Chloro-pyridin-2-ylcarbamoyl)-4-fluoro-cyclopentanecar-boxylic acid (76b)

Starting from 76a, the title compound was prepared in 60% yield according to the procedure for example 1 and 2, step 3. MS: 287.0 (M+H)+.

Step 3: (1S,2S,4S)-4-Fluoro-cyclopentane-1,2-dicarboxylic acid 1-[(5-chloro-pyridin-2-yl)-amide]2-{[2-fluoro-4-(2-oxo-2H-pyridin-1-yl)-phenyl]-amide} (76c)

Starting from 76b, the title compound was prepared in 70% yield according to the procedure for example 1 and 2, step 4. MS: 473.2 (M+H)+.

Example 77

(1S,2S,4R)-4-Fluoro-cyclopentane-1,2-dicarboxylic acid 1-[(5-chloro-pyridin-2-yl)-amide]2-{[2-methyl-4-(2-oxo-2H-pyridin-1-yl)-phenyl]-amide}

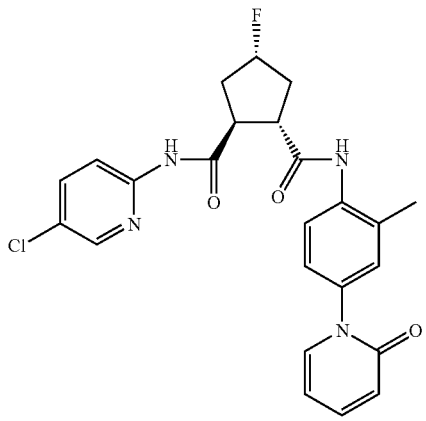

Starting from 75f and 1-(4-amino-3-methyl-phenyl)-1H-pyridin-2-one (prepared according to C. F. Bigge et al., patent application WO 2003045912), the title compound was prepared in 49% yield according to the procedure for example 1 and 2, step 4. MS: 469.0 (M+H)+.

Example 78

(1S,2S,4R)-4-Fluoro-cyclopentane-1,2-dicarboxylic acid 1-[(5-chloro-pyridin-2-yl)-amide]2-{[2-fluoro-4-(2-oxo-2H-pyrazin-1-yl)-phenyl]-amide}

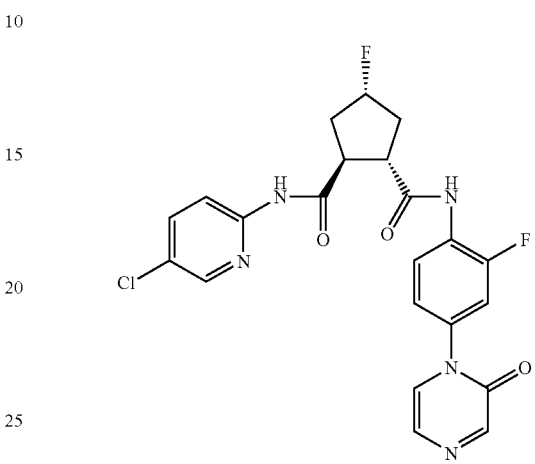

Starting from 75f and 1-(4-amino-3-fluoro-phenyl)-1H-pyrazin-2-one (prepared according to C. F. Bigge et al., patent application WO 2003045912), the title compound was prepared in 32% yield according to the procedure for example 1 and 2, step 4. MS: 473.9 (M+H)+.

Example 79

(1S,2S,4R)-4-Fluoro-cyclopentane-1,2-dicarboxylic acid 1-[(5-chloro-pyridin-2-yl)-amide]2-{[2-fluoro-4-(3-oxo-morpholin-4-yl)-phenyl]-amide}

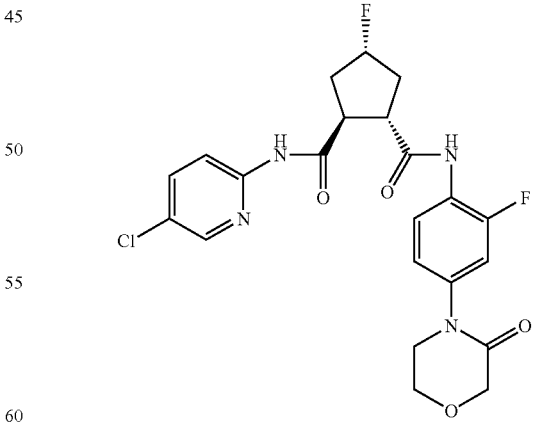

Starting from 75f and 4-(4-amino-3-fluoro-phenyl)-morpholin-3-one (prepared according to C. F. Bigge et al., patent application WO 2003045912), the title compound was prepared in 43% yield according to the procedure for example 1 and 2, step 4. MS: 479.0 (M+H)+.

Example 80

(1S,2S,4R)-4-Fluoro-cyclopentane-1,2-dicarboxylic acid 1-[(5-chloro-pyridin-2-yl)-amide]2-{[4-(3-oxo-morpholin-4-yl)-phenyl]-amide}

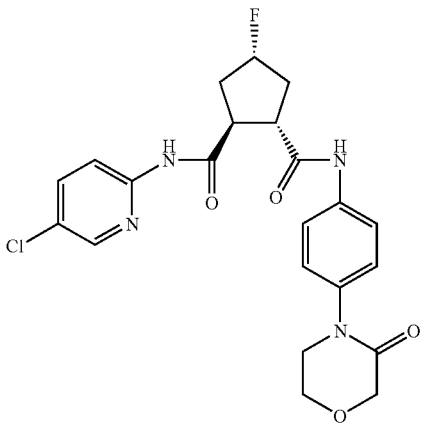

Starting from 75f and 4-(4-amino-phenyl)-morpholin-3-one (prepared according to C. Thomas et al., patent application WO 2005026135), the title compound was prepared in 57% yield according to the procedure for example 1 and 2, step 4. MS: 461.0 (M+H)$^+$.

Example 81

(1SR,2RS,3SR)-3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}

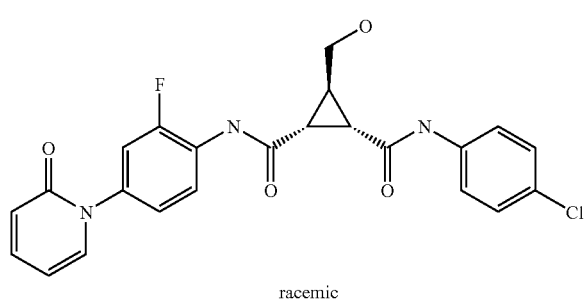

racemic

A solution of 20 mg (0.04 mmol) of (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid ethyl ester (example 68) in 0.5 ml of THF was treated with 38 mg (0.08 mmol) LiAlH$_4$ and stirred at RT during 1 hr. The mixture was treated with icy water, extracted with AcOEt and the combined organic phases were dried over Na$_2$SO$_4$. Filtration, evaporation of the solvent and chromatography on silica gel with dichloromethane/methanol 10:1 gave 6 mg (34%) of (1SR,2RS,3SR)-3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}. Light brown semi-solid. MS: 456 (M+H)$^+$.

Example 82

(1SR,2SR,3RS)-cyclopropane-1,2,3-tricarboxylic acid 1-amide 2-[(4-chloro-phenyl)-amide]3-{[2-fluoro-4-(2-oxo-2H-pyridin-1-yl)-phenyl]-amide}

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and ammonium chloride was prepared (1SR,2SR,3RS)-cyclopropane-1,2,3-tricarboxylic acid 1-amide 2-[(4-chloro-phenyl)-amide]3-{[2-fluoro-4-(2-oxo-2H-pyridin-1-yl)-phenyl]-amide}. Light yellow solid. MS: 467 (M−H)$^-$.

Example 83

(1SR,2RS,3SR)-3-(1-hydroxy-1-methyl-ethyl)-cyclopropane-1,2-dicarboxylic acid 1-[(4-chloro-phenyl)-amide]2-{[2-fluoro-4-(2-oxo-2H-pyridin-1-yl)-phenyl]-amide}

A solution of 43 mg (0.09 mmol) of (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid ethyl ester (example 68) in 1 ml of THF was cooled to −78° and treated with 0.14 ml (0.43 mmol) of a methylmagnesiumchloride solution in ether. The mixture was allowed to reach RT and stirred for 5 hrs. The mixture was treated with saturated aqueous NH$_4$Cl solution and extracted with AcOEt. Drying of the combined organic phases over Na$_2$SO$_4$, filtration, evaporation of the solvent and chromatography on silica gel with dichloromethane/methanol 95:5 gave 21 mg (50%) of (1SR, 2RS,3SR)-3-(1-hydroxy-1-methyl-ethyl)-cyclopropane-1,2- dicarboxylic acid 1-[(4-chloro-phenyl)-amide]2-{[2-fluoro-4-(2-oxo-2H-pyridin-1-yl)-phenyl]-amide}. Yellow solid. MS: 484 (M+H)+.

Example 84

(1SR,2RS,3SR)-3-(1-ethyl-1-hydroxy-propyl)-cyclopropane-1,2-dicarboxylic acid 1-[(4-chloro-phenyl)-amide]2-{[2-fluoro-4-(2-oxo-2H-pyridin-1-yl)-phenyl]-amide}

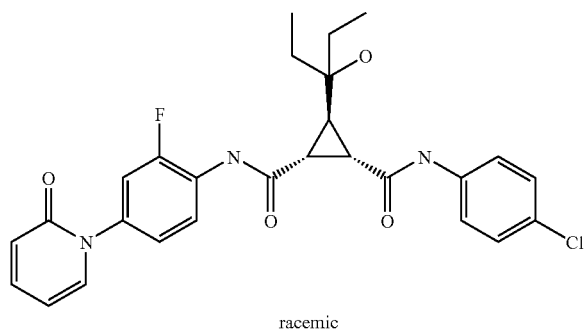

racemic

In analogy to example 83, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid ethyl ester (example 68) and ethylmagnesium bromide was prepared (1SR,2RS,3SR)-3-(1-ethyl-1-hydroxy-propyl)-cyclopropane-1,2-dicarboxylic acid 1-[(4-chloro-phenyl)-amide]2-{[2-fluoro-4-(2-oxo-2H-pyridin-1-yl)-phenyl]-amide}. Yellow solid. MS: 512 (M+H)+.

Example 85

(1RS,2SR,3SR)-3-(piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

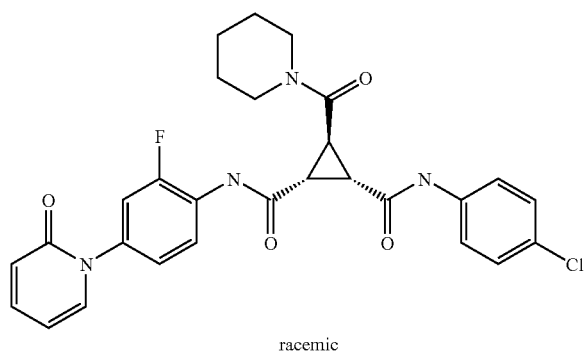

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and piperidine was prepared (1RS,2SR,3SR)-3-(piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown viscous oil. MS: 537 (M+H)+.

Example 86

(1RS,2SR,3SR)-cyclopropane-1,2,3-tricarboxylic acid 1-[(4-chloro-phenyl)-amide]2-dimethylamide 3-{[2-fluoro-4-(2-oxo-2H-pyridin-1-yl)-phenyl]-amide}

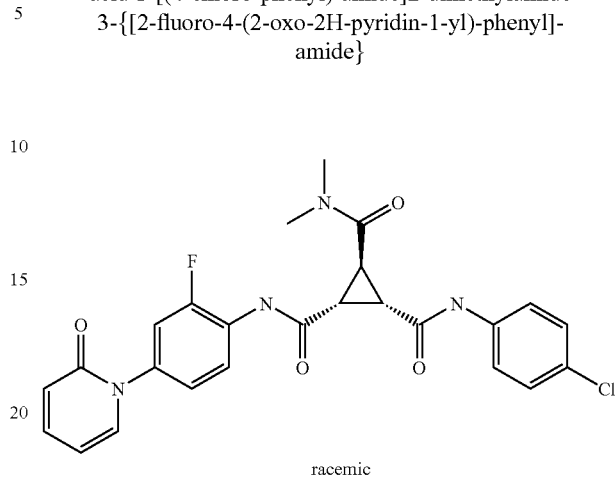

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and dimethylamine hydrochloride was prepared (1RS,2SR,3SR)-cyclopropane-1,2,3-tricarboxylic acid 1-[(4-chloro-phenyl)-amide]2-dimethylamide 3-{[2-fluoro-4-(2-oxo-2H-pyridin-1-yl)-phenyl]-amide}. Off-white viscous oil. MS: 497 (M+H)+.

Example 87

(1RS,2SR,3SR)-cyclopropane-1,2,3-tricarboxylic acid 1-[(4-chloro-phenyl)-amide]3-{[2-fluoro-4-(2-oxo-2H-pyridin-1-yl)-phenyl]-amide}2-(methyl-propyl-amide)

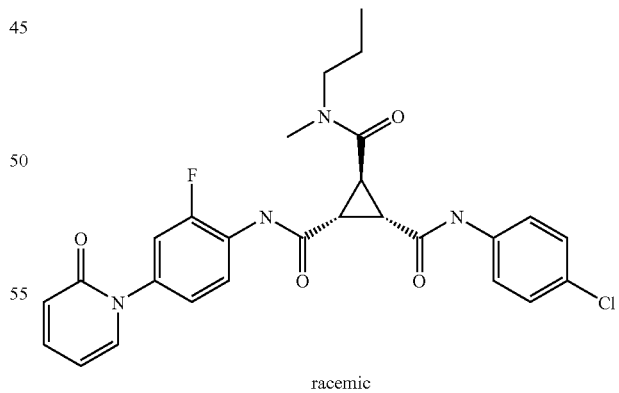

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and methylpropylamine was prepared (1RS,2SR,3SR)-cyclopropane-1,2,3-tricarboxylic acid 1-[(4-chlorophenyl)-amide]3-{[2-fluoro-4-(2-oxo-2H-pyridin-1-yl)-phenyl]-amide}2-(methyl-propyl-amide). Light yellow solid. MS: 525 (M+H)+.

Example 88

(1RS,2SR,3SR)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-hydroxy-ethyl)-methyl-amide]

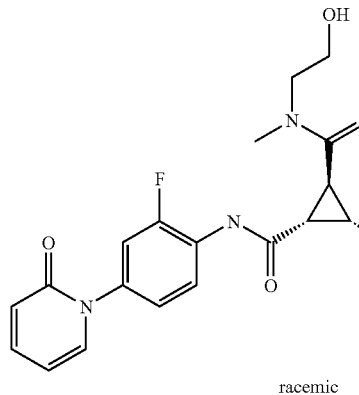

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and methylamino ethanol was prepared (1RS,2SR,3SR)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-hydroxy-ethyl)-methyl-amide]. Brown viscous oil. MS: 527 (M+H)+.

Example 89

(1RS,2SR,3SR)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-methoxy-ethyl)-methyl-amide]

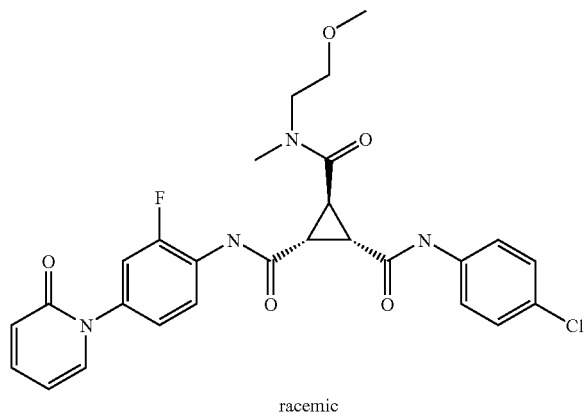

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and N-(2-methoxyethyl)methylamine was prepared (1RS,2SR,3SR)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-methoxy-ethyl)-methyl-amide].Light yellow solid. MS: 539 (M–H)−.

Example 90

(1SR,2RS,3SR)-cyclopropane-1,2,3-tricarboxylic acid 1-(carbamoylmethyl-methyl-amide) 2-[(4-chloro-phenyl)-amide]3-{[2-fluoro-4-(2-oxo-2H-pyridin-1-yl)-phenyl]-amide}

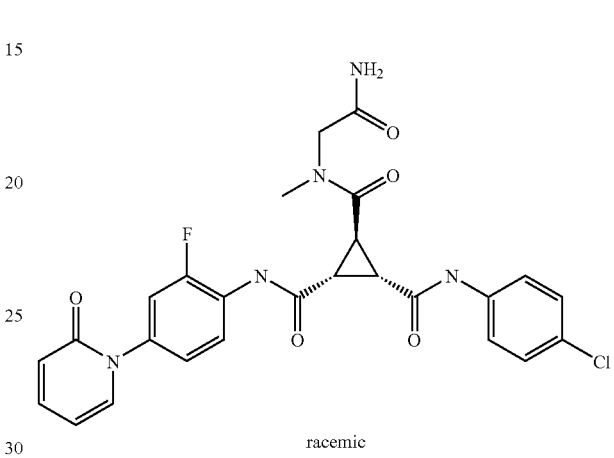

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and (methylamino)acetamide was prepared (1SR,2RS,3SR)-cyclopropane-1,2,3-tricarboxylic acid 1-(carbamoylmethyl-methyl-amide) 2-[(4-chloro-phenyl)-amide]3-{[2-fluoro-4-(2-oxo-2H-pyridin-1-yl)-phenyl]-amide}. Brown solid. MS: 538 (M–H)−.

Example 91

(1RS,2SR,3SR)-3-(azepane-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

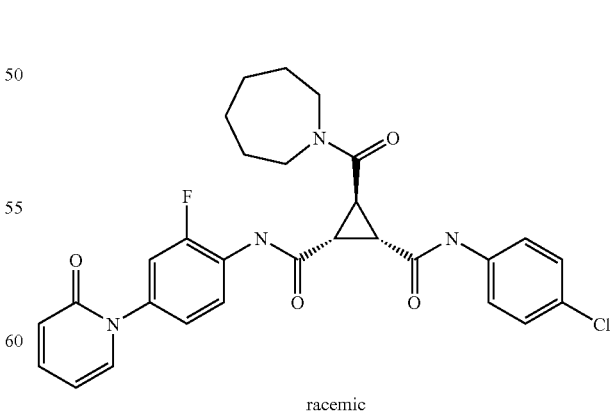

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and hexamethyleneimine was prepared (1RS,2SR, 3SR)-3-(azepane-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Brown solid. MS: 550 (M–H)⁻.

Example 92

(1RS,2SR,3SR)-3-(3-oxo-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

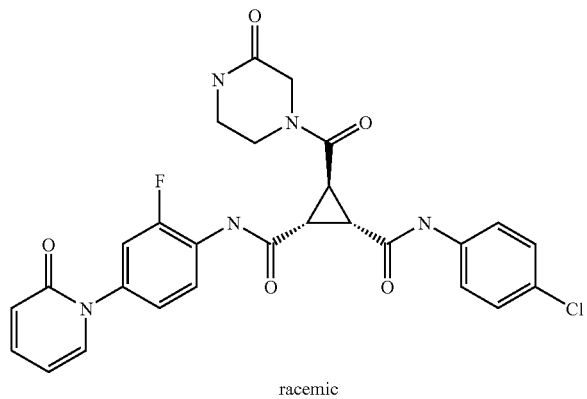

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and piperazine-2-one was prepared (1RS,2SR, 3SR)-3-(3-oxo-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Brown solid. MS: 552 (M+H)⁺.

Example 93

(1RS,2SR,3SR)-3-(3,3-difluoro-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

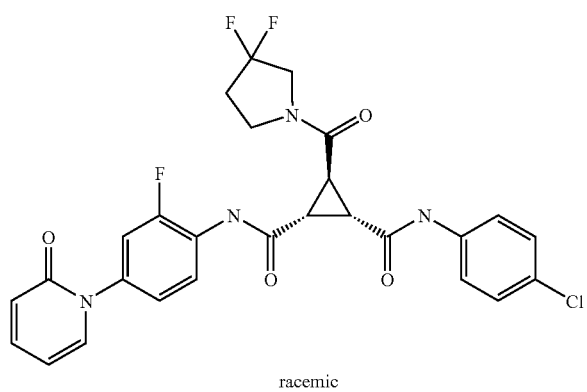

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 3,3-difluoro-pyrrolidine hydrochloride was prepared(1RS,2SR,3SR)-3-(3,3-difluoro-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Brown solid. MS: 552 (M+H)⁺.

Example 94

(1SR,2SR,3RS)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2,2,2-trifluoro-ethyl)-amide]

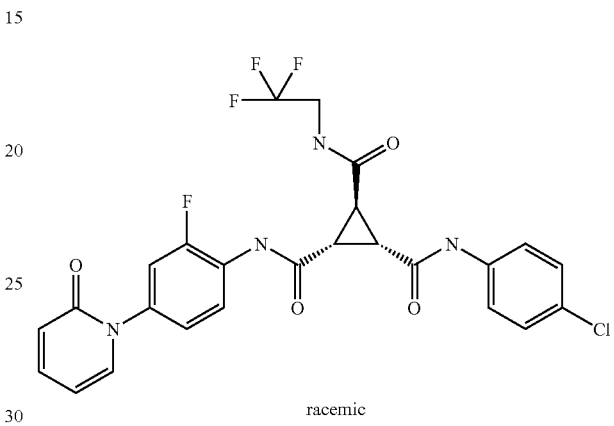

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and trifluorethylamine was prepared (1SR,2SR, 3RS)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2,2,2-trifluoro-ethyl)-amide]. Off-white solid. MS: 551 (M+H)⁺.

Example 95

(1RS,2SR,3SR)-cyclopropane-1,2,3-tricarboxylic acid 1-[(4-chloro-phenyl)-amide]2-diethylamide 3-{[2-fluoro-4-(2-oxo-2H-pyridin-1-yl)-phenyl]-amide}

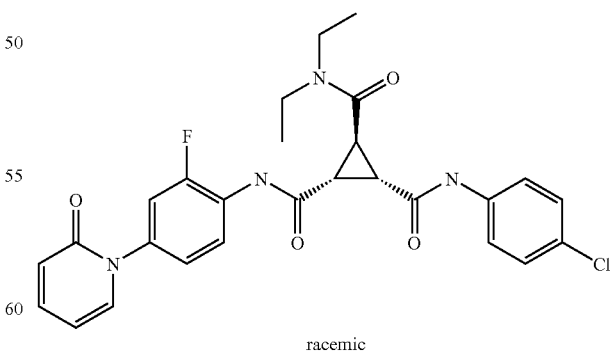

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and diethylamine hydrochloride was prepared (1RS,2SR,3SR)-cyclopropane-1,2,3-tricarboxylic acid 1-[(4-chloro-phenyl)-amide]2-diethylamide 3-{[2-fluoro-4-(2-oxo-2H-pyridin-1-yl)-phenyl]-amide}. Off-white solid. MS: 525 (M+H)+.

Example 96

(1RS,2SR,3SR)-3-(pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

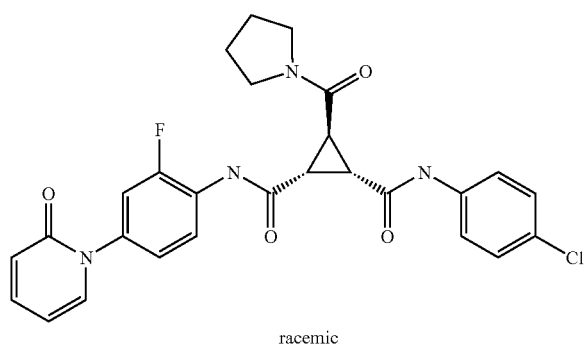

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and pyrrolidine was prepared (1RS,2SR,3SR)-3-(pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown solid. MS: 523 (M+H)+.

Example 97

(1RS,2SR,3SR)-3-(azetidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

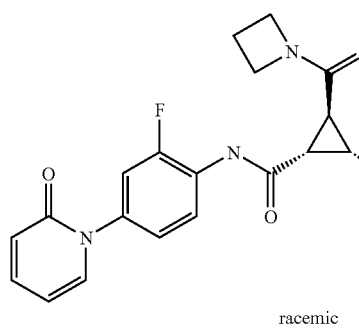

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and azetidine was prepared (1RS,2SR,3SR)-3-(azetidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Brown solid. MS: 509 (M+H)+.

Example 98

(1SR,2SR,3RS)-cyclopropane-1,2,3-tricarboxylic acid 1-[(4-chloro-phenyl)-amide]2-ethylamide 3-{[2-fluoro-4-(2-oxo-2H-pyridin-1-yl)-phenyl]-amide}

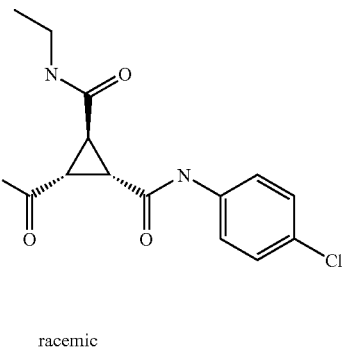

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and ethylamine hydrochloride was prepared (1SR,2SR,3RS)-cyclopropane-1,2,3-tricarboxylic acid 1-[(4-chloro-phenyl)-amide]2-ethylamide 3-{[2-fluoro-4-(2-oxo-2H-pyridin-1-yl)-phenyl]-amide}. Off-white solid. MS: 497 (M+H)+.

Example 99

(1SR,2SR,3RS)-cyclopropane-1,2,3-tricarboxylic acid 1-[(4-chloro-phenyl)-amide]2-[(2,2-difluoro-ethyl)-amide]3-{[2-fluoro-4-(2-oxo-2H-pyridin-1-yl)-phenyl]-amide}

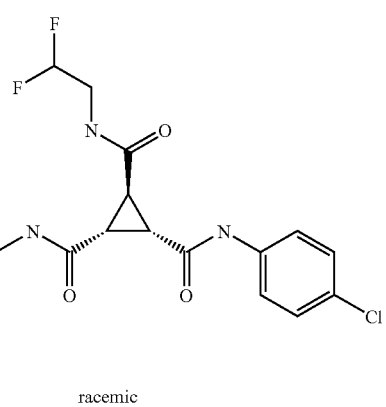

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 2,2-difluoroethylamine hydrochloride was prepared (1SR,2SR,3RS)-cyclopropane-1,2,3-tricarboxylic acid 1-[(4-chloro-phenyl)-amide]2-[(2,2-difluoro-ethyl)-

Example 100

(1RS,2SR,3SR)-3-phenyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

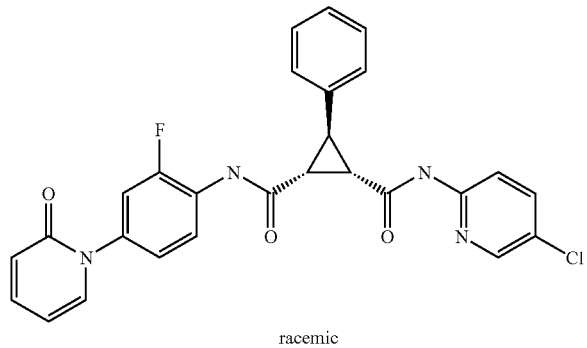

racemic

Step 1:
A mixture of 100 mg (0.48 mmol) of 3-phenyl-cyclopropane-cis-1,2-dicarboxylic acid (purchased from Rarechem, cat.-No: AQ C30042), 109 mg (0.53 mmol) of 1-(4-amino-3-fluoro-phenyl)-1H-pyridin-2-one (prepared according to C. F. Bigge et al., patent application WO 2003045912), 0.32 ml (2.9 mmol) of 4-methylmorpholine 13 mg (0.1 mmol) of 1-hydroxybenzotriazole in DMF was treated with 139 (073 mmol) of 1-(3-dimethylaminopropyl)-3-ethylcarbodiimide hydrochloride and stirred during 12hrs at RT. The mixture was poured into 5 ml of a 0.5 M aqueous HCl-solution, extracted with AcOEt and the combined organic phases were dried over $Na_2SO_4$. Filtration, evaporation of the solvent gave 140 mg (74%) of (1RS,2SR,3SR)-2-[2-fluoro-4-(2-oxo-2H-pyridin-1-yl)-phenylcarbamoyl]-3-phenyl-cyclopropanecarboxylic acid. Light yellow oil. MS: 391 (M–H)⁻.

Step 2:
A solution of 140 mg (0.36 mmol) of (1RS,2SR,3SR)-2-[2-fluoro-4-(2-oxo-2H-pyridin-1-yl)-phenylcarbamoyl]-3-phenyl-cyclopropanecarboxylic acid in 5 ml of methanol was treated at 0° C. with ca. 0.1 ml of thionylchloride and left to stir overnight at RT. Evaporation of the solvent gave 160 mg of (1RS,2SR,3SR)-2-[2-fluoro-4-(2-oxo-2H-pyridin-1-yl)-phenylcarbamoyl]-3-phenyl-cyclopropanecarboxylic acid methylester. Light yellow oil. MS: 405 (M–H)⁻.

Step 3:
A solution of 105 mg (0.82 mml) of 2-amino-5-chloropyridine in 2.5 ml of dioxane was treated with 0.41 ml of a 2 M $AlMe_3$-solution in hexane (0.82 mmol) and stirred at RT during two hours. To this solution was added a solution of 85 mg (0.2 mmol) of (1RS,2SR,3SR)-2-[2-fluoro-4-(2-oxo-2H-pyridin-1-yl)-phenylcarbamoyl]-3-phenyl-cyclopropanecarboxylic acid methylester in 2.5 ml of dioxane. The resulting mixture was stirred at 90° C. during 64 hrs, treated with 0.8 ml of water, diluted with 5 ml of dioxane and dried over $Na_2SO_4$. Filtration, evaporation of the solvent and chromatography on silica gel with heptane/AcOEt 4:1 gave 53 mg (52%) of (1RS,2SR,3SR)-3-phenyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Light brown crystalline. MS: 504 (M+H)⁺.

Example 101

(1RS,2SR,3SR)-3-(3-hydroxy-azetidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

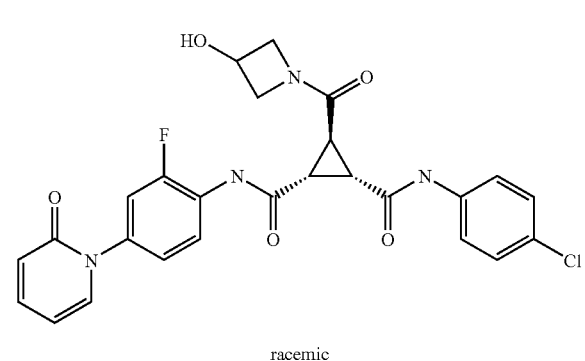

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 3-hydroxyazetidine was prepared (1RS,2SR,3SR)-3-(3-hydroxy-azetidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown oil. MS: 525,M+H)⁺.

Example 102

(1RS,2SR,3SR)-3-(3-hydroxy-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

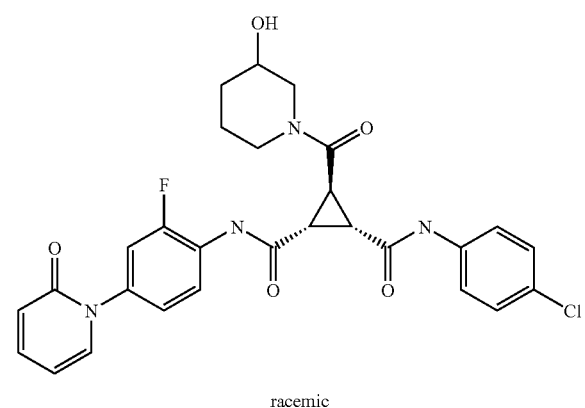

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 3-piperidine was prepared (1RS,2SR,3SR)-3-(3-hydroxy-piperidine-1-carbonyl)-cyclopropane-1,2- dicarboxylic acid 1-[(4-chloro-phenyl)-amide]2-{[2-fluoro-4-(2-oxo-2H-pyridin-1-yl)-phenyl]-amide}. Light brown oil. MS: 553 (M+H)⁺.

Example 103

(1RS,2SR,3SR)-cyclopropane-1,2,3-tricarboxylic acid 1-[(4-chloro-phenyl)-amide]2-[(2,3-dihydroxy-propyl)-methyl-amide]3-{[2-fluoro-4-(2-oxo-2H-pyridin-1-yl)-phenyl]-amide}

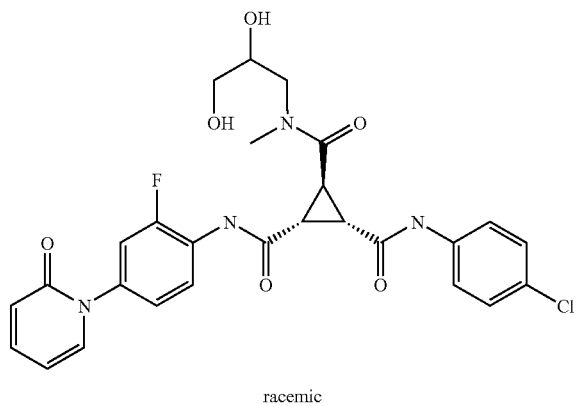

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 3-methylamino-1,2-propanediol was prepared (1RS,2SR,3SR)-cyclopropane-1,2,3-tricarboxylic acid 1-[(4-chloro-phenyl)-amide]2-[(2,3-dihydroxy-propyl)-methyl-amide]3-{[2-fluoro-4-(2-oxo-2H-pyridin-1-yl)-phenyl]-amide}. Light brown oil. MS: 557 (M+H)⁺.

Example 104

(1RS,2SR,3SR)-3-(4-hydroxy-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

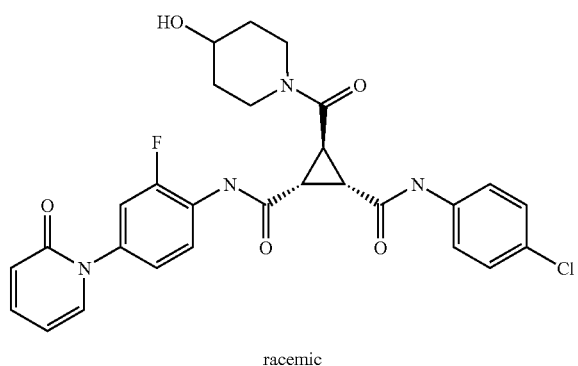

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 4-hydroxypiperidine was prepared (1RS,2SR,3SR)-3-(4-hydroxy-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow crystalline. 554 (M+H)⁺.

Example 105

(1SR,2RS,3SR)-3-phenyl-cyclopropane-1,2-dicarboxylic acid 1-[(4-chloro-phenyl)-amide]2-{[2-fluoro-4-(2-oxo-2H-pyridin-1-yl)-phenyl]-amide}

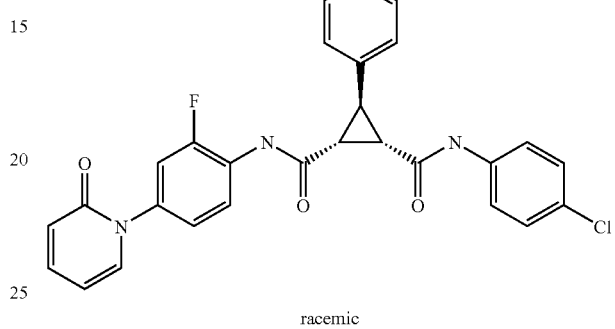

racemic

In analogy to example 100, step 3, from 4-chloroaniline and (1RS,2SR,3SR)-2-[2-fluoro-4-(2-oxo-2H-pyridin-1-yl)-phenylcarbamoyl]-3-phenyl-cyclopropanecarboxylic acid methylester was prepared (1SR,2RS,3SR)-3-phenyl-cyclopropane-1,2-dicarboxylic acid 1-[(4-chloro-phenyl)-amide] 2-{[2-fluoro-4-(2-oxo-2H-pyridin-1-yl)-phenyl]-amide}. Light brown crystalline. MS: 502 (M+H)⁺.

Example 106

(1RS,2SR,3SR)-3-(4-methyl-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

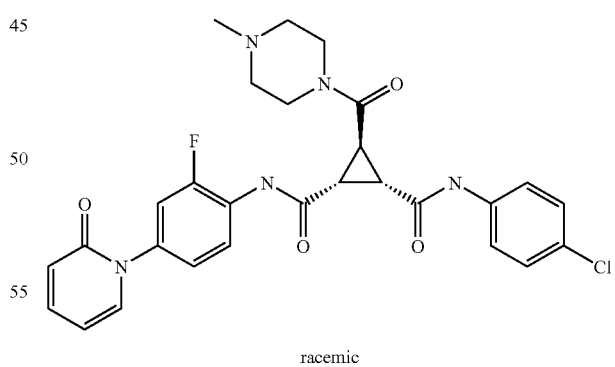

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and N-methylpiperazine was prepared (1RS,2SR,3SR)-3-(4-methyl-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Yellow oil. MS: 552 (M+H)⁺.

Example 107

(1RS,2SR,3SR)-cyclopropane-1,2,3-tricarboxylic acid 1-[(4-chloro-phenyl)-amide]2-[(2-dimethylamino-ethyl)-methyl-amide]3-{[2-fluoro-4-(2-oxo-2H-pyridin-1-yl)-phenyl]-amide}

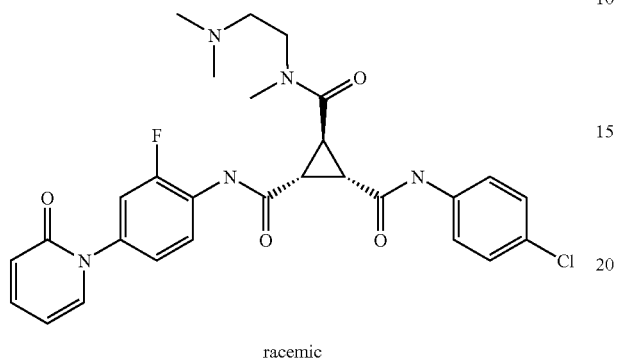

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and N,N,N'-trimethylethylenediamine was prepared (1RS,2SR,3SR)-Cyclopropane-1,2,3-tricarboxylic acid 1-[(4-chloro-phenyl)-amide]2-[(2-dimethylamino-ethyl)-methyl-amide]3-{[2-fluoro-4-(2-oxo-2H-pyridin-1-yl)-phenyl]-amide}. Light yellow oil. MS: 554 (M)+.

Example 108

(1RS,2SR,3RS)-3-(4-acetyl-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

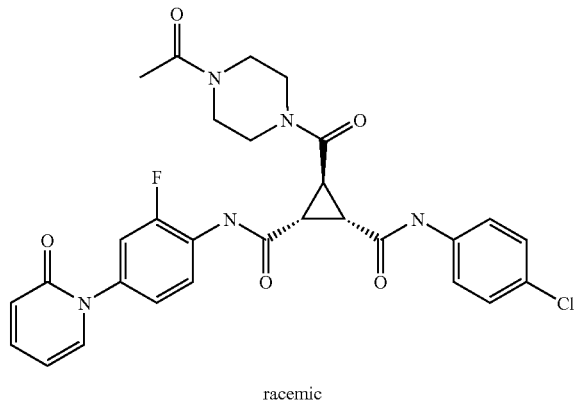

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 1-acetylpiperazine was prepared (1RS,2SR,3RS)-3-(4-actyl-piperazine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown oil. MS: 578 (M–H)⁻.

Example 109

(1RS,2SR,3SR)-3-(4-dimethylamino-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

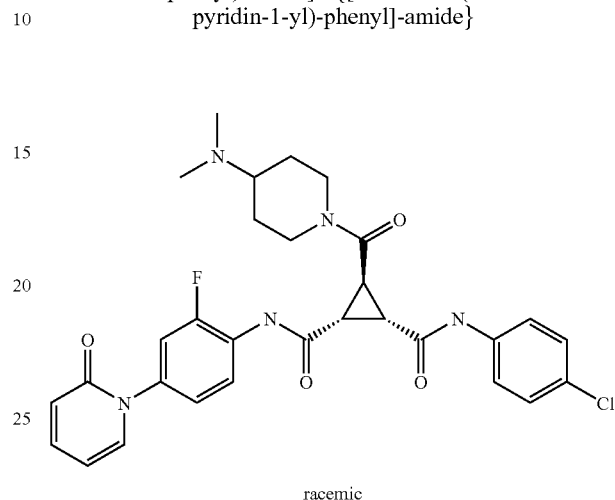

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 4-(dimethylamino)-piperidine dihydrochloride was prepared (1RS,2SR,3SR)-3-(4-dimethylamino-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown oil. MS: 578 (M–H)⁻.

Example 110

(1RS,2SR,3SR)-3-(4-carbamoyl-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

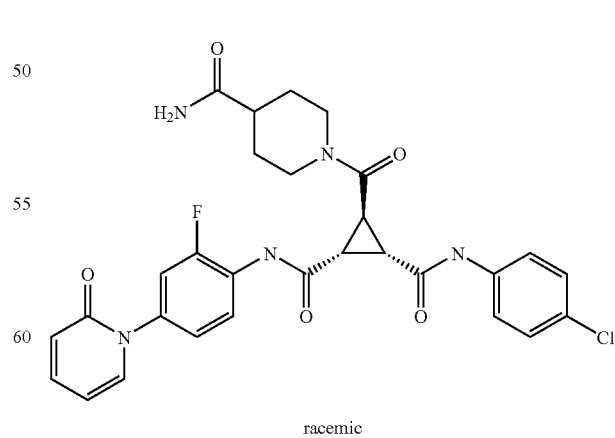

racemic

In analogy to example 72, from (1SR,2RS,3SR)-2-(4-chloro-phenylcarbamoyl)-3-[2-fluoro-4-(2-oxo-2H-pyridin- 1-yl)-phenylcarbamoyl]-cyclopropanecarboxylic acid (example 69) and isonipecotamide was prepared (1RS,2SR,3SR)-3-(4-carbamoyl-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown oil. MS: 578 (M–H)⁻.

Example 111

(1RS,2SR,3SR)-cyclopropane-1,2,3-tricarboxylic acid 1-[(4-chloro-phenyl)-amide]2-(dimethylcarbamoylmethyl-methyl-amide) 3-{[2-fluoro-4-(2-oxo-2H-pyridin-1-yl)-phenyl]-amide}

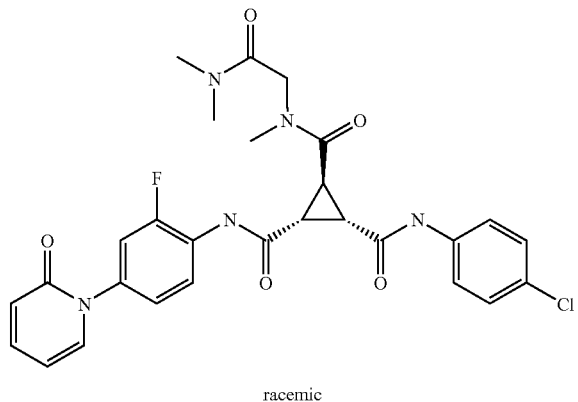

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and (methylamino)N,N-dimethylacetamide was prepared (1RS,2SR,3SR)-Cyclopropane-1,2,3-tricarboxylic acid 1-[(4-chloro-phenyl)-amide]2-(dimethylcarbamoylmethyl-methyl-amide) 3-{[2-fluoro-4-(2-oxo-2H-pyridin-1-yl)-phenyl]-amide}. Light brown oil. MS: 566 (M–H)⁻.

Example 112

(1R,2S,3S)-3-((R)-3-hydroxy-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

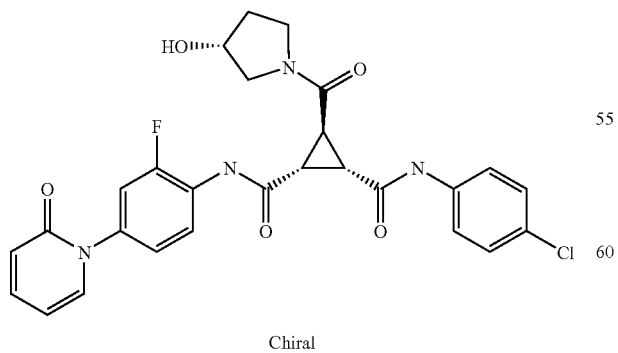

Chiral

In analogy to example 72, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid (example 71) and (R)-3-hydroxypyrrolidine was prepared (1S,2R,3S)-3-((R)-3-hydroxy-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. White crystalline. MS: 539 (M+H)⁺.

Example 113

(1R,2S,3S)-3-((S)-3-hydroxy-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

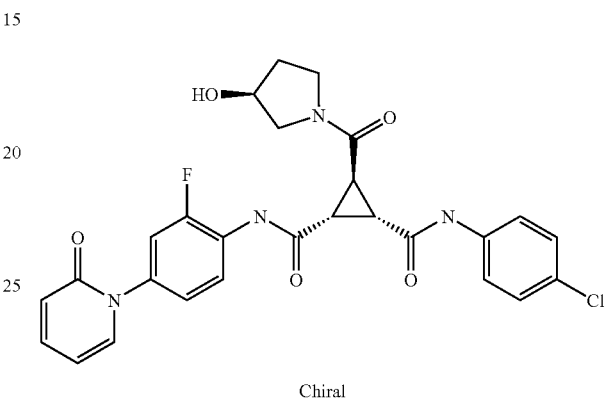

Chiral

In analogy to example 72, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid (example 71) and (S)-3-hydroxypyrrolidine was prepared (1R,2S,3S)-3-((S)-3-hydroxy-pyrrolidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. White crystalline. MS: 539 (M+H)⁺.

Example 114

(1RS,2RS,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid methyl ester

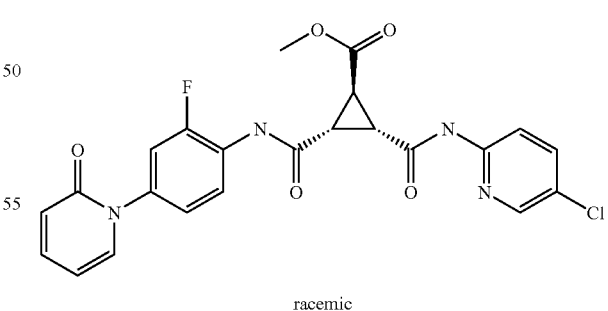

racemic

Step 1:

As solution of 10 g (100 mmol) of 1,3-dioxep-5-ene in 50 ml of dichloromethane was treated with 300 mg (0.68 mmol) of dirhodium tetraacetate and heated to reflux. A solution of 23.9 g of ethyldiazoacetate in 35 ml of dichloromethane was added dropwise over a period of 3-4 hrs and the resulting mixture was stirred at reflux during 10 hrs. After cooling to RT the mixture was filtered through silica gel and concentrated. The resulting yellow oil was dissolved in a 0.5 M HCl solution in EtOH and refluxed during 3 hrs. Evaporation of the solvent and chromatography over silica gel with heptane/AcOEt 1:1 gave 6.7 g (38%) of (1RS,2RS,3SR) 2,3-bis-hydroxymethyl-cyclopropanecarboxylic acid ethyl ester. Yellow liquid. MS: 175 (M+H)$^+$.

Step 2:

A solution of 1.15 g (7 mmol) of (1R,2S,3R) 2,3-bis-hydroxymethyl-cyclopropanecarboxylic acid ethyl ester in toluene was treated with 6.4 g of MnO$_2$ powder and intensely stirred during 10 hrs at 120°. Filtration and evaporation of the solvent gave 600 mg (53%) of (1SR, 5SR, 6SR) 2-oxo-3-oxa-bicyclo[3.1.0]hexane-6-carboxylic acid ethyl ester. Yellow oil. MS: 169: (M–H)$^-$.

Step 3:

A solution of 600 mg (2.9 mmol) of 1-(4-amino-3-fluoro-phenyl)-1H-pyridin-2-one (prepared according to C. F. Bigge et al., patent application WO 2003045912) in 10 ml of THF was cooled to –78° C. and treated dropwise with 3.2 ml of a 1M lithium bis(trimethylsilyl)amide-solution in THF and stirred for 30 min. To this solution 500 mg (3.2 mmol) of (1SR,5SR,6SR) 2-oxo-3-oxa-bicyclo[3.1.0]hexane-6-carboxylic acid ethyl ester dissolved in 5m of THF were added portionwise. The mixture was allowed to reach RT and stirred for 10 hrs. The mixture was then poured into a diluted aqueous HCl-solution (ca. 0.2 M) and extracted with AcOEt. The combined organic phases were dried with Na$_2$SO$_4$. Filtration, evaporation of the solvent gave 630 mg (57%) of (1SR,2SR, 3RS) 2-[2-fluoro-4-(2-oxo-2H-pyridin-1-yl)-phenylcarbamoyl]-3-hydroxymethyl-cyclopropanecarboxylic acid ethyl ester. Orange foam. MS: 373 (M–H)$^-$.

Step 4:

A solution of 390 mg (1.04 mmol) of (1SR,2SR,3RS)2-[2-fluoro-4-(2-oxo-2H-pyridin-1-yl)-phenylcarbamoyl]-3-hydroxymethyl-cyclopropanecarboxylic acid ethyl ester in 10 ml of acetone was treated at 0° C. with 390 ml of Jones reagent and stirred at RT for 2 hrs. The mixture was treated with 100 mg of NaHSO$_3$, stirred for 15 min and filtered. Evaporation of the solvend gave a greenish solid that was dissolved in dichloromethane, treated with 76 ul of thionylchloride and stirred at RT during 2 hrs. Evaporation of the solvent and chromatography on silica gel with AcOEt gave 136 mg (35%) of (1RS,5SR,6RS) 3-[2-fluoro-4-(2-oxo-2H-pyridin-1-yl)-phenyl]-2,4-dioxo-3-aza-bicyclo[3.1.0]hexane-6-carboxylic acid ethyl ester. Light green crystalline. MS: 369 (M–H)$^-$.

Step 5:

A solution of 27.5 mg (0.21 mmol) of 2-amino-5-chloro-pyridine in 1 ml of THF was cooled to –78° C. and treated with 0.26 ml of a 1M lithium bis(trimethylsilyl)amide-solution in THF and stirred for 30 min. To this solution 74.5 mg (0.20 mmol) of (1RS,5SR,6RS)-2-[2-fluoro-4-(2-oxo-2H-pyridin-1-yl)-phenylcarbamoyl]-3-hydroxymethyl-cyclopropanecarboxylic acid ethyl ester dissolved in 0.5 ml of THF were added portionwise. The mixture was allowed to reach RT, stirred for 10 hrs and treated with 1 ml of methanol. Evaporation of the solvent and chormatography on silica gel with AcOEt/methanol 10:1 gave 27 mg (26%) of (1RS,2RS, 3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid methyl ester. White crystalline. MS: 485 (M+H)$^+$.

Example 115

(1S,2S,3R)-cyclopropane-1,2,3-tricarboxylic acid 1-amide 2-[(4-chloro-phenyl)-amide]3-{[2-fluoro-4-(2-oxo-2H-pyridin-1-yl)-phenyl]-amide}

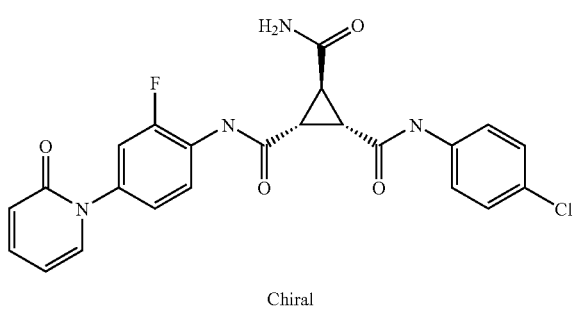

Chiral

In analogy to example 72, from (1S,2R,3S)-2-(4-chlorophenylcarbamoyl)-3-[2-fluoro-4-(2-oxo-2H-pyridin-1-yl)-phenylcarbamoyl]-cyclopropanecarboxylic acid (example 71) and ammoniumchloride was prepared (1S,2S,3R)-cyclopropane-1,2,3-tricarboxylic acid 1-amide 2-[(4-chloro-phenyl)-amide]3-{[2-fluoro-4-(2-oxo-2H-pyridin-1-yl)-phenyl]-amide}. White solid. MS. 467 (M–H)$^-$ Example 116

(1S,2R,3S)-3-(azepane-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

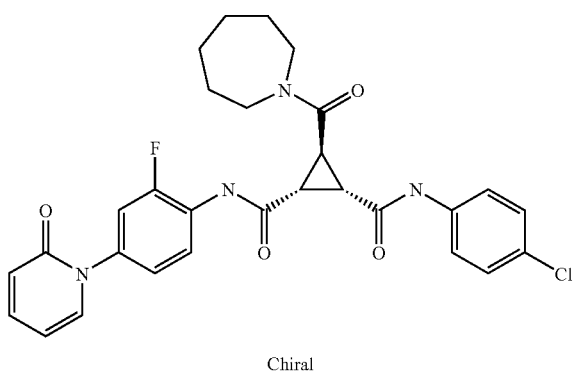

Chiral

In analogy to example 72, from (1S,2R,3S)-2-(4-chlorophenylcarbamoyl)-3-[2-fluoro-4-(2-oxo-2H-pyridin-1-yl)-phenylcarbamoyl]-cyclopropanecarboxylic acid (example 71) and hexyleneimine was prepared (1S,2R,3S)-3-(azepane-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown oil. MS: 549 (M–H)$^-$.

Example 117

(1S,2R,3S)-cyclopropane-1,2,3-tricarboxylic acid 1-(carbamoylmethyl-methyl-amide) 2-[(4-chloro-phenyl)-amide]3-{[2-fluoro-4-(2-oxo-2H-pyridin-1-yl)-phenyl]-amide}

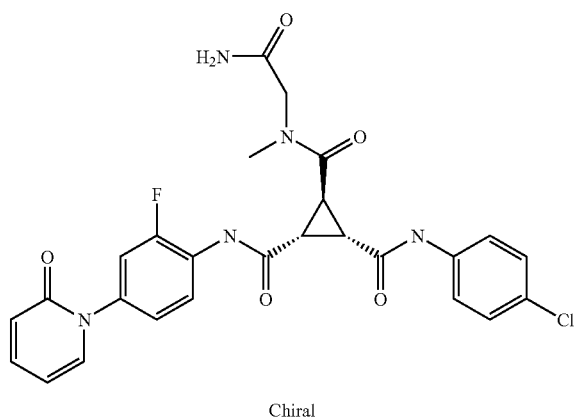

Chiral

In analogy to example 72, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid (example 71) and (methylamino)N,N-dimethylacetamide was prepared (1S,2R,3S)-cyclopropane-1,2,3-tricarboxylic acid 1-(carbamoylmethyl-methyl-amide) 2-[(4-chloro-phenyl)-amide] 3-{[2-fluoro-4-(2-oxo-2H-pyridin-1-yl)-phenyl]-amide}. Off-white solid. 538 (M–H)⁻

Example 118

(1RS,2SR,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid

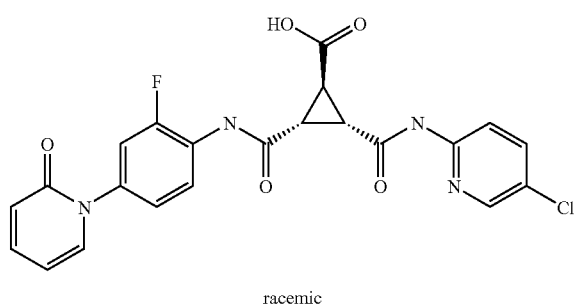

racemic

A solution of 68 mg (0.14 mmol) of (1RS,2SR,3RS)-2-(5-chloro-pyridin-2-ylcarbamoyl)-3-[2-fluoro-4-(2-oxo-2H-pyridin-1-yl)-phenylcarbamoyl]-cyclopropanecarboxylic acid methyl ester (example 114, step 5) in 1.5 ml of THF was treated with 0.2 ml of a 1M aqueous LiOH solution, stirred at RT during 2 hrs and acidified to pH ca. 2 with aqueous HCl. Extraction with AcOEt, drying of the combined organic phases over Na$_2$SO$_4$, filtration and evaporation of the solvent gave 45 mg (68%) of (1RS,2SR,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid. Light yellow crystalline. MS: 469 (M–H)⁻.

Example 119

(1RS,2SR,3RS)-3-(morpholine-4-carbonyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

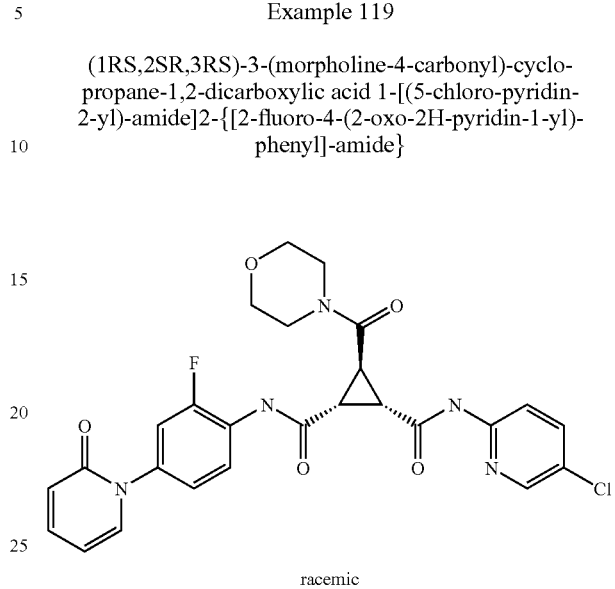

racemic

In analogy to example 72, from (1SR,2SR,3RS)-2-(5-chloro-pyridin-2-ylcarbamoyl)-3-[2-fluoro-4-(2-oxo-2H-pyridin-1-yl)-phenylcarbamoyl]-cyclopropanecarboxylic acid (example 118) and morpholine was prepared (1RS,2SR,3RS)-3-(morpholine-4-carbonyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Off-white crystalline. MS: 539 (M+H)⁺.

Example 120

(1R,2S,3S)-cyclopropane-1,2,3-tricarboxylic acid 1-[(4-chloro-phenyl)-amide]2-dimethylamide 3-{[2-fluoro-4-(2-oxo-2H-pyridin-1-yl)-phenyl]-amide}

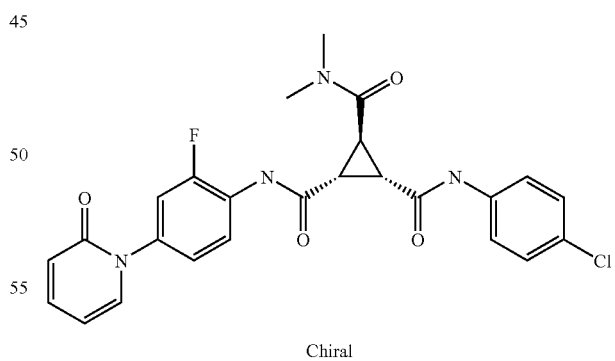

Chiral

In analogy to example 72, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid (example 71) and dimethylamine hydrochloride was prepared (1R,2S,3S)-cyclopropane-1,2,3-tricarboxylic acid 1-[(4-chloro-phenyl)-amide]2-dimethylamide 3-{[2-fluoro-4-(2-oxo-2H-pyridin-1-yl)-phenyl]-amide}. Light yellow viscous oil. MS: 498 (M+H)⁺.

Example 121

(1R,2S,3S)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-hydroxy-ethyl)-methyl-amide]

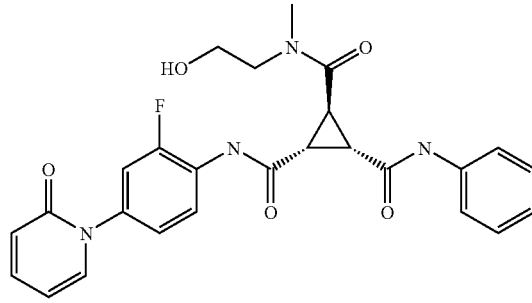

Chiral

In analogy to example 72, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid (example 71) and methylaminoethanol was prepared (1R,2S,3S)-cyclopropane-1,2,3-tricarboxylic acid 1-[(4-chloro-phenyl)-amide]3-{[2-fluoro-4-(2-oxo-2H-pyridin-1-yl)-phenyl]-amide}2-[(2-hydroxy-ethyl)-methyl-amide]. Yellow amorphous solid. MS: 528 (M+H)$^+$.

Example 122

(1RS,2RS,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid ethyl ester

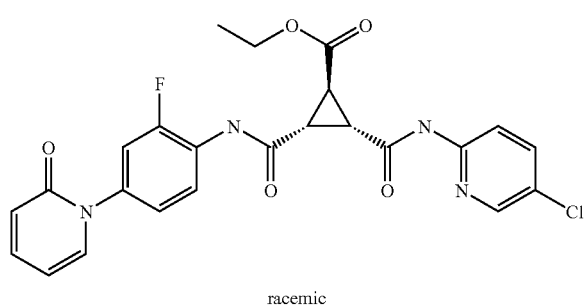

racemic

In analogy to example 114, step 5, from (1RS,5SR,6R)2-[2-fluoro-4-(2-oxo-2H-pyridin-1-yl)-phenylcarbamoyl]-3-hydroxymethyl-cyclopropanecarboxylic acid ethyl ester and 2-amino-5-chloropyridine but without treatment with methanol, was prepared (1RS,2RS,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid ethyl ester. Off-white crystalline. MS: 500 (M+H)$^+$.

Example 123

(1RS,2SR,3RS)-3-(3-hydroxy-pyrrolidine-1-carbonyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

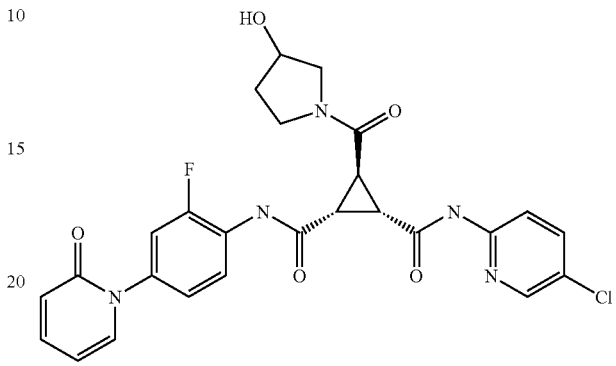

racemic, diastereoisomeric

In analogy to example 72, from (1SR,2SR,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid (example 118) and racemic 3-hydroxypyrrolidine was prepared (1RS,2SR,3RS)-3-(3-hydroxy-pyrrolidine-1-carbonyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Light brown oil. MS: 541 (M+H)$^+$.

Example 124

(1RS,2RS,3SR)-cyclopropane-1,2,3-tricarboxylic acid 1-[(5-chloro-pyridin-2-yl)-amide]2-dimethylamide 3-{[2-fluoro-4-(2-oxo-2H-pyridin-1-yl)-phenyl]-amide}

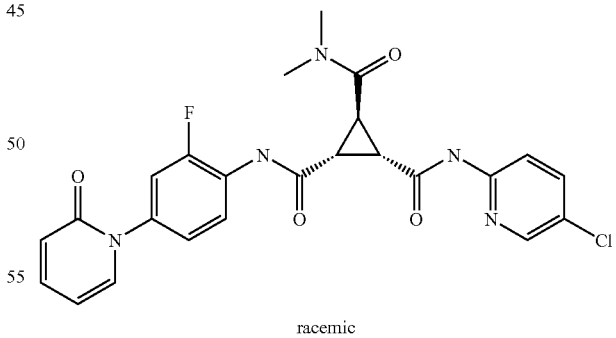

racemic

In analogy to example 72, from (1SR,2SR,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid (example 118) and dimethylamino chloride was prepared (1RS,2RS,3SR)-cyclopropane-1,2,3-tricarboxylic acid 1-[(5-chloro-pyridin-2-yl)-amide]2-dimethylamide 3-{[2-fluoro-4-(2-oxo-2H-pyridin-1-yl)-phenyl]-amide}. Light brown oil. MS: 499 (M+H)$^+$.

Example 125

(1RS,2SR,3RS)-3-(azepane-1-carbonyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

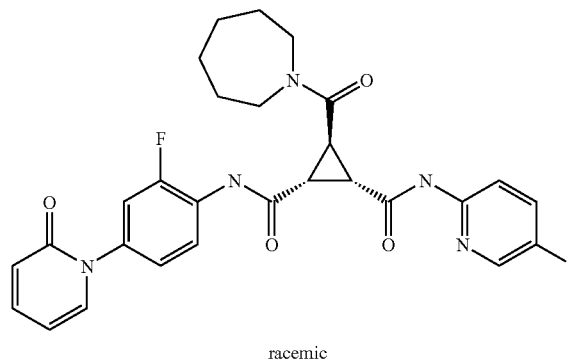

racemic

In analogy to example 72, from (1SR,2SR,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid (example 118) and hexyleneimine was prepared (1RS,2SR,3RS)-3-(azepane-1-carbonyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Light brown oil. MS: 553 (M+H)$^+$.

Example 126

(1RS,2RS,3SR)-cyclopropane-1,2,3-tricarboxylic acid 1-amide 3-[(5-chloro-pyridin-2-yl)-amide]2-{[2-fluoro-4-(2-oxo-2H-pyridin-1-yl)-phenyl]-amide}

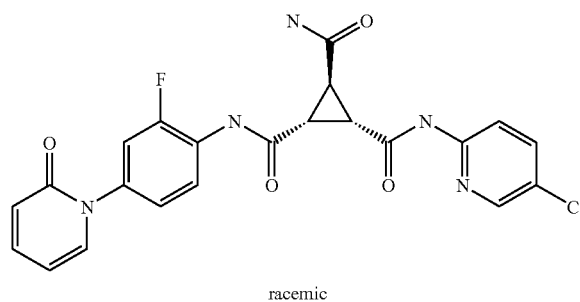

racemic

In analogy to example 72, from (1SR,2SR,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid (example 118) and ammonium chloride was prepared (1RS,2RS,3SR)-cyclopropane-1,2,3-tricarboxylic acid 1-amide 3-[(5-chloro-pyridin-2-yl)-amide]2-{[2-fluoro-4-(2-oxo-2H-pyridin-1-yl)-phenyl]-amide}. Light yellow crystalline. MS: 471 (M+H)$^+$.

Example 127

(1R,2S,3S)-3-(4-hydroxymethyl-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

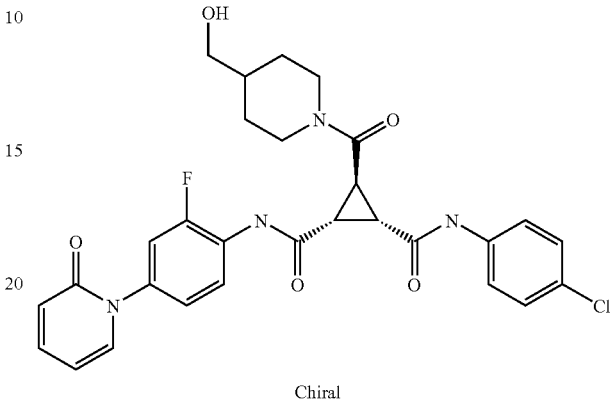

Chiral

In analogy to example 72, from (1S,2R,3S)-2-(4-chlorophenylcarbamoyl)-3-[2-fluoro-4-(2-oxo-2H-pyridin-1-yl)-phenylcarbamoyl]-cyclopropanecarboxylic acid (example 71) and 4-piperidine methanol was prepared (1R,2S,3S)-3-(4-hydroxymethyl-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown crystalline. MS: 565 (M−H)$^−$.

Example 128

(1R,2S,3S)-3-([1,4]oxazepane-4-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

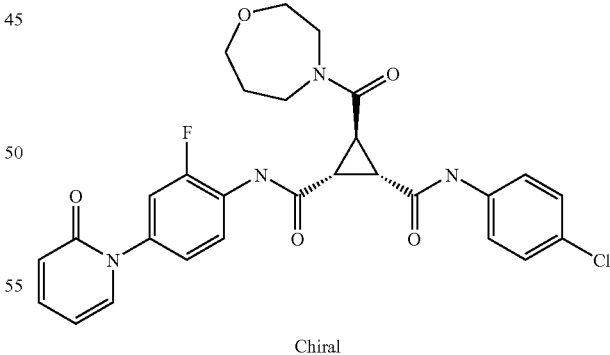

Chiral

In analogy to example 72, from (1S,2R,3S)-2-(4-chlorophenylcarbamoyl)-3-[2-fluoro-4-(2-oxo-2H-pyridin-1-yl)-phenylcarbamoyl]-cyclopropanecarboxylic acid (example 71) and homomorpholine was prepared (1R,2S,3S)-3-([1,4]oxazepane-4-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow solid. MS: 551 (M−H)$^−$.

Example 129

(1R,2S,3S)-3-(2,6-dimethyl-morpholine-4-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

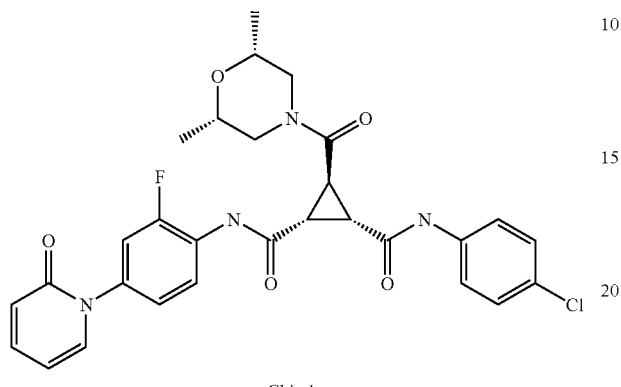

Chiral

In analogy to example 72, from (1S,2R,3S)-2-(4-chloro-phenylcarbamoyl)-3-[2-fluoro-4-(2-oxo-2H-pyridin-1-yl)-phenylcarbamoyl]-cyclopropanecarboxylic acid (example 71) and 2,6-dimethylmorpholine was prepared (1R,2S,3S)-3-(2,6-Dimethyl-morpholine-4-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light brown solid. MS: 565 (M−H)⁻.

Example 130

(1RS,2SR,3SR)-3-[3-(2,2,2-trifluoro-acetylamino)-pyrrolidine-1-carbonyl]-cyclopropane-1,2-dicarboxylic acid 1-[(4-chloro-phenyl)-amide]2-{[2-fluoro-4-(2-oxo-2H-pyridin-1-yl)-phenyl]-amide}

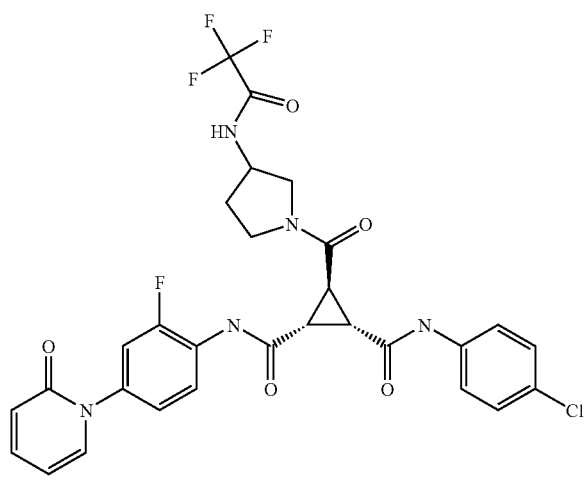

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 69) and 3-(trifluoracetamido)pyrrolidine was prepared (1RS,2SR,3SR)-3-[3-(2,2,2-trifluoro-acetylamino)-pyrrolidine-1-carbonyl]-cyclopropane-1,2-dicarboxylic acid 1-[(4-chloro-phenyl)-amide]2-{[2-fluoro-4-(2-oxo-2H-pyridin-1-yl)-phenyl]-amide}. Light brown oil. MS: 632 (M−H)⁻.

Example 131

(1RS,2SR,3SR)-3-(3-hydroxymethyl-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}

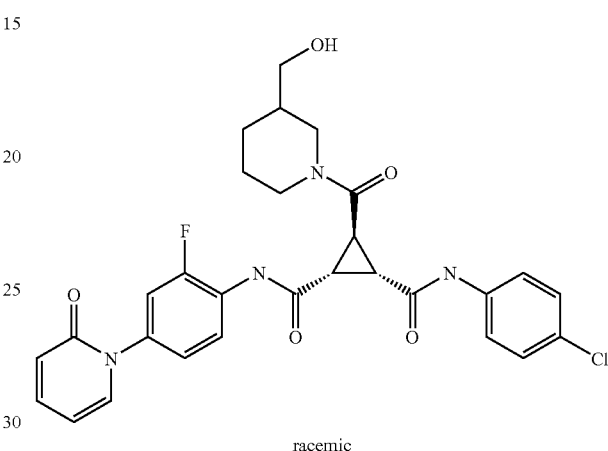

racemic

In analogy to example 72, from (1SR,2RS,3SR)-2-(4-chloro-phenylcarbamoyl)-3-[2-fluoro-4-(2-oxo-2H-pyridin-1-yl)-phenylcarbamoyl]-cyclopropanecarboxylic acid (example 71) and 3-piperidinemethanol was prepared (1RS,2SR,3SR)-3-(3-hydroxymethyl-piperidine-1-carbonyl)-cyclopropane-1,2-dicarboxylic acid 1-[(4-chloro-phenyl)-amide]2-{[2-fluoro-4-(2-oxo-2H-pyridin-1-yl)-phenyl]-amide}. Yellow oil. MS: 565 (M−H)⁻.

Example 132

(1S,2R,3S)-3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}

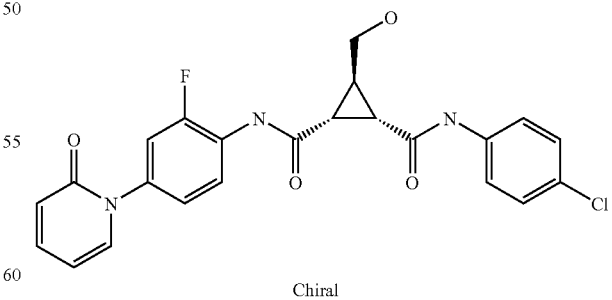

Chiral

Step 1:

In analogy to example 100, step 3, from 4-chloro-aniline and (1S,2R,3R) 2-[2-fluoro-4-(2-oxo-2H-pyridin-1-yl)-phenylcarbamoyl]-3-(4-methoxy-phenoxymethyl)-cyclopropanecarboxylicacid methyl ester (example 157, step 7) was prepared (1S,2R,3S) 3-(4-methoxy-benzyloxymethyl)-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow solid. MS: 577 (M+H)+.

Step 2:

A solution of 50 mg (0.086 mmol) of (1S,2R,3S)-3-(4-methoxy-benzyloxymethyl)-cyclopropane-1,2-dicarboxylic acid 1-[(4-chloro-phenyl)-amide]2-{[2-fluoro-4-(2-oxo-2H-pyridin-1-yl)-phenyl]-amide} in dichloromethane was treated with 20 mg (0.09 mmol) of 2,3-dichloro-5,6-dicyano-1,4-benzoquinone and stirred at RT for 5 hrs. The mixture was poured into a diluted aqueous solution of HCl and extracted with AcOEt. Drying of the combined organic phases over Na₂SO₄, filtration, evaporation of the solvent, and chromatography on silica gel with AcOEt gave 35 mg (89%) of (1S,2R,3S) 3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow solid. MS: 458 (M+H)+.

Example 133

(1S,2R,3S)-3-(3,3-difluoro-pyrrolidin-1-ylmethyl)-cyclopropane-1,2-dicarboxylic acid 1-[(4-chloro-phenyl)-amide]2-{[2-fluoro-4-(2-oxo-2H-pyridin-1-yl)-phenyl]-amide}

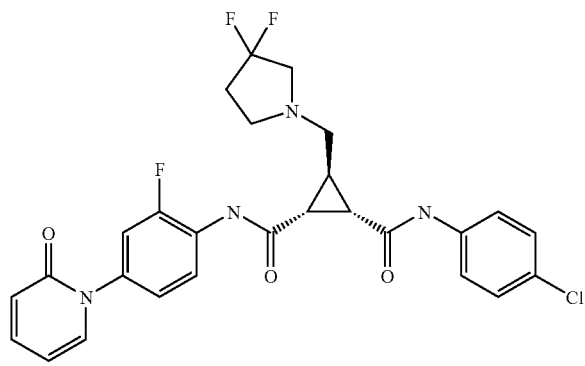

Chiral

Step 1:

A solution of 100 mg (0.22 mmol) (1S,2R,3S) 3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide} (example 132, step 9) in 1 ml of dichloromethane was treated with 50 ul of N,N-diisopropyl ethyl amine and 30 ul of methane sulfonylchlorid. The solution was stirred for 2 hrs and poured into a diluted aqueous solution of NaOH. Extraction with AcOEt, drying of the combined organic phases over Na₂SO₄, filtration and evaporation gave 110 mg (94%) (1S,2S,3R) methanesulfonic acid 2-(4-chloro-phenylcarbamoyl)-3-[2-fluoro-4-(2-oxo-2H-pyridin-1-yl)-phenylcarbamoyl]-cyclopropylmethyl ester. Yellow oil. MS: 535 (M+H)+.

Step 2:

A solution of 25 mg (0.047 mmol) of (1S,2S,3R) methanesulfonic acid 2-(4-chloro-phenylcarbamoyl)-3-[2-fluoro-4-(2-oxo-2H-pyridin-1-yl)-phenylcarbamoyl]-cyclopropylmethyl ester in DMF was treated with 60 ul of N,N-diisopropyl ethyl amine and 54 mg of 3,3-difluoropyrrolidine. The mixture was stirred at 70° during 10 hrs and poured into a diluted aqueous solution of NaOH. Extraction with AcOEt, drying of the combined organic phases over Na₂SO₄, filtration, evaporation, and chromatography on silica gel with AcOEt containing 1% of triethylamine gave 18 mg (71%) of (1S,2R,3S)-3-(3,3-difluoro-pyrrolidin-1-ylmethyl)-cyclopropane-1,2-dicarboxylic acid 1-[(4-chloro-phenyl)-amide]2-{[2-fluoro-4-(2-oxo-2H-pyridin-1-yl)-phenyl]-amide}. Yellow oil. MS: 543 (M−H)−.

Example 134

(1S,2R,3S)-3-morpholin-4-ylmethyl-cyclopropane-1, 2-dicarboxylic acid 1-[(4-chloro-phenyl)-amide]2-{ [2-fluoro-4-(2-oxo-2H-pyridin-1-yl)-phenyl]-amide}

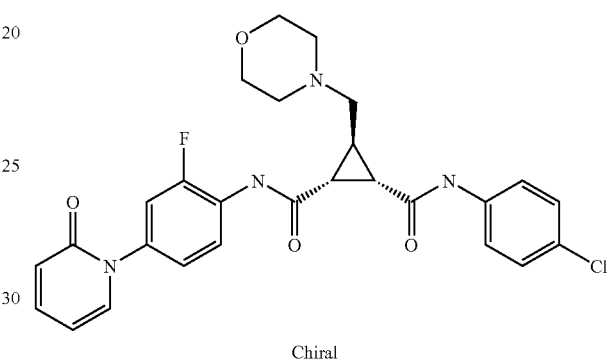

Chiral

In analogy to example 133, step 2, from (1S,2S,3R) methanesulfonic acid 2-(4-chloro-phenylcarbamoyl)-3-[2-fluoro-4-(2-oxo-2H-pyridin-1-yl)-phenylcarbamoyl]-cyclopropylmethyl ester (example 133, step 1) and morpholine was prepared (1S,2R,3S)-3-morpholin-4-ylmethyl-cyclopropane-1,2-dicarboxylic acid 1-[(4-chloro-phenyl)-amide]2-{ [2-fluoro-4-(2-oxo-2H-pyridin-1-yl)-phenyl]-amide}. Light yellow oil. MS: 523 (M+H)+.

Example 135

(1S,2R,3S)-3-Pyrrolidin-1-ylmethyl-cyclopropane-1, 2-dicarboxylic acid 1-[(4-chloro-phenyl)-amide]2-{ [2-fluoro-4-(2-oxo-2H-pyridin-1-yl)-phenyl]-amide}

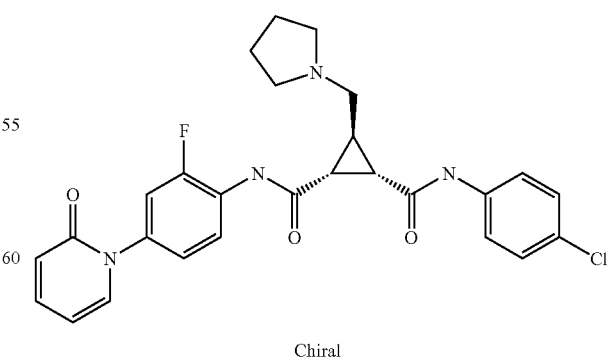

Chiral

In analogy to example 133, step 2, from (1S,2S,3R) methanesulfonic acid 2-(4-chloro-phenylcarbamoyl)-3-[2-fluoro- 4-(2-oxo-2H-pyridin-1-yl)-phenylcarbamoyl]-cyclopropyl-methyl ester (example 133, step 1) and pyrrolidine was prepared (1S,2R,3S)-3-pyrrolidin-1-ylmethyl-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow oil. 507 (M−H)⁻.

Example 136

(1S,2R,3S)-3-Fluoromethyl-cyclopropane-1,2-dicarboxylic acid 1-[(4-chloro-phenyl)-amide]2-{[2-fluoro-4-(2-oxo-2H-pyridin-1-yl)-phenyl]-amide}

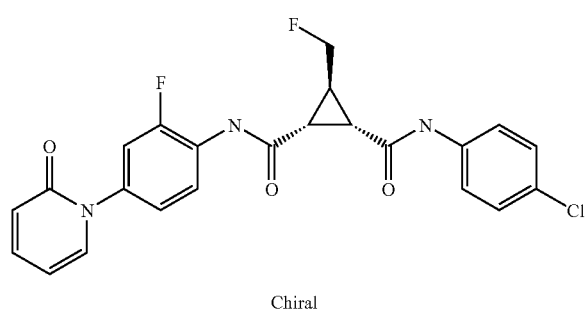

Chiral

In analogy to example 133, step 2, from (1S,2S,3R) methanesulfonic acid 2-(4-chloro-phenylcarbamoyl)-3-[2-fluoro-4-(2-oxo-2H-pyridin-1-yl)-phenylcarbamoyl]-cyclopropyl-methyl ester (example 133, step 1) and tetrabutylammonium fluoride was prepared (1S,2R,3S)-3-fluoromethyl-cyclopropane-1,2-dicarboxylic acid 1-[(4-chloro-phenyl)-amide]2-{[2-fluoro-4-(2-oxo-2H-pyridin-1-yl)-phenyl]-amide}. Colorless viscous oil. MS: 456 (M−H)⁻.

Example 137

(1S,2R,3S)-3-Imidazol-1-ylmethyl-cyclopropane-1,2-dicarboxylic acid 1-[(4-chloro-phenyl)-amide]2-{[2-fluoro-4-(2-oxo-2H-pyridin-1-yl)-phenyl]-amide}

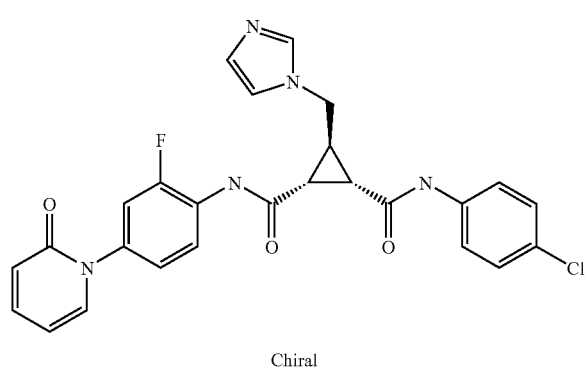

Chiral

In analogy to example 133, step 2, from (1S,2S,3R) methanesulfonic acid 2-(4-chloro-phenylcarbamoyl)-3-[2-fluoro-4-(2-oxo-2H-pyridin-1-yl)-phenylcarbamoyl]-cyclopropyl-methyl ester (example 133, step 1) and imidazole was prepared (1S,2R,3S)-3-imidazol-1-ylmethyl-cyclopropane-1,2-dicarboxylic acid 1-[(4-chloro-phenyl)-amide]2-{[2-fluoro-4-(2-oxo-2H-pyridin-1-yl)-phenyl]-amide}. White solid. MS: 454 (M−H)⁻.

Example 138

(1S,2R,3S)-3-cyanomethyl-cyclopropane-1,2-dicarboxylic acid 1-[(4-chloro-phenyl)-amide]2-{[2-fluoro-4-(2-oxo-2H-pyridin-1-yl)-phenyl]-amide}

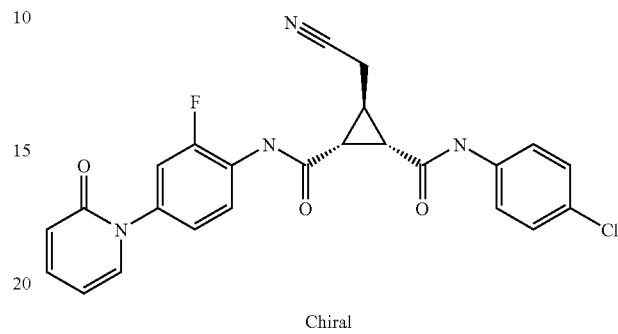

Chiral

In analogy to example 133, step 2, from (1S,2S,3R) methanesulfonic acid 2-(4-chloro-phenylcarbamoyl)-3-[2-fluoro-4-(2-oxo-2H-pyridin-1-yl)-phenylcarbamoyl]-cyclopropyl-methyl ester (example 133, step 1) and sodium cyanide was prepared (1S,2R,3S)-3-cyanomethyl-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow oil. MS: 563 (M−H)⁻.

Example 139

(1S,2R,3S)-3-methoxymethyl-cyclopropane-1,2-dicarboxylic acid 1-[(4-chloro-phenyl)-amide]2-{[2-fluoro-4-(2-oxo-2H-pyridin-1-yl)-phenyl]-amide}

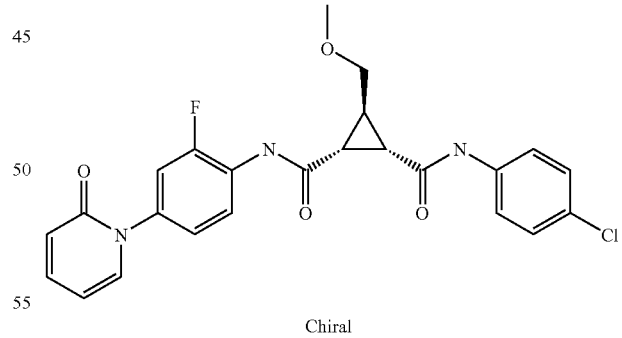

Chiral

In analogy to example 133, step 2, from (1S,2S,3R) methanesulfonic acid 2-(4-chloro-phenylcarbamoyl)-3-[2-fluoro-4-(2-oxo-2H-pyridin-1-yl)-phenylcarbamoyl]-cyclopropyl-methyl ester (example 133, step 1) and sodium methoxide in methanol was prepared (1S,2R,3S)-3-Methoxymethyl-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow oil. 470 (M+H)⁺.

Example 140

(1SR,2RS,3RS)-3-hydroxymethyl-cyclopropane-1,2-dicarboxylic acid 1-[(5-chloro-pyridin-2-yl)-amide] 2-{[2-fluoro-4-(2-oxo-2H-pyridin-1-yl)-phenyl]-amide}

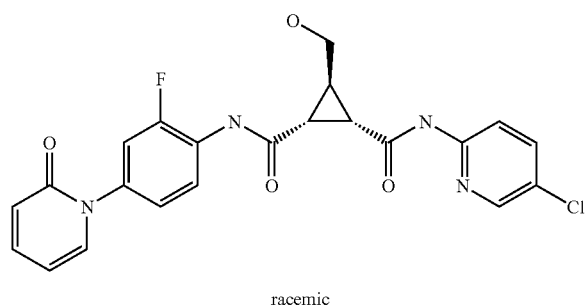

racemic

A solution of 395 mg (0.79 mmol) (1RS,2RS,3SR)-2-(5-chloro-pyridin-2-ylcarbamoyl)-3-[2-fluoro-4-(2-oxo-2H-pyridin-1-yl)-phenylcarbamoyl]-cyclopropanecarboxylic acid ethyl ester (example 122) in 10 ml of ethanol was treated with 63 mg (1.7 mmol) of sodium borohydride. After stirring during 2 hrs additional 30 mg (0.8 mmol) of sodium borohydride were added and the mixture stirred at 60° for 32 hrs. The mixture was poured into a saturated aqueous solution of NaCl and extracted with AcOEt. Drying of the combined organic phases over $Na_2SO_4$, filtration, evaporation of the solvent and chromatography on silica gel with AcOEt/methanol 10:1 gave 27 mg (8%) of (1SR,2RS,3RS)-3-hydroxymethyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Colorless oil. MS: 455 (M–H)⁻.

Example 141

(1SR,2RS)-1-cyano-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

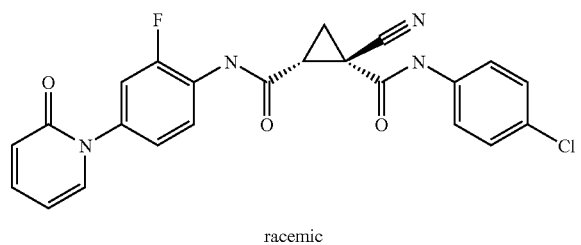

racemic

Step 1:

A solution of 800 mg (6.0 mmol) of (1SR, 2RS) 2-oxo-3-oxa-bicyclo[3.1.0]hexane-1-carbonitrile (obtained from cyano acetic acid allylester by application of procedures leading to similar 2-oxo-3-oxa-bicyclo[3.1.0]hexanes described by Toeke et al. Tetrahedron 1993, 49, p5133-5146 and by Burgess et al. J. Org. Chem. 1992, 57, p5931-5936) in 10 ml of acetone was treated with 5 ml of Jones reagent and stirred at RT during 5 hrs. The mixture was treated with ca 100 mg of $NaHSO_3$, stirred 1 hr and the precipitate removed through filtration. Drying over $Na_2SO_4$, filtration, and evaporation gave a greenish resin that was dissolved in 5 ml acetonitrile, treated with excess of thionylchloride and stirred for 2 hrs. Evaporation of the solvent gave 750 mg (91%) of (1SR,2RS) 2,4-dioxo-3-oxa-bicyclo[3.1.0]hexane-1-carbonitrile. Brown solid.

Step 2:

100 mg (0.73 mmol) of (1SR,2RS) 2,4-dioxo-3-oxa-bicyclo[3.1.0]hexane-1-carbonitrile were dissolved in a solution of 223 mg (1.1 mmol) of 1-(4-amino-3-fluoro-phenyl)-1H-pyridin-2-one (prepared according to C.F. Bigge et al., patent application WO 2003045912) in 2 ml of pyridine at 0°. The mixture was stirred at RT during 2 hrs and the solvent evaporated. Addition of diluted aqueous HCl, extraction with AcOEt, drying of the combined organic phases over $Na_2SO_4$, filtration and evaporation of the solvent gave 130 mg (52%) of (1SR,2RS) 1-cyano-2-[2-fluoro-4-(2-oxo-2H-pyridin-1-yl)-phenylcarbamoyl]-cyclopropanecarboxylic acid. Light brown semisolid. MS: 340 (M–H)⁻.

Step 3:

In analogy example 100, step 2, from (1SR,2RS) 1-cyano-2-[2-fluoro-4-(2-oxo-2H-pyridin-1-yl)-phenylcarbamoyl]-cyclopropanecarboxylic acid was prepared (1SR,2RS) 1-cyano-2-[2-fluoro-4-(2-oxo-2H-pyridin-1-yl)-phenylcarbamoyl]-cyclopropanecarboxylic acid methyl ester. Brown semisold. MS: 356 (M+H)⁺.

Step 4:

In analogy to example 100, step 3, from (1SR,2RS) 1-cyano-2-[2-fluoro-4-(2-oxo-2H-pyridin-1-yl)-phenylcarbamoyl]-cyclopropanecarboxylic acid methyl ester and 2-amino-5-chloropyridine was prepared (1SR,2RS)-1-cyano-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Off-white solid. MS: 450 (M–H)⁻.

Example 142

(1SR,2RS,3SR)-2-(4-chloro-phenylcarbamoyl)-3-[2-fluoro-4-(4-hydroxy-2-oxo-2H-pyridin-1-yl)-phenylcarbamoyl]-cyclopropanecarboxylic acid ethyl ester

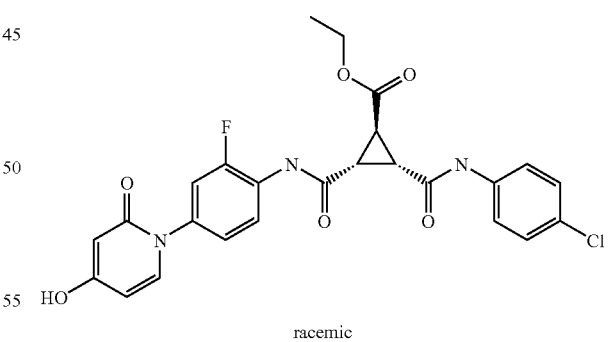

racemic

Step 1:

A solution of 580 mg (1.87 mmol) 1-(4-amino-3-fluorophenyl)-4-benzyloxy-1H-pyridin-2-one (example 144, step 1) in 20 ml of MeOH was treated with 140 mg of Pd/C (10%) and hydrogenated at atmospheric pressure under vigorous stirring for 3 hrs. Filtration and evaporation of the solvent gave 398 mg (97%) of 1-(4-Amino-3-fluoro-phenyl)-4-hydroxy-1H-pyridin-2-one. Light brown solid. MS: 221 (M+H)⁺.

Step 2:

In analogy to example 68, step 4, from 1-(4-amino-3-fluoro-phenyl)-4-hydroxy-1H-pyridin-2-one, 2.2 equiv. of lithium bis(trimethylsilyl)amide, and (1RS,5SR,6RS)-3-(4-chloro-phenyl)-2,4-dioxo-3-aza-bicyclo[3.1.0]hexane-6-carboxylic acid ethyl ester was prepared (1SR,2RS,3SR)-2-(4-chloro-phenylcarbamoyl)-3-[2-fluoro-4-(4-hydroxy-2-oxo-2H-pyridin-1-yl)-phenylcarbamoyl]-cyclopropanecarboxylic acid ethyl ester. Brown solid. 512 (M−H)⁻.

Example 143

(1SR,2RS,3SR)-2-(4-chloro-phenylcarbamoyl)-3-[2-fluoro-4-(4-methoxy-2-oxo-2H-pyridin-1-yl)-phenylcarbamoyl]-cyclopropanecarboxylic acid ethyl ester

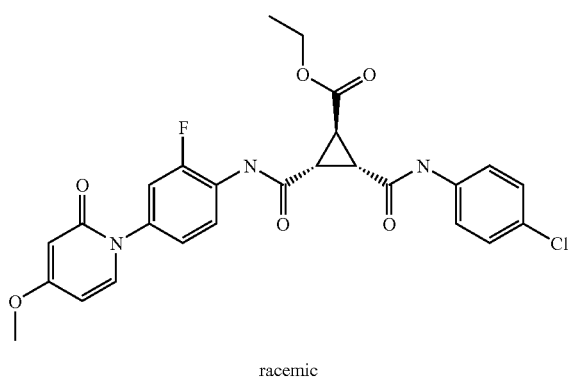

racemic

A solution of 35 mg (0.07 mmol) of (1SR,2RS,3SR)-2-(4-chloro-phenylcarbamoyl)-3-[2-fluoro-4-(4-hydroxy-2-oxo-2H-pyridin-1-yl)-phenylcarbamoyl]-cyclopropanecarboxylic acid ethyl ester (example 142, step 2) in 5 ml of acetone was treated with 94 mg (0.6 mmol) of potassium carbonate and 8 ul (0.08 mmol) of dimethylsulfate. The mixture was stirred 2 hrs at RT and filtered. Evaporation of the solvent and chromatography on silica gel with AcOEt/methanol 95:5 gave 5 mg (13%) of (1SR,2RS,3SR)-2-(4-chloro-phenylcarbamoyl)-3-[2-fluoro-4-(4-methoxy-2-oxo-2H-pyridin-1-yl)-phenylcarbamoyl]-cyclopropanecarboxylic acid ethyl ester. Off-white solid. 526 (M−H)⁻.

Example 144

(1SR,2SR,3RS)-2-[4-(4-benzyloxy-2-oxo-2H-pyridin-1-yl)-2-fluoro-phenylcarbamoyl]-3-(4-chloro-phenylcarbamoyl)-cyclopropanecarboxylic acid ethyl ester

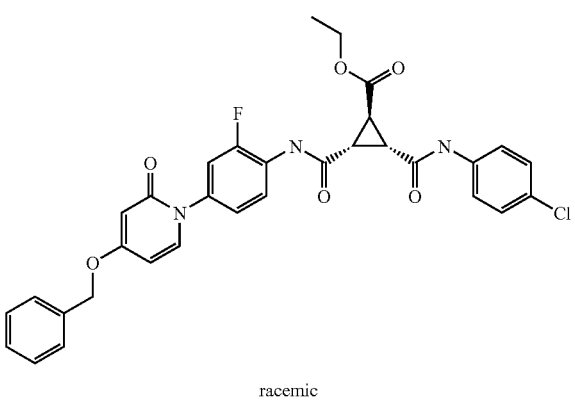

racemic

Step 1:

1-(4-Amino-3-fluoro-phenyl)-4-benzyloxy-1H-pyridin-2-one was prepared from 4-benzyloxy-1H-pyridin-2-one and 4-bromo-2-fluoroaniline in analogy to the procedure described for the preparation of 1-(4-amino-3-fluoro-phenyl)-1H-pyridin-2-one described in C. F. Bigge et al., patent application WO 2003045912. MS: 311 (M+H)⁺.

Step 2:

In analogy to example 68, step 4, from 1-(4-amino-3-fluoro-phenyl)-1H-pyridin-2-one and (1RS,5SR,6RS)-3-(4-chloro-phenyl)-2,4-dioxo-3-aza-bicyclo[3.1.0]hexane-6-carboxylic acid ethyl ester was prepared (1SR,2RS,3SR)-2-[4-(4-benzyloxy-2-oxo-2H-pyridin-1-yl)-2-fluoro-phenylcarbamoyl]-3-(4-chloro-phenylcarbamoyl)-cyclopropanecarboxylic acid ethyl ester. Brown solid. 602 (M−H)⁻.

Example 145

(1SR,2SR,3RS)-2-[4-(4-tert-butoxycarbonyl-methoxy-2-oxo-2H-pyridin-1-yl)-2-fluoro-phenylcarbamoyl]-3-(4-chloro-phenylcarbamoyl)-cyclopropanecarboxylic acid ethyl ester

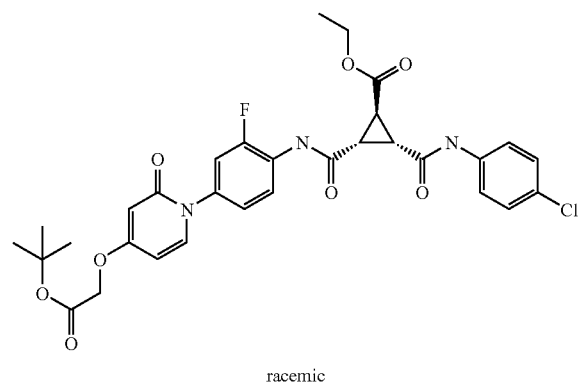

racemic

In analogy to example 143, from (1SR,2RS,3SR)-2-(4-chloro-phenylcarbamoyl)-3-[2-fluoro-4-(4-hydroxy-2-oxo-2H-pyridin-1-yl)-phenylcarbamoyl]-cyclopropanecarboxylic acid ethyl ester (example 142, step 2) and tert-butylbromoacetate was prepared (1SR,2RS,3SR)-2-[4-(4-tert-butoxycarbonylmethoxy-2-oxo-2H-pyridin-1-yl)-2-fluoro-phenylcarbamoyl]-3-(4-chloro-phenylcarbamoyl)-cyclopropanecarboxylic acid ethyl ester. Colorless solid. MS: 626 (M−H)⁻.

Example 146

(1SR,2SR,3RS)-2-[4-(4-carbamoylmethoxy-2-oxo-2H-pyridin-1-yl)-2-fluoro-phenylcarbamoyl]-3-(4-chloro-phenylcarbamoyl)-cyclopropanecarboxylic acid ethyl ester

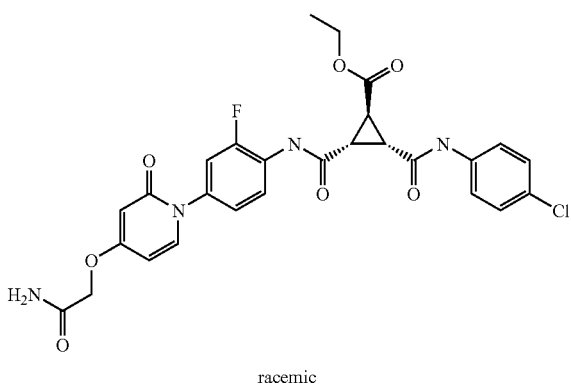

racemic

In analogy to example 143, from (1SR,2RS,3SR)-2-(4-chloro-phenylcarbamoyl)-3-[2-fluoro-4-(4-hydroxy-2-oxo-2H-pyridin-1-yl)-phenylcarbamoyl]-cyclopropanecarboxylic acid and 2-bromoacetamide was prepared (1SR,2RS,3SR)-2-[4-(4-carbamoylmethoxy-2-oxo-2H-pyridin-1-yl)-2-fluoro-phenylcarbamoyl]-3-(4-chloro-phenylcarbamoyl) cyclopropanecarboxylic acid ethyl ester. Off-white solid. MS: 569 (M–H)⁻.

Example 147

(1RS,2RS)-1-(4-chloro-phenylcarbamoyl)-2-[2-fluoro-4-(2-oxo-2H-pyridin-1-yl)-phenylcarbamoyl]-cyclopropanecarboxylic acid allyl ester

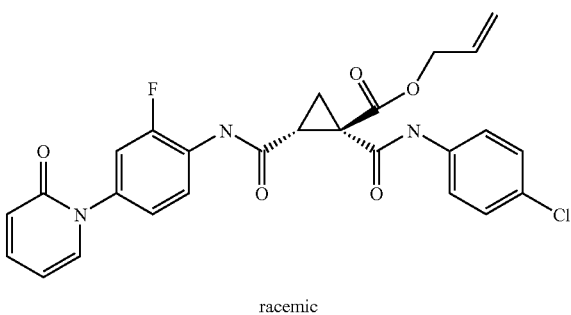

racemic

Step 1:

In analogy to example 141, step 1, from (1RS,2RS) 2-oxo-3-oxa-bicyclo[3.1.0]hexane-1-carboxylic acid allyl ester (obtained from malonic diallylester by application of procedures leading to similar 2-oxo-3-oxa-bicyclo[3.1.0]hexanes described by Toeke et al. Tetrahedron 1993, 49, p5133-5146 and by Burgess et al. J. Org. Chem. 1992, 57, p5931-5936) Jones reagent and thionylchloride was prepared (1RS,2RS) 2,4-dioxo-3-oxa-bicyclo[3.1.0]hexane-1-carboxylic acid allyl ester. Light red oil.

Step 2:

In analogy to example 141, step 2, from (1RS,2RS) 2,4-dioxo-3-oxa-bicyclo[3.1.0]hexane-1-carboxylic acid allyl ester and 4-chloroaniline was prepared (1RS,2RS) 2-(4-chloro-phenylcarbamoyl)-cyclopropane-1,1-dicarboxylic acid allyl ester. Yellow oil. 322 (M–H)⁻.

Step 3:

A solution of 400 mg (1.23 mmol) of (1RS,2RS) 2-(4-chloro-phenylcarbamoyl)-cyclopropane-1,1-dicarboxylic acid allyl ester in dichloromethane was treated with 1.79 ml (24.6 mmol) of thionylchloride and stirred at RT during 1 hr. Evaporation of the solvent gave 320 mg of (1RS,2RS) 3-(4-chloro-phenyl)-2,4-dioxo-3-aza-bicyclo[3.1.0]hexane-1-carboxylic acid allyl ester. Light grey crystalline. MS: 307 (M+H)⁺.

Step 4:

In analogy to example 68, step 4, from 1-(4-amino-3-fluoro-phenyl)-1H-pyridin-2-one (prepared according to C. F. Bigge et al., patent application WO 2003045912) and (1RS,2RS) 3-(4-chloro-phenyl)-2,4-dioxo-3-aza-bicyclo[3.1.0]hexane-1-carboxylic acid allyl ester was prepared (1RS,2RS)-1-(4-chloro-phenylcarbamoyl)-2-[2-fluoro-4-(2-oxo-2H-pyridin-1-yl)-phenylcarbamoyl]-cyclopropanecarboxylic acid allyl ester. Light yellow oil. MS: 508 (M–H)⁻.

Example 148

(1SR,2RS)-1-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}

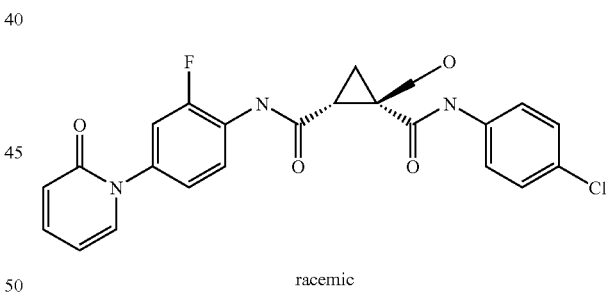

racemic

A solution of 50 mg (0.12 mmol) of (1RS,2RS)-1-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide} (example 147, step 4) in 1 ml of ethanol was treated with 14.2 mg (0.37 mmol) of sodium borohydride and stirred at RT during 16 hrs. The mixture was poured into a 2M aqueous solution of HCl and extracted with AcOEt. Drying of the combined organic phases, filtration and evaporation of the solvent gave 39 mg (71%) of (1SR,2RS)-1-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}. Light yellow oil. MS: 454 (M–H)⁻.

Example 149

(1SR,2RS,3SR)-2-(4-chloro-phenylcarbamoyl)-3-[4-(4-dimethylcarbamoylmethoxy-2-oxo-2H-pyridin-1-yl)-2-fluoro-phenylcarbamoyl]-cyclopropanecarboxylic acid ethyl ester

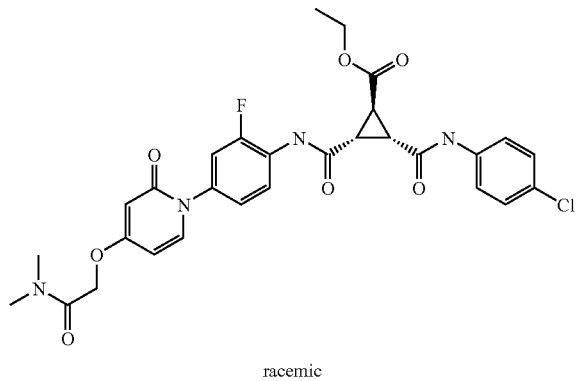

racemic

A mixture of 23 mg (0.04 mmol) of (1SR,2RS,3SR) 2-[4-(4-carboxymethoxy-2-oxo-2H-pyridin-1-yl)-2-fluoro-phenylcarbamoyl]-3-(4-chloro-phenylcarbamoyl) cyclopropanecarboxylic acid ethyl ester (example 155), 5 mg (0.06 mmol) of dimethylamine hydrochloride, 1 mg of 1-hydroxybenzotriazole, and 25 ul (0.23 mmol) of N-methylmorpholine in 2.5 ml of DMF was treated with 11 mg (0.06 mmol) of 1-(3-dimethylaminopropyl)-3-ethylcarbodiimide hydrochloride and stirred at RT during 10 hrs. The mixture was poured into a 2M aqueous solution of HCl and extracted with AcOEt. Drying of the combined organic phases over $Na_2SO_4$, filtration, evaporation of the solvent and chromatography on silica gel with AcOEt/MeOH 10:1 gave 22 mg (95%) of (1SR,2RS,3SR)-2-(4-chloro-phenylcarbamoyl)-3-[4-(4-dimethylcarbamoylmethoxy-2-oxo-2H-pyridin-1-yl)-2-fluoro-phenylcarbamoyl]-cyclopropanecarboxylic acid ethyl ester. Light brown solid. MS: 600 (M+H)$^+$.

Example 150

(1S,2R,3S)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

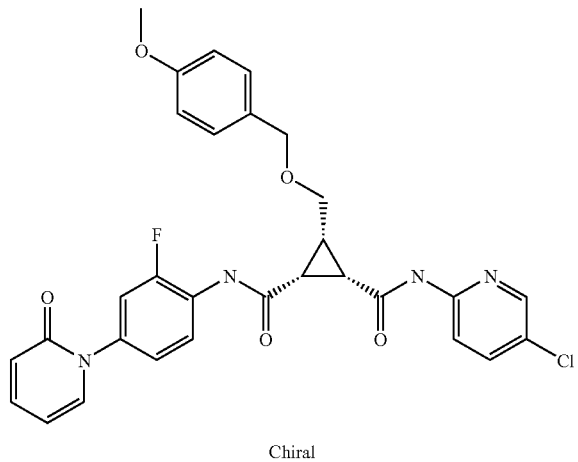

Chiral

In analogy to examples 157, step 1-157, step 8 from cis 2-butene-1,4-diol was prepared (1S,2R,3S)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Light yellow oil. MS: 575 (M−H)$^-$.

Example 151

(1SR,2RS,3SR)-3-(4-methoxy-benzyloxymethyl)-cyclopropane-1,2-dicarboxylic acid 1-[(5-chloro-pyridin-2-yl)-amide]2-{[2-fluoro-4-(6-oxo-cyclohexa-2,4-dienyl)-phenyl]-amide}

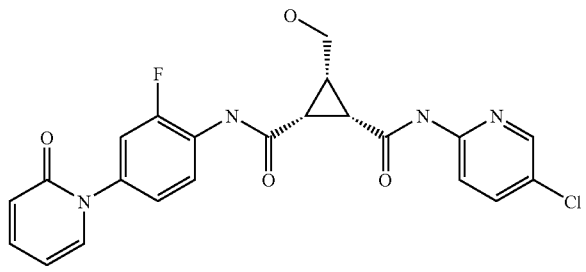

racemic

Step 1:
In analogy to examples 157, step 1-157, step 3 from cis 2-butene-1,4-diol was prepared diazo acetic acid cis 4-(4-methoxy-benzyloxy)-but-2-enyl ester. Yellow oil.

Step 2:
In analogy ot example 157, step 4, from diazo acetic acid cis 4-(4-methoxy-benzyloxy)-but-2-enyl ester and dirhodiumtetraacetate was prepared (1RS,5SR,6RS) 6-(4-methoxy-benzyloxymethyl)-3-oxa-bicyclo[3.1.0]hexan-2-one. Yellow semisolid. 453 (M+H)$^+$.

Step 3:
In analogy to examples 157, step 5-157, step 8, from (1RS,5SR,6RS) 6-(4-methoxy-benzyloxymethyl)-3-oxa-bicyclo[3.1.0]hexan-2-one was prepared (1SR,2RS,3SR)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. White crystalline. 577 (M+H)$^+$.

Example 152

(1SR,2RS,3SR)-3-hydroxymethyl-cyclopropane-1,2-dicarboxylic acid 1-[(5-chloro-pyridin-2-yl)-amide] 2-{[2-fluoro-4-(2-oxo-2H-pyridin-1-yl)-phenyl]-amide} racemic

In analogy to example 132, step 2, from (1SR,2RS,3SR)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide} (example 151, step 3) was prepared (1SR,2RS,3SR)-3-hydroxymethyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Light yellow oil. MS: 455 (M−H)⁻.

Example 153

(1S,2R,3S)-3-hydroxymethyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

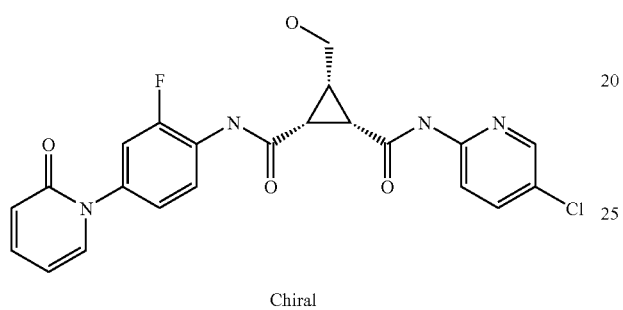

Chiral

In analogy to example 132, step 2, from (1S,2R,3S)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide} (example 150) was prepared (1S,2R,3S)-3-hydroxymethyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Light brown crystalline. MS: 455 (M−H)⁻.

Example 154

(1SR,2SR) 2-(5-chloro-pyridin-2-ylcarbamoyl)-1-[2-fluoro-4-(3-oxo-morpholin-4-yl)-phenylcarbamoyl]-cyclopropanecarboxylic acid allyl ester

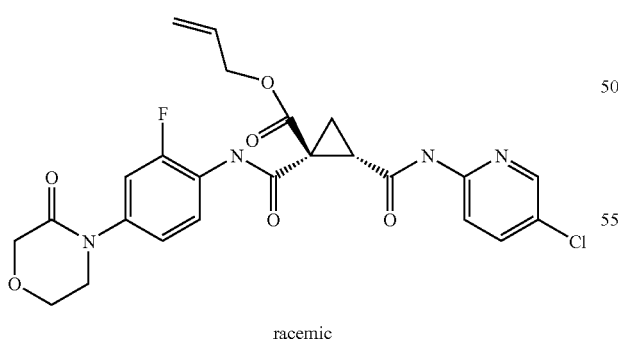

racemic

Step 1:
In analogy to example 141, step 2. from (1SR,2RS) 2,4-dioxo-3-oxa-bicyclo[3.1.0]hexane-1-carboxylic acid allyl ester (example 147, step 1) was prepared (1RS,2RS) 2-[2-fluoro-4-(3-oxo-morpholin-4-yl)-phenylcarbamoyl]-cyclopropane-1,1-dicarboxylic acid allyl ester. Off-white soliod. MS: 405 (M−H)⁻.

Step 2:
In analogy to example 141, step 3, from prepared (1RS,2RS) 2-[2-fluoro-4-(3-oxo-morpholin-4-yl)-phenylcarbamoyl]-cyclopropane-1,1-dicarboxylic acid allyl ester was prepared (1RS,2RS) 3-[2-fluoro-4-(3-oxo-morpholin-4-yl)-phenyl]-2,4-dioxo-3-aza-bicyclo[3.1.0]hexane-1-carboxylic acid allylester. Brown solid. MS: 389 (M+H)⁺.

Step 3:
In analogy to example 68, step 4, from (1RS,2RS) 3-[2-fluoro-4-(3-oxo-morpholin-4-yl)-phenyl]-2,4-dioxo-3-aza-bicyclo[3.1.0]hexane-1-carboxylic acid allylester and 2-amino-5-chloropyridine, was prepared (1SR,2SR) 2-(5-chloro-pyridin-2-ylcarbamoyl)-1-[2-fluoro-4-(3-oxo-morpholin-4-yl)-phenylcarbamoyl]-cyclopropanecarboxylic acid allyl ester. White Solid. MS: 515 (M−H)⁻.

Example 155

(1SR,2SR,3RS) 2-[4-(4-carboxymethoxy-2-oxo-2H-pyridin-1-yl)-2-fluoro-phenylcarbamoyl]-3-(4-chloro-phenylcarbamoyl)-cyclopropanecarboxylic acid ethyl ester

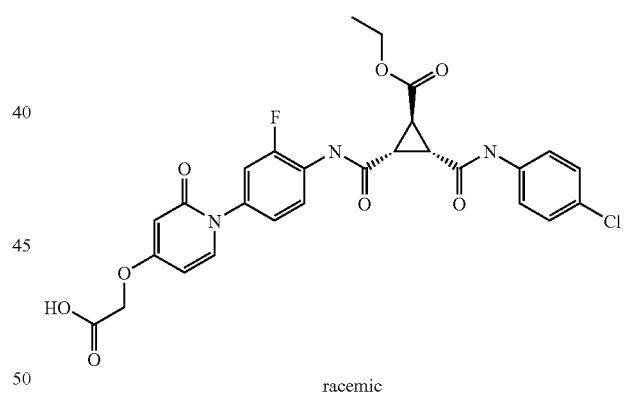

racemic

A solution of 49 mg (0.08 mmol) of (1SR,2SR,3RS)-2-[4-(4-tert-butoxycarbonylmethoxy-2-oxo-2H-pyridin-1-yl)-2-fluoro-phenylcarbamoyl]-3-(4-chloro-phenylcarbamoyl)-cyclopropanecarboxylic acid ethyl ester in 3 ml of 1,2-dichloromethane was treated with 28 ul of trifluoroacetic acid and stirred at 75° C. during 40 min. Evaporation of the solvents gave 31 mg (69%) (1SR,2SR,3RS) 2-[4-(4-carboxymethoxy-2-oxo-2H-pyridin-1-yl)-2-fluoro-phenylcarbamoyl]-3-(4-chloro-phenylcarbamoyl)-cyclopropanecarboxylic acid ethyl ester. Off-white solid. MS: 571 (M−H)⁻.

Example 156

(1SR,2RS)-1-Cyano-cyclopropane-1,2-dicarboxylic acid 2-[(5-chloro-pyridin-2-yl)-amide]1-{[2-fluoro-4-(2-oxo-2H-pyridin-1-yl)-phenyl]-amide}

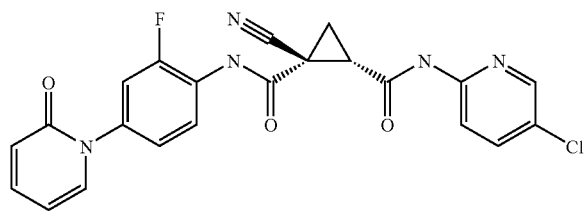

racemic

Step 1:

In analogy to example 157, step 5, from (1SR,2RS) 2-oxo-3-oxa-bicyclo[3.1.0]hexane-1 carbonitrile (obtained from cyano acetic acid allylester by application of procedures leading to similar 2-oxo-3-oxa-bicyclo[3.1.0]hexanes described by Toeke et al. Tetrahedron 1993, 49, p5133-5146 and by Burgess et al. J. Org. Chem. 1992, 57, p5931-5936) and 1-(4-amino-3-fluoro-phenyl)-1H-pyridin-2-one (prepared according to C. F. Bigge et al., patent application WO 2003045912) was prepared (1SR,2RS) 1-cyano-2-hydroxymethyl-cyclopropanecarboxylic acid [2-fluoro-4-(2-oxo-2H-pyridin-1-yl)-phenyl]-amide. Yellow solid. MS: 328 (M+H)+.

Step 2:

In analogy to example 157, step 6, from (1SR,2RS) 1-cyano-2-hydroxymethyl-cyclopropanecarboxylic acid [2-fluoro-4-(2-oxo-2H-pyridin-1-yl)-phenyl]-amide and Jones reagent was prepared (1SR,2RS) 2-cyano-2-[2-fluoro-4-(2-oxo-2H-pyridin-1-yl)-phenylcarbamoyl]-cyclopropanecarboxylic acid. Yellow solid. MS: 340 (M−H)−.

Step 3:

In analogy to example 157, step 7, from (1SR,2RS) 2-cyano-2-[2-fluoro-4-(2-oxo-2H-pyridin-1-yl)-phenylcarbamoyl]-cyclopropanecarboxylic acid and iodomethane was prepared (1SR,2RS) 2-cyano-2-[2-fluoro-4-(2-oxo-2H-pyridin-1-yl)-phenylcarbamoyl]-cyclopropanecarboxylic acid methyl ester. Yellow solid. MS: 354 (M−H)−.

Step 4:

In analogy to example 100, step 3, from 2-amino-5-chloropyridine and (1SR,2RS) 2-cyano-2-[2-fluoro-4-(2-oxo-2H-pyridin-1-yl)-phenylcarbamoyl]-cyclopropanecarboxylic acid methyl ester was prepared (1SR,2RS)-1-cyano-cyclopropane-1,2-dicarboxylic acid 2-[(5-chloro-pyridin-2-yl)-amide]1-{[2-fluoro-4-(2-oxo-2H-pyridin-1-yl)-phenyl]-amide}. Colorless foam. MS: 452 (M+H)+.

Example 157

(1S,2R,3R)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

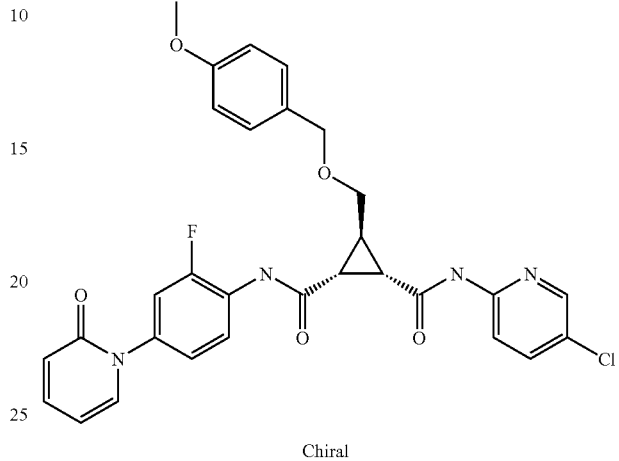

Chiral

Step 1:

A solution of 11.8 g (133.4 mmol) of trans 2-butene-1,4-diol in 100 ml of DMF was treated with 6.4 g (147 mmol) of sodium hydride dispersion on oil (55%), stirred at 0° C. for 45 min., and treated dropwise with 25.1 g (160 mmol) of 4-methoxybenzylchloride. The mixture was stirred during 5 hrs at RT and then poured into a saturated aqueous solution of NaCl. Extraction with AcOEt, drying of the combined organic phases over Na$_2$SO$_4$, filtration, evaporation of the solvent and chromatography on silica gel with heptane/AcOEt 9:1 gave 5.7 g (21%) of trans 4-(4-methoxy-benzyloxy)-but-2-en-1-ol. Light yellow oil. MS: 207 (M−H)−.

Step 2:

A solution of 4.7 g (22.6 mmol) 4-(4-methoxy-benzyloxy)-but-2-en-1-ol in 100 ml THF was treated with 90 mg (1.13 mmol) of sodium acetate and heated to reflux. To this mixture were added dropwise 1.9 ml (24.8 mmol) of diketene and refluxing was continued for 10 hrs. After cooling to RT the solvent was partly evaporated and the mixture poured into a saturated aqueous solution of NaCl. Extraction with AcOEt, drying of the combined organic phases over Na$_2$SO$_4$, filtration, evaporation of the solvent chromatography on silica gel with heptane/AcOEt 2: gave 4.29 g (65%) of trans 3-oxo-butyric acid 4-(4-methoxy-benzyloxy)-but-2-enyl ester. Light yellow oil. MS: 291 (M−H)−.

Step 3:

A solution of 4.29 g (14.7 mmol) of trans 3-oxo-butyric acid 4-(4-methoxy-benzyloxy)-but-2-enyl ester in 150 ml of acetonitrile was treated with 3.27 ml (19.1 mmol) N,N-ethyl diisopropylamine and then within 30 min. with a solution of 4.58 g (19.1 mmol) of 4-acetamidobenzenesulfonyl azide in 25 ml of acetonitrile. The mixture was stirred at RT during 2.5 hrs and treated with 44 ml of a 1M aqueous LiOH solution. Stirring was continued for 10 hrs and the mixture poured into a saturated aqueous NaCl solution. Extraction with Et2O/AcOEt 2:1, drying of the combined organic phases over Na$_2$SO$_4$, filtration, evaporation of the solvent and chromatography on silica gel with heptane/AcOEt 2:1 gave 2.87 g (70%) of diazo-acetic acid trans 4-(4-methoxy-benzyloxy)-but-2-enyl ester. Yellow oil.

Step 4:

To a solution of 1 g (3.6 mmol) of diazo-acetic acid 4-(4-methoxy-benzyloxy)-but-2-enyl ester in 50 ml dichloromethane under reflux were added within 8 hrs of 25 mg (0.03 mmol) of $Rh_2$ (5S-MEPY)$_4$ (Doyle dirhodium catalyst from Acros, CAS: 132435-65-5) dissolved in 100 ml of dichloromethane. Refluxing for another 20 hrs, evaporation of the solvent and chromatography on silica gel with heptane/AcOEt gave 850 mg (96%, >92% ee) of (1R,5S, 6S) 6-(4-methoxy-benzyloxymethyl)-3-oxa-bicyclo[3.1.0]hexan-2-one. Colorless oil. MS: 247 (M–H)$^-$.

Step 5:

A solution of 850 mg (3.4 mmol) of 1-(4-amino-3-fluoro-phenyl)-1H-pyridin-2-one (prepared according to C. F. Bigge et al., patent application WO 2003045912) in 80 ml of THF was cooled to –78° C., treated dropwise with 4.8 ml of a 1M lithium bis(trimethylsilyl)amide-solution in THF and stirred for 30 min at 78° C. To this solution were added 839 mg (4.8 mmol) of (1R,5S,6S) 6-(4-methoxy-benzyloxymethyl)-3-oxa-bicyclo[3.1.0]hexan-2-one dissolved in 5 ml of THF. Stirring was continued at –78° C. for 1 hr and then for 3 hrs at RT. Pouring of the mixture into a 2M aqueous solution of HCl, extraction with AcOEt, drying of the combined organic phases over $Na_2SO_4$, filtration and evaporation of the solvent gave 1.2 g (77%) of (1S,2S,3S) 2-hydroxymethyl-3-(4-methoxy-benzyloxymethyl)-cyclopropanecarboxylic acid [2-fluoro-4-(2-oxo-2H-pyridin-1-yl)-phenyl]-amide. Yellow semisolid. 453 (M+H)$^+$.

Step 6:

A solution of 100 mg (0.22 mmol) of (1S,2S,3S) 2-hydroxymethyl-3-(4-methoxy-benzyloxymethyl)-cyclopropanecarboxylic acid [2-fluoro-4-(2-oxo-2H-pyridin-1-yl)-phenyl]-amide in 5 ml of acetone was cooled to 0° and treated dropwise with 1 ml of Jones reagent. After stirring during 2 hrs at RT the mixture was treated with 50 mg of $NaHSO_3$ and the solution separated from the green precipitate. Drying of the solution over $Na_2SO_4$, filtration, and evaporation of the solvent gave 90 mg (90%) (1S,2R,3R) 2-[2-fluoro-4-(2-oxo-2H-pyridin-1-yl)-phenylcarbamoyl]-3-(4-methoxy-phenoxymethyl)-cyclopropanecarboxylicacid. Greenish solid. MS: 451 (M–H)$^-$.

Step 7:

A solution of 90 mg (0.19 mmol) of (1S,2R,3R) 2-[2-fluoro-4-(2-oxo-2H-pyridin-1-yl)-phenylcarbamoyl]-3-(4-methoxy-phenoxymethyl)-cyclopropanecarboxylic acid in 3 ml of DMF was treated with 100 mg of $K_2CO_3$ and 0.5 ml ml of iodomethane. The mixture was stirred for 3 hrs and poured into a diluted aqueous solution of NaOH. Extraction with AcOEt, drying of the combined organic phases over $Na_2SO_4$, filtration and evaprotation of the solvent gave 90 mg (97%) of (1S,2R,3R) 2-[2-fluoro-4-(2-oxo-2H-pyridin-1-yl)-phenylcarbamoyl]-3-(4-methoxy-phenoxymethyl)-cyclopropanecarboxylicacid methyl ester. Yellow oil. MS: 467 (M+H)$^+$.

Step 8:

In analogy to example 100, step 3, from 2-amino-5-chloropyridine and (1S,2R,3R) 2-[4-(acryloyl-propenyl-amino)-2-fluoro-phenylcarbamoyl]-3-(4-methoxy-benzyloxymethyl) cyclopropanecarboxylic acid methyl ester was prepared (1S,2R,3R)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Colorless foam. MS: 577 (M+H)$^+$.

Example 158

(1SR,2RS,3RS)-3-methoxymethyl-cyclopropane-1, 2-dicarboxylic acid 1-{[4-(4-carbamoylmethoxy-2-oxo-2H-pyridin-1-yl)-2-fluoro-phenyl]-amide}2-[(4-chloro-phenyl)-amide]

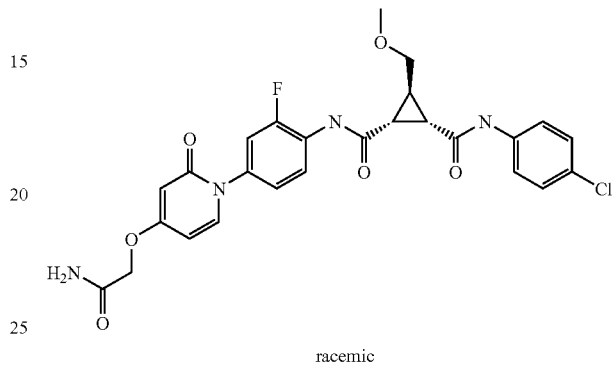

racemic

In analogy to example 143, from (1SR,2RS,3RS)-3-methoxymethyl-cyclopropane-1,2-dicarboxylic acid 1-[(4-chloro-phenyl)-amide]2-{[2-fluoro-4-(4-hydroxy-2-oxo-2H-pyridin-1-yl)-phenyl]-amide} (example 161) 2-bromoacetamide was prepared (1SR,2RS,3RS)-3-methoxymethyl-cyclopropane-1,2-dicarboxylic acid 1-{[4-(4-carbamoylmethoxy-2-oxo-2H-pyridin-1-yl)-2-fluoro-phenyl]-amide}2-[(4-chloro-phenyl)-amide]. Light yellow solid. MS: 543 (M+H)$^+$.

Example 159

(1SR,2RS,3RS)-3-hydroxymethyl-cyclopropane-1,2-dicarboxylic acid 1-{[4-(4-benzyloxy-2-oxo-2H-pyridin-1-yl)-2-fluoro-phenyl]-amide}2-[(4-chloro-phenyl)-amide]

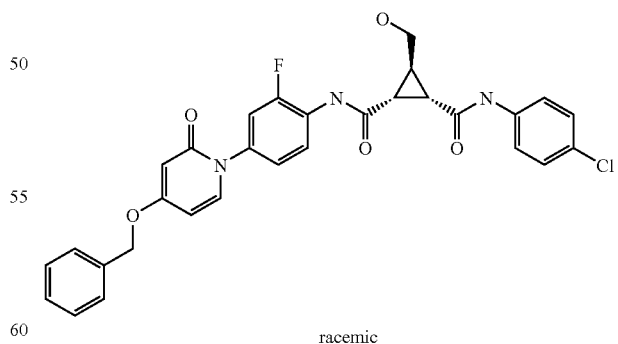

racemic

In analogy example 140, from (1SR,2RS,3SR)-2-[4-(4-benzyloxy-2-oxo-2H-pyridin-1-yl)-2-fluoro-phenylcarbamoyl]-3-(4-chloro-phenylcarbamoyl)-cyclopropanecarboxylic acid ethyl ester (example 144) was prepared (1SR,2RS,3RS)-3-hydroxymethyl-cyclopropane-1,2-dicarboxylic acid 1-{[4-

(4-benzyloxy-2-oxo-2H-pyridin-1-yl)-2-fluoro-phenyl]-amide}2-[(4-chloro-phenyl)-amide]. Yellow solid. MS: 562 (M+H)+.

Example 160

(1SR,2RS,3SR)-3-methoxymethyl-cyclopropane-1,2-dicarboxylic acid 1-{[4-(4-benzyloxy-2-oxo-2H-pyridin-1-yl)-2-fluoro-phenyl]-amide}2-[(4-chloro-phenyl)-amide]

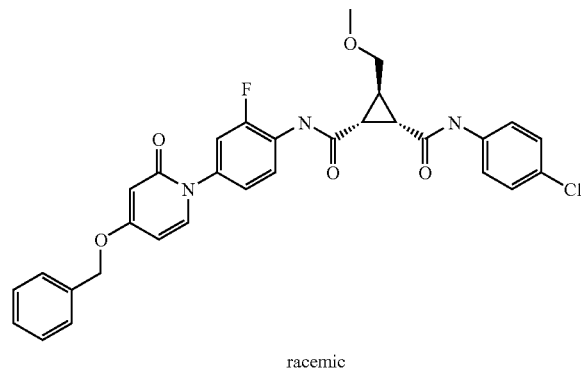

racemic

Step 1:

In analogy to example 133, step 1, from (1SR,2RS,3SR)-3-hydroxymethyl-cyclopropane-1,2-dicarboxylic acid 1-{[4-(4-benzyloxy-2-oxo-2H-pyridin-1-yl)-2-fluoro-phenyl]-amide}2-[(4-chloro-phenyl)-amide] (example 159) was prepared (1SR,2RS,3SR)-methanesulfonic acid 2-[4-(4-benzyloxy-2-oxo-2H-pyridin-1-yl)-2-fluoro-phenylcarbamoyl]-3-(5-chloro-pyridin-2-ylcarbamoyl)-cyclopropylmethyl ester. Yellow oil. MS: 642 (M+H)+.

Step 2:

In analogy to example 133, step 2, from (1SR,2RS,3SR)-methanesulfonic acid 2-[4-(4-benzyloxy-2-oxo-2H-pyridin-1-yl)-2-fluoro-phenylcarbamoyl]-3-(5-chloro-pyridin-2-yl-carbamoyl)-cyclopropylmethyl ester and sodium methoxide in methanol, was prepared (1SR,2RS,3SR)-3-methoxymethyl-cyclopropane-1,2-dicarboxylic acid 1-{[4-(4-benzyloxy-2-oxo-2H-pyridin-1-yl)-2-fluoro-phenyl]-amide}2-[(4-chloro-phenyl)-amide]. Brown solid. MS: 577 (M+H)+.

Example 161

(1SR,2RS,3SR)-3-methoxymethyl-cyclopropane-1,2-dicarboxylic acid 1-[(4-chloro-phenyl)-amide]2-{[2-fluoro-4-(4-hydroxy-2-oxo-2H-pyridin-1-yl)-phenyl]-amide}

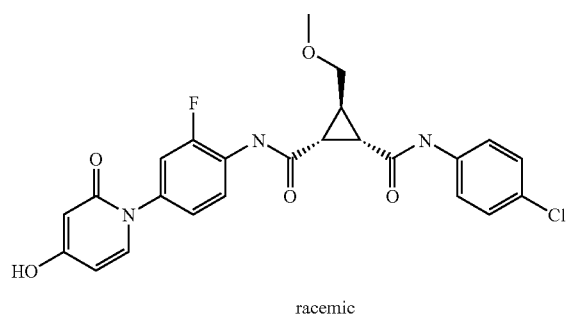

racemic

A solution of 100 mg (0.17 mmol) of (1SR,2RS,3SR)-3-methoxymethyl-cyclopropane-1,2-dicarboxylic acid 1-{[4-(4-benzyloxy-2-oxo-2H-pyridin-1-yl)-2-fluoro-phenyl]-amide}2-[(4-chloro-phenyl)-amide] (example 160, step 2) in 10 ml of methanol was treated with 43 mg of Pd/C (10%) and hydrogenated at atmospheric pressure during 30 min. Filtration and evaporation of the solvent gave 70 mg (80%) of (1SR,2RS,3SR)-3-methoxymethyl-cyclopropane-1,2-dicarboxylic acid 1-[(4-chloro-phenyl)-amide]2-{[2-fluoro-4-(4-hydroxy-2-oxo-2H-pyridin-1-yl)-phenyl]-amide}. Colorless solid. MS: 484 (M−H)−.

Example 162

[1-(4-{[(1SR,2RS,3SR)-2-(4-chloro-phenylcarbamoyl)-3-methoxymethyl-cyclopropanecarbonyl]-amino}-3-fluoro-phenyl)-2-oxo-1,2-dihydro-pyridin-4-yloxy]-acetic acid tert-butyl ester

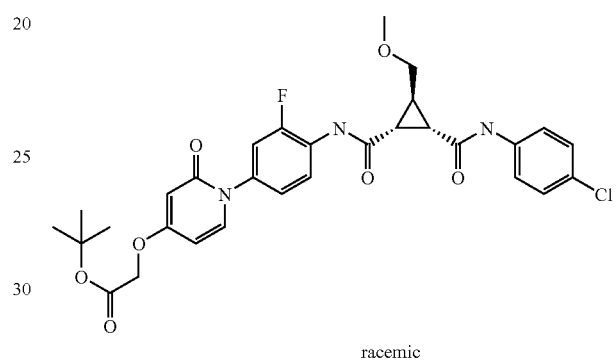

racemic

In analogy to example 143, from (1SR,2RS,3SR)-3-methoxymethyl-cyclopropane-1,2-dicarboxylic acid 1-[(4-chloro-phenyl)-amide]2-{[2-fluoro-4-(4-hydroxy-2-oxo-2H-pyridin-1-yl)-phenyl]-amide} (example 162) and tert-butylbromoacetate was prepared [1-(4-{[(1SR,2RS,3SR)-2-(4-hloro-phenylcarbamoyl)-3-methoxymethyl-cyclopropanecarbonyl]-amino}-3-fluoro-phenyl)-2-oxo-1,2-dihydro-pyridin-4-yloxy]-acetic acid tert-butyl ester. Colorless solid. MS: 600 (M+H)+.

Example 163

[1-(4-{[(1SR,2RS,3SR)-2-(4-chloro-phenylcarbamoyl)-3-methoxymethyl-cyclopropanecarbonyl]-amino}-3-fluoro-phenyl)-2-oxo-1,2-dihydro-pyridin-4-yloxy]-acetic acid

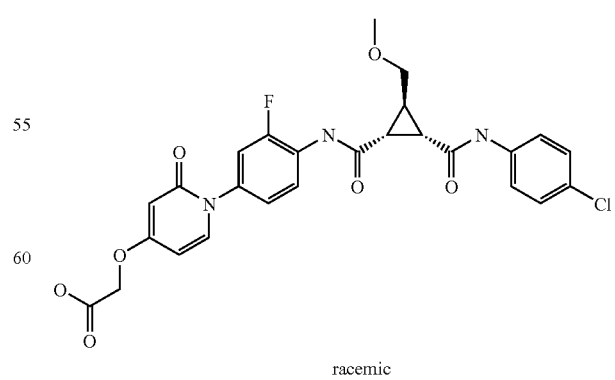

racemic

In analogy to example 155, from [1-(4-{[(1SR,2RS,3SR)-2-(4-chloro-phenylcarbamoyl)-3-methoxymethyl-cyclopropanecarbonyl]-amino}-3-fluoro-phenyl)-2-oxo-1,2-dihydro-pyridin-4-yloxy]-acetic acid tert-butyl ester (example 162) was prepared [1-(4-{[(1SR,2RS,3SR)-2-(4-chloro-phenylcarbamoyl)-3-methoxymethyl-cyclopropanecarbonyl]-amino}-3-fluoro-phenyl)-2-oxo-1,2-dihydro-pyridin-4-yloxy]-acetic acid. Brown solid. MS: 544 (M+H)+.

Example 164

(1SR,2RS,3SR)-3-methoxymethyl-cyclopropane-1,2-dicarboxylic acid 1-[(4-chloro-phenyl)-amide]2-{[4-(4-dimethylcarbamoylmethoxy-2-oxo-2H-pyridin-1-yl)-2-fluoro-phenyl]-amide}

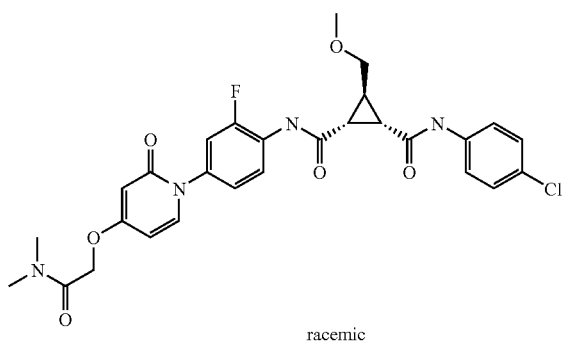

racemic

In analogy to example 149, from [1-(4-{[(1SR,2RS,3SR)-2-(4-Chloro-phenylcarbamoyl)-3-methoxymethyl-cyclopropanecarbonyl]-amino}-3-fluoro-phenyl)-2-oxo-1,2-dihydro-pyridin-4-yloxy]-acetic acid (example 163) was prepared (1SR,2RS,3SR)-3-methoxymethyl-cyclopropane-1,2-dicarboxylic acid 1-[(4-chloro-phenyl)-amide]2-{[4-(4-dimethylcarbamoylmethoxy-2-oxo-2H-pyridin-1-yl)-2-fluoro-phenyl]-amide}. White solid. MS: 571 (M+H)+.

Example 165

(1RS,2RS)-2-(4-chloro-phenylcarbamoyl)-1-[2-fluoro-4-(2-oxo-2H-pyridin-1-yl)-phenylcarbamoyl]-cyclopropanecarboxylic acid

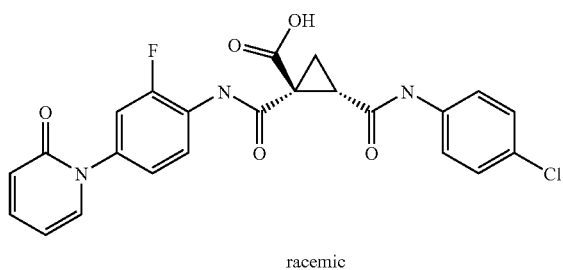

racemic

Step 1:
In analogy to example 141, step 2, from (1RS,2RS) 2,4-dioxo-3-oxa-bicyclo[3.1.0]hexane-1-carboxylic acid allyl ester (example 147, step 3) and 1-(4-amino-3-fluoro-phenyl)-1H-pyridin-2-one (prepared according to C.F. Bigge et al., patent application WO 2003045912) was prepared (1RS, 2RS) 2-[2-fluoro-4-(2-oxo-2H-pyridin-1-yl)-phenylcarbamoyl]-cyclopropane-1,1-dicarboxylic acid allyl ester. Light brown crystalline. MS: 401 (M+H)+.

Step 2:
In analogy to example 147, step 3, from (1RS,2RS) 2-[2-fluoro-4-(2-oxo-2H-pyridin-1-yl)-phenylcarbamoyl]-cyclopropane-1,1-dicarboxylic acid allyl ester, was prepared (1RS, 2RS) 3-[2-fluoro-4-(2-oxo-2H-pyridin-1-yl)-phenyl]-2,4-dioxo-3-aza-bicyclo[3.1.0]hexane-1-carboxylic acid allyl ester. Light yellow crystalline. MS: 383 (M+H)+.

Step 3:
A solution of 1.13 g (2.96 mmol) of (1RS,2RS) 3-[2-fluoro-4-(2-oxo-2H-pyridin-1-yl)-phenyl]-2,4-dioxo-3-aza-bicyclo[3.1.0]hexane-1-carboxylic acid allyl ester in 30 ml of dichloromethane/THF 1:1 was treated with 257 ul (2.96 mmol) of morpholine and 103 mg (0.09 mmol) of palladiumtetrakis(triphenylphosphine) and stirred 1.5 hrs at RT. The mixture was poured into a ca. 2M aqueous solution of sodium bicarbonate and extracted with ether. The aqueous phase was acidified with aqueous HCl to a pH of ca. 1 and extracted with AcOEt. Drying of the combined organic phases over Na$_2$SO$_4$, filtration and evaporation of the solvent gave 823 mg (81%) of (1RS,2RS) 3-[2-fluoro-4-(2-oxo-2H-pyridin-1-yl)-phenyl]-2,4-dioxo-3-aza-bicyclo[3.1.0]hexane-1-carboxylic acid. White crystalline. MS: 343 (M+H)+.

Step 4:
A solution of 223 mg (1.75 mmol) of 4-chloroaniline in 10 ml of THF was cooled to −78° C. and treated dropwise with 1.75 ml of a 1M lithium bis(trimethylsilyl)amide-solution in THF and stirred for 30 min. To this solution 200 mg (0.58 mmol) of (1RS,2RS) 3-[2-fluoro-4-(2-oxo-2H-pyridin-1-yl)-phenyl]-2,4-dioxo-3-aza-bicyclo[3.1.0]hexane-1-carboxylic acid were added portionwise and the mixture was allowed to reach RT within a few hours. The mixture was then poured into a ca 2M aqueous solution of sodium bicarbonate and extracted with ether. The aqueous phase was acidified with aqueous HCl to a pH of ca. 1 and extracted with AcOEt. The combined organic phases were dried with Na$_2$SO$_4$. Filtration and evaporation of the solvent gave a 58 mg (77%) of (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid. Light yellow crystalline. MS: 468 (M−H)−.

Example 166

(1RS,2RS)-cyclopropane-1,1,2-tricarboxylic acid 2-[(4-chloro-phenyl)-amide]1-dimethylamide 1-{[2-fluoro-4-(2-oxo-2H-pyridin-1-yl)-phenyl]-amide}

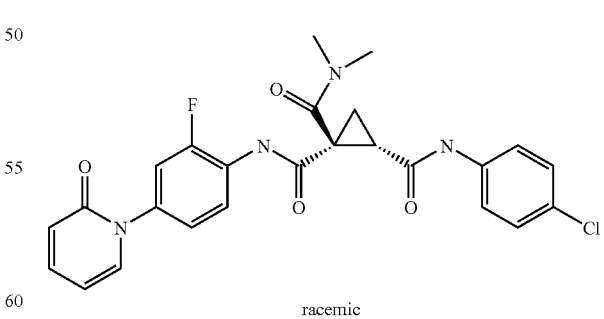

racemic

In analogy to example 72, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid (example 165) and dimethyl amine hydrochloride was prepared (1RS, 2RS)-cyclopropane-1,1,2-tricarboxylic acid 2-[(4-chlorophenyl)-amide]1-dimethylamide 1-{[2-fluoro-4-(2-oxo-2H-pyridin-1-yl)-phenyl]-amide}. Light brown oil. MS: 497 (M+H)⁺.

Example 167

(1RS,2RS)— 1-(pyrrolidine-1-carbonyl)-cyclopropane-1,2-dicarboxylic acid 2-[(4-chloro-phenyl)-amide]1-{[2-fluoro-4-(2-oxo-2H-pyridin-1-yl)-phenyl]-amide}

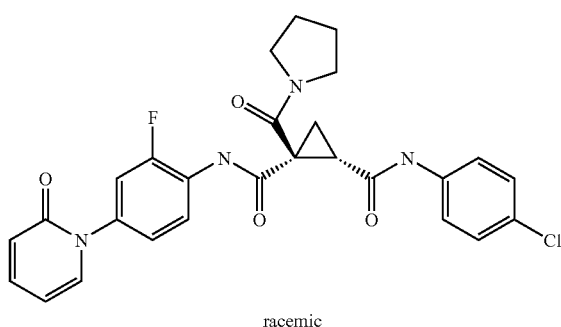

racemic

In analogy to example 72, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid (example 165) and pyrrolidine was prepared (1RS,2RS)-1-(pyrrolidine-1-carbonyl)-cyclopropane-1,2-dicarboxylic acid 2-[(4-chloro-phenyl)-amide]1-{[2-fluoro-4-(2-oxo-2H-pyridin-1-yl)-phenyl]-amide}. Light yellow crystalline. MS: 521 (M−H)⁻.

Example 168

(1RS,2RS)-cyclopropane-1,1,2-tricarboxylic acid 2-[(4-chloro-phenyl)-amide]1-(ethyl-methyl-amide) 1-{[2-fluoro-4-(2-oxo-2H-pyridin-1-yl)-phenyl]-amide}

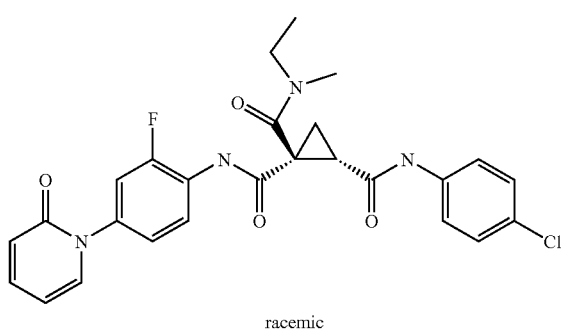

racemic

In analogy to example 72, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid (example 165) and ethylmethylamine hydrochloride was prepared (1RS,2RS)-cyclopropane-1,1,2-tricarboxylic acid 2-[(4-chloro-phenyl)-amide]1-(ethyl-methyl-amide) 1-{[2-fluoro-4-(2-oxo-2H-pyridin-1-yl)-phenyl]-amide}. Light yellow crystalline. MS: 509 (M−H)⁻.

Example 169

(1SR,2RS)-cyclopropane-1,1,2-tricarboxylic acid 1-amide 2-[(4-chloro-phenyl)-amide]1-{[2-fluoro-4-(2-oxo-2H-pyridin-1-yl)-phenyl]-amide}

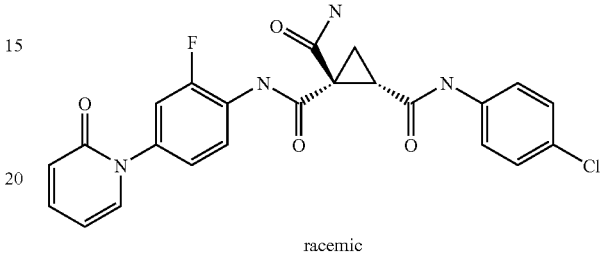

racemic

In analogy to example 72, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid (example 165) and ammonium chloride was prepared (1SR,2RS)-cyclopropane-1,1,2-tricarboxylic acid 1-amide 2-[(4-chloro-phenyl)-amide]1-{[2-fluoro-4-(2-oxo-2H-pyridin-1-yl)-phenyl]-amide}. White crystalline. MS: 467 (M−H)⁻.

Example 170

(1RS,2RS)-1-(morpholine-4-carbonyl)-cyclopropane-1,2-dicarboxylic acid 2-[(4-chloro-phenyl)-amide]1-{[2-fluoro-4-(2-oxo-2H-pyridin-1-yl)-phenyl]-amide}

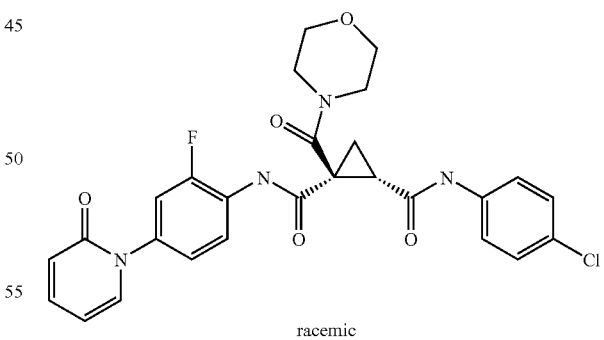

racemic

In analogy to example 72, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid (example 165) and morpholine was prepared (1RS,2RS)-1-(morpholine-4-carbonyl)-cyclopropane-1,2-dicarboxylic acid 2-[(4-chloro-phenyl)-amide]1-{[2-fluoro-4-(2-oxo-2H-pyridin-1-yl)-phenyl]-amide}. Light yellow crystalline. MS: 539 (M+H)⁺.

Example 171

(1RS,2RS)-2-(4-chloro-phenylcarbamoyl)-1-[2-fluoro-4-(2-oxo-2H-pyridin-1-yl)-phenylcarbamoyl]-cyclopropanecarboxylic acid methyl ester

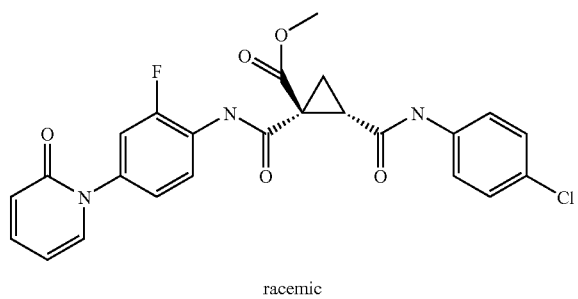

racemic

In analogy to example 157, step 7, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid (example 165) and iodomethane was prepared (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid methyl ester. Yellow oil. MS: 482 (M−H)⁻.

Example 172

(1RS,2RS)-1-(piperidine-1-carbonyl)-cyclopropane-1,2-dicarboxylic acid 2-[(4-chloro-phenyl)-amide]1-{[2-fluoro-4-(2-oxo-2H-pyridin-1-yl)-phenyl]-amide}

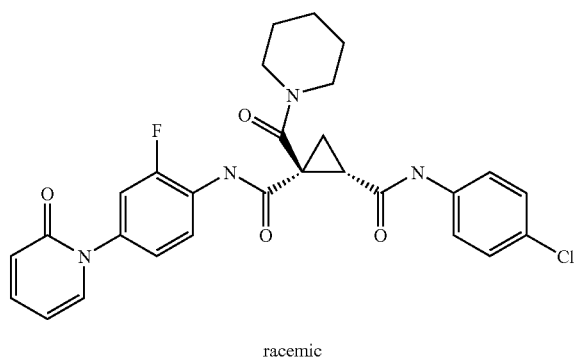

racemic

In analogy to example 72, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid (example 165) and piperidine was prepared (1RS,2RS)-1-(piperidine-1-carbonyl)-cyclopropane-1,2-dicarboxylic acid 2-[(4-chloro-phenyl)-amide]1-{[2-fluoro-4-(2-oxo-2H-pyridin-1-yl)-phenyl]-amide}. Light yellow oil. MS: 535 (M−H)⁻.

Example 173

(1SR,2RS)-1-hydroxymethyl-cyclopropane-1,2-dicarboxylic acid 2-[(4-chloro-phenyl)-amide]1-{[2-fluoro-4-(2-oxo-2H-pyridin-1-yl)-phenyl]-amide}

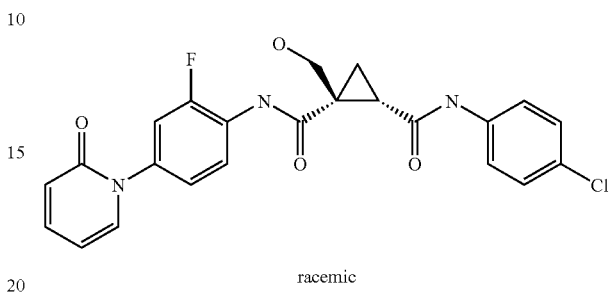

racemic

In analogy to example 148, from (1RS,2RS)-2-(4-chloro-phenylcarbamoyl)-1-[2-fluoro-4-(2-oxo-2H-pyridin-1-yl)-phenylcarbamoyl]-cyclopropanecarboxylic acid methyl ester (example 171) and sodium borohydride was prepared (1SR,2RS)-1-hydroxymethyl-cyclopropane-1,2-dicarboxylic acid 2-[(4-chloro-phenyl)-amide]1-{[2-fluoro-4-(2-oxo-2H-pyridin-1-yl)-phenyl]-amide}. White crystalline. MS: 454 (M−H)⁻.

Example 174

(1RS,2RS)-1-(4-chloro-phenylcarbamoyl)-2-[2-fluoro-4-(2-oxo-2H-pyridin-1-yl)-phenylcarbamoyl]-cyclopropanecarboxylic acid methyl ester

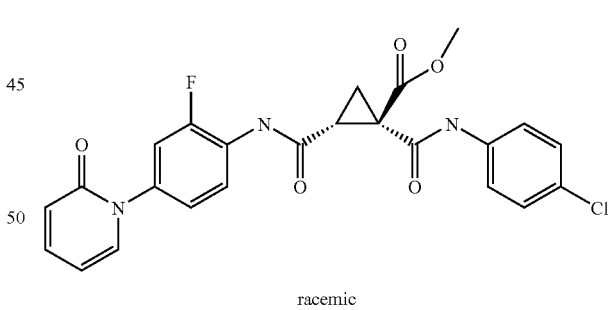

racemic

In analogy to example 165, step 3, from (1RS,2RS)-1-(4-chloro-phenylcarbamoyl)-2-[2-fluoro-4-(2-oxo-2H-pyridin-1-yl)-phenylcarbamoyl]-cyclopropanecarboxylic acid (1RS,2RS)-1-(4-chloro-phenylcarbamoyl)-2-[2-fluoro-4-(2-oxo-2H-pyridin-1-yl)-phenylcarbamoyl]-cyclopropanecarboxylic acid that in analogy to example 157, step 7 was methylated to (1RS,2RS)-1-(4-chloro-phenylcarbamoyl)-2-[2-fluoro-4-(2-oxo-2H-pyridin-1-yl)-phenylcarbamoyl]-cyclopropanecarboxylic acid methyl ester. Light yellow oil. MS: 482 (M−H)⁻.

Example 175

(1SR,2RS)-cyclopropane-1,2-dicarboxylic acid 1-[(5-chloro-pyridin-2-yl)-amide]2-{[2-fluoro-4-(3-oxo-morpholin-4-yl)-phenyl]-amide}

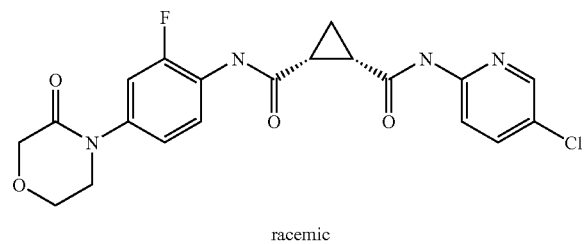

racemic

Step 1:

In analogy to example 114, step 5, from 3-oxa-bicyclo[3.1.0]hexane-2,4-dione (purchased from ACROS, cat-No: 37012-0010) and 4-(4-amino-3-fluoro-phenyl)-morpholin-3-one (prepared according to C. F. Bigge et al., patent application WO 2003045912) was (1SR,2RS) 3-[2-fluoro-4-(3-oxo-morpholin-4-yl)-phenyl]-3-aza-bicyclo[3.1.0]hexane-2,4-dione. Off-white solid. MS: 321 (M−H)⁻.

Step 2:

In analogy to example 114, step 6. from (1SR,2RS) 3-[2-Fluoro-4-(3-oxo-morpholin-4-yl)-phenyl]-3-aza-bicyclo[3.1.0]hexane-2,4-dione and 2-amino-5-chloropyridine was prepared (1SR,2RS)-cyclopropane-1,2-dicarboxylic acid 1-[(5-chloro-pyridin-2-yl)-amide]2-{[2-fluoro-4-(3-oxo-morpholin-4-yl)-phenyl]-amide}. White solid. MS: 433 (M+H)⁺.

Example 176

(1SR,2SR,3RS)-2-(4-chloro-phenylcarbamoyl)-3-[4-(2-oxo-2H-pyridin-1-yl)-phenyl-carbamoyl]-cyclopropanecarboxylic acid ethyl ester

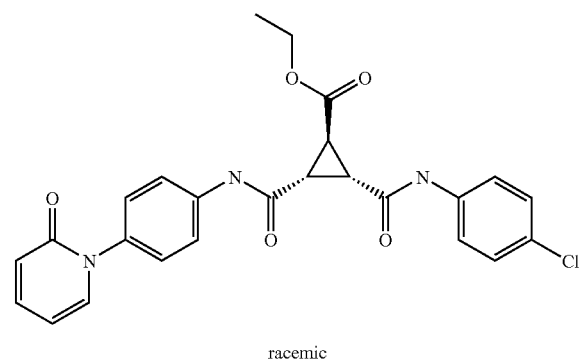

racemic

In analogy to example 68, step 4, from 1-(4-amino-phenyl)-1H-pyridin-2-one (prepared according to C. F. Bigge et al., patent application WO 2003045912) and (1RS,5SR,6RS)-3-(4-chloro-phenyl)-2,4-dioxo-3-aza-bicyclo[3.1.0]hexane-6-carboxylic acid ethyl ester was prepared (1SR,2SR,3RS)-2-(4-chloro-phenylcarbamoyl)-3-[4-(2-oxo-2H-pyridin-1-yl)-phenyl-carbamoyl]-cyclopropanecarboxylic acid ethyl ester. Light brown amorphous solid. MS: 480 (M+H)⁺.

Example 177

(1SR,2SR,3RS)-2-(4-chloro-phenylcarbamoyl)-3-[4-(2-oxo-2H-pyridin-1-yl)-phenyl-carbamoyl]-cyclopropanecarboxylic acid

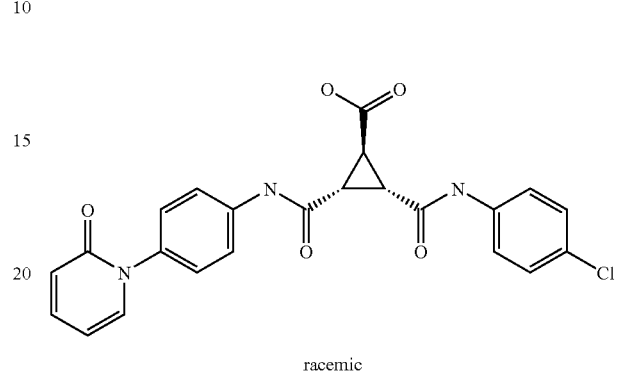

racemic

In analogy to example 69, from (1SR,2SR,3RS)-2-(4-chloro-phenylcarbamoyl)-3-[4-(2-oxo-2H-pyridin-1-yl)-phenylcarbamoyl]-cyclopropanecarboxylic acid ethyl ester was prepared (1SR,2SR,3RS)-2-(4-chloro-phenylcarbamoyl)-3-[4-(2-oxo-2H-pyridin-1-yl)-phenyl-carbamoyl]-cyclopropanecarboxylic acid. Off-white solid. MS: 450 (M−H)⁻.

Example 178

(1SR,2RS)-1-methyl-cyclopropane-1,2-dicarboxylic acid 2-[(5-chloro-pyridin-2-yl)-amide]1-{[2-fluoro-4-(2-oxo-pyridin-1-yl)-phenyl]-amide}

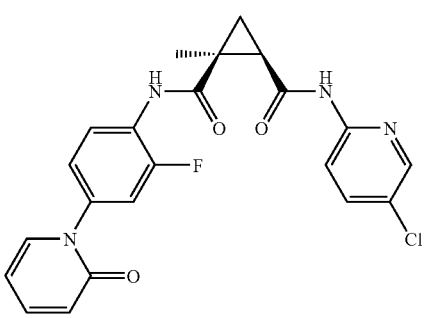

Step 1:

A mixture of 1-methyl-1,2-cyclopropanedicarboxylic acid (0.4 g; CAS 82235-80-1) in trifluoroacetic anhydride (5 ml) was stirred under an argon atmosphere for 2 hrs at r.t. The clear solution was concentrated at 0° C. to leave the intermediate anhydride as colorless oil. This residue was dissolved in THF (5 ml), cooled to 0° C. and treated with 2-amino-5-chloropyridine (0.5 g). Stirring was continued over night at r.t. whereby the suspension turned into a slightly yellow solution, then into a white slurry. The reaction mixture was concentrated. The crude product was purified by column chromatography (silica gel; gradient: $CH_2Cl_2$->$CH_2Cl_2$/MeOH 9:1) to give (1SR,2RS)-2-(5-chloro-pyridin-2-ylcarbamoyl)-1-methyl-cyclopropane-carboxylic acid (182 mg) as white solid. MS 253.1 ([M–H]⁻).

Step 2:

A suspension of (1SR,2RS)-2-(5-chloro-pyridin-2-ylcarbamoyl)-1-methyl-cyclopropane-carboxylic acid (176 mg) in MeOH (5 ml) was cooled to 0° C. and treated with thionyl chloride (15 drops). After stirring for 2 hrs at 0° C. additional thionyl chloride (10 drops) was added. The clear solution was concentrated. The crude product was purified by column chromatography (silica gel; gradient: CH₂Cl₂–>CH₂Cl₂/MeOH 9:1) to give (1SR,2RS)-2-(5-chloro-pyridin-2-ylcarbamoyl)-1-methyl-cyclopropanecarboxylic acid methyl ester (163 mg) as colorless amorphous solid. MS 269.5 ([M+H]⁺).

Step 3:

A suspension of 1-(4-amino-3-fluoro-phenyl)-1H-pyridin-2-one (447 mg; CAS 536747-52-1, prepared according to C. F. Bigge et al., patent application WO 2003045912) in dioxane (8 ml) was treated with trimethyl aluminium (2M in heptane; 1.09 ml) at r.t. under an argon atmosphere. After stirring for 2 hrs at r.t., (1SR,2RS)-2-(5-chloro-pyridin-2-ylcarbamoyl)-1-methyl-cyclo-propanecarboxylic acid methyl ester (147 mg) was added. The reaction was heated over night at 100° C. The slurry was cooled to r.t. and treated with H₂O (0.8 ml). After stirring for 15 min, Na₂SO₄ was added. After stirring for 15 min, the mixture was filtered, and the filtrate was concentrated. The crude product was purified by column chromatography (silica gel; gradient: CH₂Cl₂–>CH₂Cl₂/MeOH) to give (1SR,2RS)-1-methyl-cyclopropane-1,2-dicarboxylic acid 2-[(5-chloro-pyridin-2-yl)-amide]1-{[2-fluoro-4-(2-oxo-pyridin-1-yl)-phenyl]-amide} (180 mg) as off-white solid. MS: 441.3 ([M+H]⁺)

Example 179

(1S,2R)-1-methyl-cyclopropane-1,2-dicarboxylic acid 2-[(5-chloro-pyridin-2-yl)-amide]1-{[2-fluoro-4-(2-oxo-pyridin-1-yl)-phenyl]-amide} and (1R,2S)-1-methyl-cyclopropane-1,2-dicarboxylic acid 2-[(5-chloro-pyridin-2-yl)-amide]1-{[2-fluoro-4-(2-oxo-pyridin-1-yl)-phenyl]-amide}

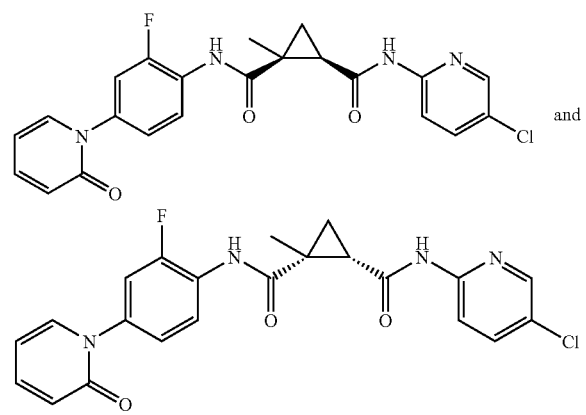

(1SR,2RS)-1-Methyl-cyclopropane-1,2-dicarboxylic acid 2-[(5-chloro-pyridin-2-yl)-amide]1-{[2-fluoro-4-(2-oxo-2H-pyridin-1-yl)-phenyl]-amide} (example 178.3) was separated into its enantiomers using HPLC on a chiral stationary phase (Chiralcel OD) using 20% EtOH in heptane as eluent to give (1S,2R)-1-methyl-cyclopropane-1,2-dicarboxylic acid 2-[(5-chloro-pyridin-2-yl)-amide]1-{[2-fluoro-4-(2-oxo-pyridin-1-yl)-phenyl]-amide} and (1R,2S)-1-methyl-cyclopropane-1,2-dicarboxylic acid 2-[(5-chloro-pyridin-2-yl)-amide]1-{[2-fluoro-4-(2-oxo-pyridin-1-yl)-phenyl]-amide}, both as off-white solids.

Example 180

(1SR,2RS)-1-methyl-cyclopropane-1,2-dicarboxylic acid 2-[(5-chloro-pyridin-2-yl)-amide]1-{[4-(3-oxo-morpholin-4-yl)-phenyl]-amide}

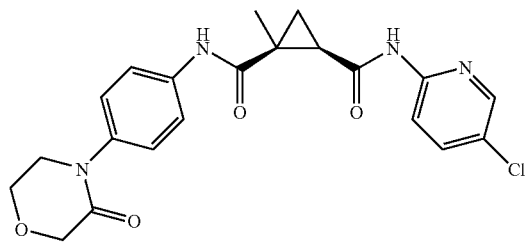

In analogy to example 178, step 3, (1SR,2RS)-2-(5-chloro-pyridin-2-ylcarbamoyl)-1-methyl-cyclopropanecarboxylic acid methyl ester (example 178, step 2) was reacted with 4-(4-amino-phenyl)-morpholin-3-one (CAS 438056-69-0) to give (1SR,2RS)-1-methyl-cyclopropane-1,2-dicarboxylic acid 2-[(5-chloro-pyridin-2-yl)-amide]1-{[4-(3-oxo-morpholin-4-yl)-phenyl]-amide} as light yellow solid. MS 427.4 ([M–H]⁻).

Example 181

(1SR,2RS)-1-methyl-cyclopropane-1,2-dicarboxylic acid 2-[(5-chloro-pyridin-2-yl)-amide]1-{[2-fluoro-4-(2-oxo-pyrazin-1-yl)-phenyl]-amide}

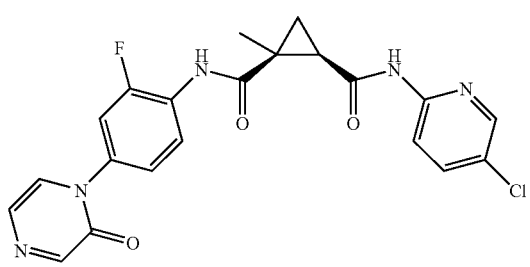

In analogy to example 178, step 3, (1SR,2RS)-2-(5-chloro-pyridin-2-ylcarbamoyl)-1-methyl-cyclopropanecarboxylic acid methyl ester (example 178, step 2) was reacted with 1-(4-amino-3-fluoro-phenyl)-1H-pyrazin-2-one (prepared from 2-fluoro-4-iodoaniline by reaction with 1H-pyrazin-2-one, Cu(I)I, N,N'-dimethylethylenediamine and cesium carbonate in dioxane at 120° C.) to give (1SR,2RS)-1-methyl-cyclopropane-1,2-dicarboxylic acid 2-[(5-chloro-pyridin-2-yl)-amide]1-{[2-fluoro-4-(2-oxo-pyrazin-1-yl)-phenyl]-amide} as off-white solid. MS 440.3 ([M–H]⁻).

Example 182

(1SR,2RS)-1-methyl-cyclopropane-1,2-dicarboxylic acid 2-[(5-chloro-pyridin-2-yl)-amide]1-{[4-(2-oxo-pyridin-1-yl)-phenyl]-amide}

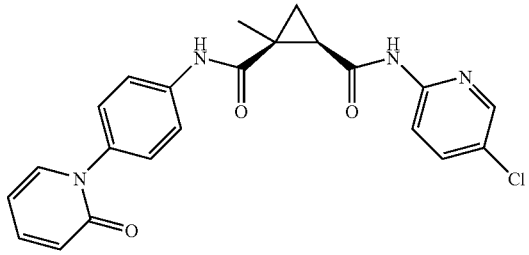

In analogy to example 178, step 3, (1SR,2RS)-2-(5-chloro-pyridin-2-ylcarbamoyl)-1-methyl-cyclopropanecarboxylic acid methyl ester (example 178, step 2) was reacted with 1-(4-amino-phenyl)-1H-pyridin-2-one (CAS 13143-47-0) to give (1SR,2RS)-1-methyl-cyclopropane-1,2-dicarboxylic acid 2-[(5-chloro-pyridin-2-yl)-amide]1-{[4-(2-oxo-pyridin-1-yl)-phenyl]-amide} as off-white solid. MS 421.1 ([M−H]⁻)

Example 183

(1SR,2RS)-1-methyl-cyclopropane-1,2-dicarboxylic acid 2-[(5-chloro-pyridin-2-yl)-amide]1-{[2-fluoro-4-(3-oxo-morpholin-4-yl)-phenyl]-amide}

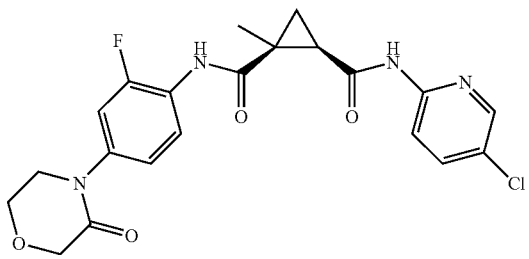

In analogy to example 178, step 3, (1SR,2RS)-2-(5-chloro-pyridin-2-ylcarbamoyl)-1-methyl-cyclopropanecarboxylic acid methyl ester (example 178, step 2) was reacted with 4-(4-amino-3-fluoro-phenyl)-morpholin-3-one (CAS 438056-69-0) to give (1SR,2RS)-1-methyl-cyclopropane-1,2-dicarboxylic acid 2-[(5-chloro-pyridin-2-yl)-amide]1-{[2-fluoro-4-(3-oxo-morpholin-4-yl)-phenyl]-amide} as yellow solid. MS 445.1 ([M−H]⁻)

Example 184

(1SR,2RS)-1-methyl-cyclopropane-1,2-dicarboxylic acid 2-[(5-chloro-pyridin-2-yl)-amide]1-{[2-methyl-4-(2-oxo-pyridin-1-yl)-phenyl]-amide}

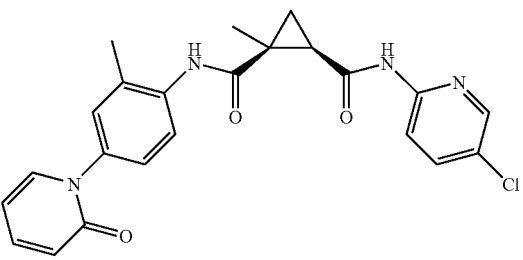

In analogy to example 178, step 3, (1SR,2RS)-2-(5-chloro-pyridin-2-ylcarbamoyl)-1-methyl-cyclopropanecarboxylic acid methyl ester (example 178, step 2) was reacted with 1-(4-amino-3-methyl-phenyl)-1H-pyridin-2-one to give (1SR,2RS)-1-methyl-cyclopropane-1,2-dicarboxylic acid 2-[(5-chloro-pyridin-2-yl)-amide]1-{[2-methyl-4-(2-oxo-pyridin-1-yl)-phenyl]-amide} as off-white solid. MS 435.1 ([M−H]⁻)

Example 185

(1SR,2RS)-1-methyl-cyclopropane-1,2-dicarboxylic acid 1-[(5-chloro-pyridin-2-yl)-amide]2-{[2-fluoro-4-(2-oxo-pyridin-1-yl)-phenyl]-amide}

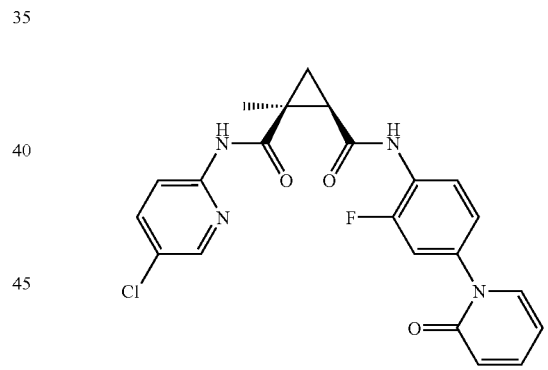

Step 1:

In analogy to example 178, step 1, 1-methyl-1,2-cyclopropanedicarboxylic acid (CAS 82235-80-1) was converted into the corresponding anhydride and then reacted with 1-(4-amino-3-fluoro-phenyl)-1H-pyridin-2-one (CAS 536747-52-1, prepared according to C. F. Bigge et al., patent application WO 2003045912) to give (1SR,2RS)-2-[2-fluoro-4-(2-oxo-pyridin-1-yl)-phenylcarbamoyl]-1-methyl-cyclopropanecarboxylic acid. Off-white solid.

Step 2:

In analogy to example 178, step 2, (1SR,2RS)-2-[2-gluoro-4-(2-oxo-pyridin-1-yl)-phenylcarbamoyl]-1-methyl-cyclopropanecarboxylic acid was converted to (1SR,2RS)-2-[2-fluoro-4-(2-oxo-pyridin-1-yl)-phenylcarbamoyl]-1-methyl-cyclopropanecarboxylic acid methyl ester. White amorphous solid. 345.4 ([M+H]⁺).

Step 3:

In analogy to example 178, step 3, (1SR,2RS)-2-[2-fluoro-4-(2-oxo-pyridin-1-yl)-phenylcarbamoyl]-1-methyl-cyclopropanecarboxylic acid methyl ester was reacted with 2-amino-5-chloro-pyridine to give (1SR,2RS)-1-methyl-cyclopropane-1,2-dicarboxylic acid 1-[(5-chloro-pyridin-2-yl)-amide]2-{[2-fluoro-4-(2-oxo-pyridin-1-yl)-phenyl]-amide} as light yellow amourphous solid. MS 441.3 ([M+H]$^+$).

Example 186

(1RS,2SR)-cyclopropane-1,2-dicarboxylic acid 1-[(5-chloro-pyridin-2-yl)-amide]2-{[2-fluoro-4-(2-oxo-2H-pyridin-1-yl)-phenyl]-amide}

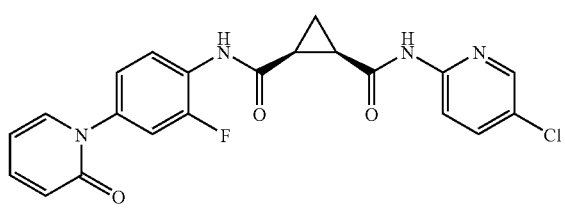

Step 1:

A solution of 3-oxabicyclo[3.1.0]hexane-2,4-dione (160 mg) in THF (5 ml) was treated with 1-(4-amino-3-fluoro-phenyl)-1H-pyridin-2-one (321 mg; CAS 536747-52-1, prepared according to C. F. Bigge et al., patent application WO 2003045912). The suspension was stirred over night at r.t. The solid was collected by filtration, triturated with 1N HCl (5 ml), again collected by filtration, washed with 1N HCl, H$_2$O, then cyclohexane and dried to give (1RS,2SR)-2-[2-fluoro-4-(2-oxo-2H-pyridin-1-yl)-phenylcarbamoyl]-cyclopropanecarboxylic acid (144 mg) as off-white solid. MS: 315.3 ([M–H]$^-$)

Step 2:

A stirred suspension of (1RS,2SR)-2-[2-fluoro-4-(2-oxo-2H-pyridin-1-yl)-phenylcarbamoyl]-cyclopropanecarboxylic acid (140 mg) in MeOH (5 ml) was cooled to 0° C. and treated with thionyl chloride (10 drops). The mixture turned immediately into a clear solution. Stirring was continued for 3 hrs at 0° C. Then the reaction mixture was concentrated. The crude product was purified by column chromatography (silica gel; gradient: CH$_2$Cl$_2$–>CH$_2$Cl$_2$/MeOH) to give (1RS,2SR)-2-[2-fluoro-4-(2-oxo-2H-pyridin-1-yl)-phenylcarbamoyl]-cyclopropanecarboxylic acid methyl ester (84 mg) as colorless amorphous solid. MS: 353.4 ([M+H]$^+$).

Step 3:

A solution of 2-amino-5-chloropyridine (125 mg) in dioxane (4 ml) was treated with trimethyl aluminium (2M in heptane; 0.48 ml) at r.t. under an argon atmosphere. After stirring for 1 hr at r.t., (1RS,2SR)-2-[2-fluoro-4-(2-oxo-pyridin-1-yl)-phenylcarbamoyl]-cyclopropanecarboxylic acid methyl ester (80 mg) in dioxane (1 ml) was added. The reaction was heated over night at 90° C., then cooled to r.t. and treated with H$_2$O (0.6 ml). After stirring for 15 min, Na$_2$SO$_4$ was added. After stirring for 15 min, the mixture was diluted with CH$_2$Cl$_2$ and filtered. The filtrate was concentrated. The crude product was purified by column chromatography (silica gel; gradient: CH$_2$Cl$_2$–>CH$_2$Cl$_2$/MeOH) to give (1RS,2SR)-cyclopropane-1,2-dicarboxylic acid 1-[(5-chloro-pyridin-2-yl)-amide]2-{[2-fluoro-4-(2-oxo-2H-pyridin-1-yl)-phenyl]-amide} (85 mg) as light yellow solid. MS: 427.4 ([M+H]$^+$).

Example 187

(1RS,2SR)-cyclopropane-1,2-dicarboxylic acid 1-[(4-chloro-phenyl)-amide]2-{[2-fluoro-4-(2-oxo-2H-pyridin-1-yl)-phenyl]-amide}

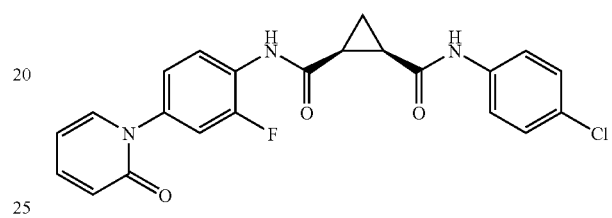

In analogy to example 186, step 2, (1RS,2SR)-2-[2-fluoro-4-(2-oxo-pyridin-1-yl)-phenylcarbamoyl]-cyclopropanecarboxylic acid methyl ester (example 1.2) was reacted with 4-chloroaniline to give (1RS,2SR)-cyclopropane-1,2-dicarboxylic acid 1-[(4-chloro-phenyl)-amide]2-{[2-fluoro-4-(2-oxo-2H-pyridin-1-yl)-phenyl]-amide} as off-white solid. MS: 426.0 ([M+H]$^+$).

Example 188

(1S,2R,3R)-3-hydroxymethyl-cyclopropane-1,2-dicarboxylic acid 1-[(5-chloro-pyridin-2-yl)-amide] 2-{[2-fluoro-4-(2-oxo-2H-pyridin-1-yl)-phenyl]-amide}

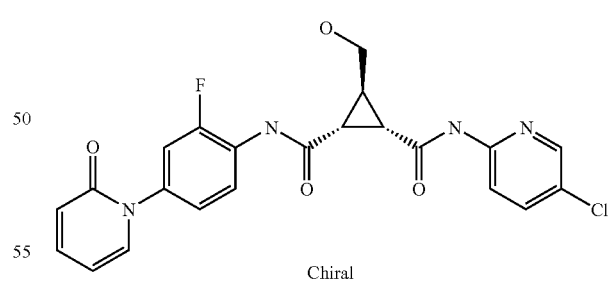

Chiral

In analogy to example 132, step 2, from (1S,2R,3R)-3-(4-methoxy-benzyloxymethyl)-cyclopropane-1,2-dicarboxylic acid 1-[(5-chloro-pyridin-2-yl)-amide]2-{[2-fluoro-4-(2-oxo-2H-pyridin-1-yl)-phenyl]-amide} (example 157) was prepared (1S,2R,3R)-3-hydroxymethyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}. Colorless solid. MS: 455 (M–H)$^-$.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavouring additives and filled into sachets.

Example F

Factor Xa activity was measured spectrophotometrically in microtiter plates in a final volume of 150 µl using the following conditions: Inhibition of human factor Xa (Enzyme Research Laboratories) was tested at an enzyme concentration of 3 nM using the chromogenic substrate S-2222 (Chromogenix AB, Mölndal, Sweden) at 200 nM. The reaction kinetics of the enzyme and the substrate were linear with both time and the enzyme concentration. The inhibitors were dissolved in DMSO and tested at various concentrations up to 100 µM. The inhibitors were diluted using HNPT buffer consisting of HEPES 100 mM, NaCl 140 mM, PEG 6000 0.1% and Tween 80 0.02%, pH 7.8. The cleavage of S-2222 by human factor Xa was followed at 405 nm for 5 minutes at room temperature. The velocity of the reaction was determined by the autoreader from the slope of the linear regression fit to 7 time points (1 minute). The initial velocity for each inhibitor concentration was determined by the slope of at least 4 time points in the linear phase by a linear regression fit (mOD/min$^2$). Apparent dissociation constants $K_i$ were calculated according to Cheng and Prusoff [Cheng, Y. C.; Prusoff, W. H. Relationship between the inhibition constant (Ks) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(1+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M., The action of thrombin on peptide p-nitroanilide substrates. Substrate selectivity and examination of hydrolysis under different reaction conditions. Biochim Biophys Acta. 1983 Feb. 15; 742(3):539-57]. according to Eadie [Eadie G. S. The inhibition of cholinesterase by physostigmine and prostigmine. J. Biol. Chem. 1942, 146, 85-93.]. The $K_m$ for S-2222 amounted to 613 μM.

| Example | Ki [μM] factor Xa |
|---|---|
| 47 | 0.009 |
| 48 | 0.008 |
| 52 | 0.013 |

What is claimed is:

1. A compound of formula (I)

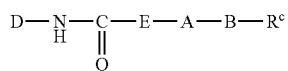

wherein

A is —CONH— or —NHCO—;

B is optionally substituted phenyl, optionally substituted heteroaryl or optionally substituted heterocyclyl;

$R^c$ is optionally substituted aryl, optionally substituted heteroaryl or optionally substituted heterocyclyl, one or two carbon atoms of said aryl, heteroaryl or heterocyclyl ring optionally being replaced with a carbonyl group;

D is aryl optionally substituted by one, two or three halogen atoms independently selected from chlorine, fluorine and bromine or heteroaryl optionally substituted by one, two or three halogen atoms independently selected from chlorine, fluorine and bromine;

E is E-1:

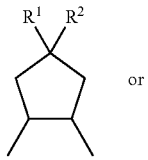

or

E-2:

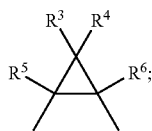

$R^1$ and $R^2$ are independently from each other hydrogen, halogen, $C_{1-6}$ alkyl, $C_{3-7}$ cycloalkyl, $C_{3-7}$ cycloalkyl $C_{1-6}$ alkyl, amino, mono-substituted amino, di-substituted amino, hydroxy, $C_{1-6}$ alkoxy, mono-substituted amino-$C_{1-6}$ alkyl, di-substituted amino-$C_{1-6}$ alkyl, hydroxyl $C_{1-6}$ alkyl or $R^1$ and $R^2$ together form

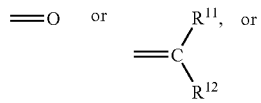

$R^1$ and $R^2$ are bonded to each other to form optionally substituted heterocyclyl, together with the carbon atom to which $R^1$ and $R^2$ are attached;

$R^3$ and $R^4$ are independently from each other hydrogen, $C_{1-6}$ alkyl, carboxyl, $C_{1-6}$ alkoxycarbonyl, carbamoyl, mono- or di-substituted amino-carbonyl, optionally substituted heterocyclylcarbonyl, optionally substituted heteroarylcarbonyl, optionally substituted aryl carbonyl, optionally substituted aryl, optionally substituted heteroaryl, optionally substituted heterocyclyl, hydroxyl $C_{1-6}$ alkyl, halo $C_{1-6}$ alkyl, cyano $C_{1-6}$ alkyl, $C_{1-6}$ alkoxy $C_{1-6}$ alkyl, amino $C_{1-6}$ alkyl, mono- or di-substituted amino-$C_{1-6}$ alkyl, optionally substituted aryl $C_{1-6}$ alkyl, optionally substituted heterocyclyl $C_{1-6}$ alkyl, optionally substituted heteroaryl $C_{1-6}$ alkyl, optionally substituted aryl $C_{1-6}$ alkoxy $C_{1-6}$ alkyl, optionally substituted heteroaryl $C_{1-6}$ alkoxy $C_{1-6}$ alkyl, optionally substituted heterocyclyl $C_{1-6}$ alkoxy $C_{1-6}$ alkyl or $R^3$ and $R^4$ are bonded to each other to form $C_{3-7}$ cycloalkyl, together with the carbon atom to which $R^3$ and $R^4$ are attached;

$R^5$ and $R^6$ are independently from each other hydrogen, $C_{1-6}$ alkyl, cyano, $C_{1-6}$ alkoxycarbonyl, $C_{2-6}$ alkenyloxycarbonyl, $C_{2-6}$ alkynyloxycarbonyl, hydroxyl $C_{1-6}$ alkyl, $C_{1-6}$ alkoxycarbonyl, carboxyl, mono- or di-$C_{1-6}$ alkyl substituted amino-carbonyl, aminocarbonyl, optionally substituted heterocyclyl carbonyl, optionally substituted heteroaryl carbonyl or optionally substituted aryl carbonyl;

$R^{11}$ and $R^{12}$ are independently from each other hydrogen, $C_{1-6}$ alkyl or $C_{2-6}$ alkenyl;

or pharmaceutically acceptable salts thereof.

2. A compound according to claim 1, wherein $R^3$ and $R^4$ are independently from each other hydrogen, $C_{1-6}$ alkyl, carboxyl, $C_{1-6}$ alkoxycarbonyl, carbamoyl, mono- or di-substituted amino-carbonyl, optionally substituted heterocyclylcarbonyl, optionally substituted heteroarylcarbonyl, aryl, optionally substituted heteroaryl, optionally substituted heterocyclyl, hydroxyl $C_{1-6}$ alkyl, $C_{1-6}$ alkoxy $C_{1-6}$ alkyl, amino $C_{1-6}$ alkyl, mono- or di-substituted amino-$C_{1-6}$ alkyl, optionally substituted heterocyclyl $C_{1-6}$ alkyl, optionally substituted heteroaryl $C_{1-6}$ alkyl or $R^3$ and $R^4$ are bonded to each other to form $C_{3-7}$ cycloalkyl, together with the carbon atom to which $R^3$ and $R^4$ are attached;

$R^5$ and $R^6$ are independently from each other hydrogen or $C_{1-6}$ alkyl;

optionally substituted phenyl is a phenyl group optionally substituted by one to five substituents independently selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro and cyano;

optionally substituted aryl is an aryl group optionally substituted by one to five substituents independently selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro and cyano;

optionally substituted heterocyclyl is a heterocyclyl group optionally substituted independently by one, two, or three substituents selected from the group consisting of halogen, hydroxy, $C_{1-6}$ alkyl, halo $C_{1-6}$ alkyl, $C_{1-6}$ alkoxy, acyl, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano;

optionally substituted heteroaryl is a heteroaryl group optionally substituted independently with one, two, or three substituents selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro and cyano; and mono-substituted amino and di-substituted amino are —NHR and —NRR' respectively, in which R and R' are independently selected from the group consisting of hydroxy, $C_{1-6}$ alkyl, hydroxyl $C_{1-6}$ alkyl, $C_{1-6}$ alkoxy $C_{1-6}$ alkyl, carbamoyl $C_{1-6}$ alkyl, halo $C_{1-6}$ alkyl, $C_{3-7}$ cycloalkyl, $C_{3-7}$ cycloalkyl $C_{1-6}$ alkyl, $C_{1-6}$ alkoxy, $C_{1-6}$ alkyl sulfonyl, $C_{1-6}$ alkyl sulfinyl, $C_{1-6}$ alkylthio, mono- or di-$C_{1-6}$ alkyl substituted amino-sulfonyl, mono- or di-$C_{1-6}$ alkyl substituted amino-sulfinyl, mono- or di-$C_{1-6}$ alkyl substituted amino-thio, mono- or di-$C_{1-6}$ alkyl substituted amino-$C_{1-6}$ alkyl, mono- or di-$C_{1-6}$ alkyl substituted aminocarbonyl-$C_{1-6}$ alkyl, acyl and $C_{1-6}$ alkoxycarbonyl.

3. A compound according to claim 1, wherein $R^3$ and $R^4$ are independently from each other hydrogen, $C_{1-6}$ alkyl, carboxyl, $C_{1-6}$ alkoxycarbonyl, mono- or di-substituted amino-carbonyl, optionally substituted heterocyclylcarbonyl, aryl, optionally substituted heteroaryl, optionally substituted heterocyclyl, hydroxyl $C_{1-6}$ alkyl, $C_{1-6}$ alkoxy $C_{1-6}$ alkyl, amino $C_{1-6}$ alkyl, mono- or di-substituted amino-$C_{1-6}$ alkyl, optionally substituted heterocyclyl $C_{1-6}$ alkyl, optionally substituted heteroaryl $C_{1-6}$ alkyl or $R^3$ and $R^4$ are bonded to each other to form $C_{3-7}$ cycloalkyl, together with the carbon atom to which $R^3$ and $R^4$ are attached;

heterocyclyl is non-aromatic monocyclic radicals of three to eight ring atoms in which one or two ring atoms are heteroatoms selected from N, O, or $S(O)_n$ (where n is an integer from 0 to 2), the remaining ring atoms being C;

optionally substituted heterocyclyl is a heterocyclyl group optionally substituted independently by one, two, or three substituents selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro and cyano;

the term "heteroaryl" means a monocyclic or bicyclic radical of 5 to 12 ring atoms having at least one aromatic ring containing one, two, or three ring heteroatoms selected from N, O, and S, the remaining ring atoms being C, wherein the attachment point of the heteroaryl radical will be on an aromatic ring;

mono-substituted amino and di-substituted amino are —NHR and —NRR' respectively, in which R and R' are independently selected from the group consisting of hydroxy, $C_{1-6}$ alkyl, hydroxyl $C_{1-6}$ alkyl, halo $C_{1-6}$ alkyl, $C_{3-7}$ cycloalkyl, $C_{3-7}$ cycloalkyl $C_{1-6}$ alkyl, $C_{1-6}$ alkoxy, $C_{1-6}$ alkyl sulfonyl, $C_{1-6}$ alkyl sulfinyl, $C_{1-6}$ alkylthio, mono- or di-$C_{1-6}$ alkyl substituted amino-sulfonyl, mono- or di-$C_{1-6}$ alkyl substituted amino-sulfinyl, mono- or di-$C_{1-6}$ alkyl substituted amino-thio, acyl and $C_{1-6}$ alkoxycarbonyl.

4. A compound according to claim 1, wherein E is E-1.

5. A compound according to claim 4, wherein D is aryl optionally substituted by one halogen atom selected from chlorine and bromine or heteroaryl optionally substituted by one halogen atom selected from chlorine and bromine.

6. A compound according to claim 4, wherein D is phenyl, pyridyl, thienyl, pyrimidinyl, pyridazinyl or indolyl, said phenyl, pyridyl, thienyl, pyrimidinyl, pyridazinyl or indolyl being optionally substituted by one halogen atom selected from chlorine and bromine.

7. A compound according to claim 4, wherein D is chlorophenyl or chloropyridyl.

8. A compound according to claim 4, wherein B is optionally substituted phenyl or optionally substituted heteroaryl.

9. A compound according to claim 4, wherein B is phenyl or pyridyl, said phenyl or pyridyl being optionally substituted by one or two halogen atoms selected independently from the group consisting of chlorine, fluorine and bromine.

10. A compound according to claim 4, wherein B is phenyl substituted by one or two fluorine.

11. A compound according to claim 4, wherein B is fluorophenyl.

12. A compound according to claim 4, wherein B is 2-fluorophenyl.

13. A compound according to claim 4, wherein $R^c$ is aryl, heteroaryl or heterocyclyl, one carbon atom of said aryl, heteroaryl or heterocyclyl ring optionally being replaced with a carbonyl group, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl.

14. A compound according to claim 4, wherein $R^c$ is aryl, heteroaryl or heterocyclyl, one carbon atom of said aryl, heteroaryl or heterocyclyl ring being replaced with a carbonyl group at ortho position with respect to B, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl.

15. A compound according to claim 4, wherein $R^c$ is 2-oxo-2H-pyridin-1-yl optionally substituted by $C_{1-6}$ alkyl or $C_{1-6}$ alkoxy.

16. A compound according to claim 4, wherein —B—$R^c$ is 2-fluoro-4-(2-oxo-2H-pyridin-1-yl)-phenyl.

17. A compound according to claim 4, wherein $R^1$ and $R^2$ are independently from each other hydrogen, hydroxy, $C_{1-6}$ alkoxy, hydroxy $C_{1-6}$ alkyl or $R^1$ and $R^2$ together form

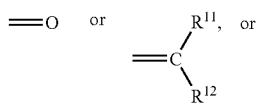

$R^1$ and $R^2$ are bonded to each other to form optionally substituted heterocyclyl, together with the carbon atom to which $R^1$ and $R^2$ are attached.

18. A compound according to claim 4, wherein $R^1$ and $R^2$ are independently from each other hydrogen, hydroxy, $C_{1-6}$ alkoxy, hydroxy $C_{1-6}$ alkyl or
$R^1$ and $R^2$ together form

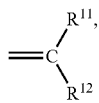

in which $R^{11}$ and $R^{12}$ are hydrogen, or
$R^1$ and $R^2$ are bonded to each other to form

together with the carbon atom to which $R^1$ and $R^2$ are attached.

19. A compound according to claim 4, wherein $R^1$ and $R^2$ together form

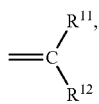

in which $R^{11}$ and $R^{12}$ are hydrogen.

20. A compound according to claim 4, wherein A is —CONH—.

21. A compound according to claim 4, which is
(1S,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide},
(1R,2S)-4-Methylene-cyclopentane-1,2-dicarboxylic acid 1-[(4-chloro-phenyl)-amide]2-{[2-fluoro-4-(2-oxo-2H-pyridin-1-yl)-phenyl]-amide},
(1S,2S,4S)- or (1S,2S,4R)-4-Hydroxymethyl-4-methoxy-cyclopentane-1,2-dicarboxylic acid 1-[(4-chloro-phenyl)-amide]2-{[2-fluoro-4-(2-oxo-2H-pyridin-1-yl)-phenyl]-amide},
(5S,6S)-Spiro[2.4]heptane-5,6-dicarboxylic acid (4-chloro-phenyl)-amide[2-fluoro-4-(2-oxo-2H-pyridin-1-yl)-phenyl]-amide,
(1S,2S,4S)-4-Fluoro-cyclopentane-1,2-dicarboxylic acid 1-[(4-chloro-phenyl)-amide]2-{[2-fluoro-4-(2-oxo-2H-pyridin-1-yl)-phenyl]-amide},
(1S,2S,4R)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide},
(1S,2S,4S)-4-Hydroxy-cyclopentane-1,2-dicarboxylic acid 1-[(4-chloro-phenyl)-amide]2-{[2-fluoro-4-(2-oxo-2H-pyridin-1-yl)-phenyl]-amide}.

22. A compound according to claim 4, which is
(1S,2S,4S)-4-fluoro-cyclopentane-1,2-dicarboxylic acid 1-[(4-chloro-phenyl)-amide]2-{[2-fluoro-4-(2-oxo-2H-pyridin-1-yl)-phenyl]-amide},
(1S,2S,4R)-4-fluoro-cyclopentane-1,2-dicarboxylic acid 1-[(5-chloro-pyridin-2-yl)-amide]2-{[2-fluoro-4-(2-oxo-2H-pyridin-1-yl)-phenyl]-amide},
(1S,2S,4R)-4-fluoro-cyclopentane-1,2-dicarboxylic acid 1-[(5-chloro-pyridin-2-yl)-amide]2-{[2-fluoro-4-(2-oxo-2H-pyrazin-1-yl)-phenyl]-amide},
((1S,2S,4R)-4-fluoro-cyclopentane-1,2-dicarboxylic acid 1-[(5-chloro-pyridin-2-yl)-amide]2-{[4-(3-oxo-morpholin-4-yl)-phenyl]-amide}), or
(1S,2S,4R)-4-Fluoro-cyclopentane-1,2-dicarboxylic acid 1-[(5-chloro-pyridin-2-yl)-amide]2-{[2-fluoro-4-(3-oxo-morpholin-4-yl)-phenyl]-amide}.

23. A compound according to claim 1, wherein E is E-2.

24. A compound according to claim 23, wherein D is aryl optionally substituted by one halogen atom selected from chlorine and bromine or heteroaryl optionally substituted by one halogen atom selected from chlorine and bromine.

25. A compound according to claim 23, wherein D is phenyl, pyridyl, thienyl, pyrimidinyl, pyridazinyl or indolyl, said phenyl, pyridyl, thienyl, pyrimidinyl, pyridazinyl or indolyl being optionally substituted by one halogen atom selected from chlorine and bromine.

26. A compound according to claim 23, wherein D is chlorophenyl or chloropyridyl.

27. A compound according to claim 23, wherein B is optionally substituted phenyl or optionally substituted heteroaryl.

28. A compound according to claim 23, wherein B is phenyl or pyridyl, said phenyl or pyridyl being optionally substituted by one or two halogen atoms selected independently from the group consisting of chlorine, fluorine and bromine.

29. A compound according to claim 23, wherein B is phenyl substituted by one or two fluorine.

30. A compound according to claim 23, wherein B is fluorophenyl.

31. A compound according to claim 23, wherein B is 2-fluorophenyl.

32. A compound according to claim 23, wherein $R^c$ is aryl, heteroaryl or heterocyclyl, one carbon atom of said aryl, heteroaryl or heterocyclyl ring optionally being replaced with a carbonyl group, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl.

33. A compound according to claim 23, wherein $R^c$ is aryl, heteroaryl or heterocyclyl, one carbon atom of said aryl, heteroaryl or heterocyclyl ring being replaced with a carbonyl group at ortho position with respect to B, and said aryl, heteroaryl or heterocyclyl ring optionally being substituted by hydroxy, $C_{1-6}$ alkyl, $C_{1-6}$ alkoxy, $C_{1-6}$ alkyl sulfonyl, amino $C_{1-6}$ alkyl, mono-$C_{1-6}$ alkyl substituted amino-$C_{1-6}$ alkyl or di-$C_{1-6}$ alkyl substituted amino-$C_{1-6}$ alkyl.

34. A compound according to claim 23, wherein $R^c$ is 2-oxo-2H-pyridin-1-yl optionally substituted by $C_{1-6}$ alkyl or $C_{1-6}$ alkoxy.

35. A compound according to claim 23, wherein —B—$R^c$ is 2-fluoro-4-(2-oxo-2H-pyridin-1-yl)-phenyl.

36. A compound according to claim 23, wherein A is —CONH—.

37. A compound according to claim 23, wherein $R^3$ is hydrogen and $R^4$ is mono- or di-substituted amino-carbonyl.

38. A compound according to claim 23, wherein $R^3$ is hydrogen and $R^4$ is di-substituted amino-carbonyl, which is —C(O)—NRR', in which R is $C_{1-6}$ alkyl and R' is hydroxy $C_{1-6}$ alkyl.

39. A compound according to claim 23, wherein $R^3$ is hydrogen and $R^4$ is optionally substituted heterocyclylcarbonyl or optionally substituted heteroarylcarbonyl.

40. A compound according to claim 23, wherein $R^3$ is hydrogen and $R^4$ is optionally substituted heterocyclylcarbonyl in which the heterocyclyl group contains a nitrogen atom as a ring member, and the carbonyl carbon atom is bonded to the nitrogen atom of the heterocyclyl group.

41. A compound according to claim 23, which is (1S,2R,3S)-3-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1S,2R,3S)-3-pyrrolidin-1-ylmethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1S,2R,3S)-3-cyanomethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1S,2R,3S)-3-methoxymethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1SR,2RS)-1-cyano-cyclopropane-1,2-dicarboxylic acid 1-[(5-chloro-pyridin-2-yl)-amide]2-{[2-fluoro-4-(2-oxo-2H-pyridin-1-yl)-phenyl]-amide}, (1SR,2RS)-1-hydroxymethyl-cyclopropane-1,2-dicarboxylic acid 1-[(4-chloro-phenyl)-amide]2-{[2-fluoro-4-(2-oxo-2H-pyridin-1-yl)-phenyl]-amide}, (1SR, 2RS)-1-cyano-cyclopropane-1,2-dicarboxylic acid 2-[(5-chloro-pyridin-2-yl)-amide]1-{[2-fluoro-4-(2-oxo-2H-pyridin-1-yl)-phenyl]-amide}, (1SR,2RS)-1-hydroxymethyl-cyclopropane-1,2-dicarboxylic acid 2-[(4-chloro-phenyl)-amide]1-{[2-fluoro-4-(2-oxo-2H-pyridin-1-yl)-phenyl]-amide}, (1RS,2SR)-cyclopropane-1,2-dicarboxylic acid 1-[(5-chloro-pyridin-2-yl)-amide]2-{[2-fluoro-4-(2-oxo-pyridin-1-yl)-phenyl]-amide}, or (1S,2R,3R)-3-hydroxymethyl-cyclopropane-1,2-dicarboxylic acid 1-[(5-chloro-pyridin-2-yl)-amide]2-{[2-fluoro-4-(2-oxo-2H-pyridin-1-yl)-phenyl]-amide}.

42. A pharmaceutical composition comprising a compound according to claim 1 and a pharmaceutically acceptable excipient.

\* \* \* \* \*